United States Patent
Dao et al.

(10) Patent No.: US 11,690,872 B2
(45) Date of Patent: Jul. 4, 2023

(54) METHODS FOR EXPANDING AND ACTIVATING γδ T CELLS FOR THE TREATMENT OF CANCER AND RELATED MALIGNANCIES

(71) Applicant: Immatics US, Inc., Houston, TX (US)

(72) Inventors: Monique Dao, Houston, TX (US); Steffen Walter, Houston, TX (US); Melinda Mata, Houston, TX (US); Aleksandra Nowicka, Houston, TX (US); Yannick Bulliard, Houston, TX (US); Sarah Missell, Tuebingen (DE); Sabrina Kuttruff-Coqui, Filderstadt-Sielmingen (DE); Norbert Hilf, Kirchentellinsfurt (DE)

(73) Assignee: IMMATICS US, INC., Houston, TX (US)

( * ) Notice: Subject to any disclaimer, the term of this patent is extended or adjusted under 35 U.S.C. 154(b) by 671 days.

(21) Appl. No.: 16/200,308

(22) Filed: Nov. 26, 2018

(65) Prior Publication Data

US 2019/0175650 A1    Jun. 13, 2019

Related U.S. Application Data

(60) Provisional application No. 62/591,041, filed on Nov. 27, 2017.

(30) Foreign Application Priority Data

Nov. 27, 2017   (DE) .......................... 102017127984.9

(51) Int. Cl.
| | | |
|---|---|---|
| *A61K 35/17* | (2015.01) | |
| *C12N 5/0783* | (2010.01) | |
| *A61K 31/663* | (2006.01) | |
| *A61K 31/675* | (2006.01) | |
| *A61K 38/20* | (2006.01) | |
| *C07K 14/54* | (2006.01) | |
| *C07K 14/55* | (2006.01) | |
| *C12N 5/00* | (2006.01) | |
| *C12N 15/62* | (2006.01) | |
| *C12N 15/85* | (2006.01) | |
| *A61K 35/12* | (2015.01) | |
| *C07K 16/28* | (2006.01) | |

(52) U.S. Cl.
CPC ............ *A61K 35/17* (2013.01); *A61K 31/663* (2013.01); *A61K 31/675* (2013.01); *A61K 38/2013* (2013.01); *C07K 14/5443* (2013.01); *C07K 14/55* (2013.01); *C12N 5/0018* (2013.01); *C12N 5/0636* (2013.01); *C12N 5/0638* (2013.01); *C12N 15/62* (2013.01); *C12N 15/8509* (2013.01); *A61K 2035/122* (2013.01); *A61K 2035/124* (2013.01); *C07K 16/2809* (2013.01); *C12N 2501/155* (2013.01); *C12N 2501/2302* (2013.01); *C12N 2501/2315* (2013.01); *C12N 2501/515* (2013.01); *C12N 2501/998* (2013.01); *C12N 2740/10043* (2013.01)

(58) Field of Classification Search
CPC ....................................................... A61K 35/17
See application file for complete search history.

(56) References Cited

U.S. PATENT DOCUMENTS

| | | |
|---|---|---|
| 7,749,760 B2 | 7/2010 | Okamura et al. |
| 8,962,313 B2 | 2/2015 | Nieda et al. |
| 10,106,805 B2 | 10/2018 | Spangenberg et al. |
| 2010/0009447 A1 | 1/2010 | Okamura |
| 2011/0158954 A1 | 6/2011 | Ideno et al. |
| 2016/0175358 A1 | 6/2016 | Jakobovits et al. |
| 2016/0187351 A1 | 6/2016 | Weinschenk et al. |
| 2016/0280759 A1 | 9/2016 | Mahr et al. |
| 2016/0287687 A1 | 10/2016 | Mahr et al. |
| 2016/0346371 A1 | 12/2016 | Schoor et al. |
| 2016/0368965 A1 | 12/2016 | Mahr et al. |
| 2017/0002055 A1 | 1/2017 | Mahr et al. |
| 2017/0022251 A1 | 1/2017 | Rammensee et al. |
| 2017/0029486 A1 | 2/2017 | Mahr et al. |
| 2017/0035807 A1 | 2/2017 | Schuster et al. |

(Continued)

FOREIGN PATENT DOCUMENTS

| | | |
|---|---|---|
| CN | 103 756 962 A | 4/2014 |
| CN | 107249605 A | 10/2017 |

(Continued)

OTHER PUBLICATIONS

Ribot et al., 2021, Nature Reviews, vol. 21, pp. 221-232 (Year: 2021).*
Nada et al. (Feb. 2017, J. ImmunoTherapy of Cancer, vol. 5:9, pp. 1-23). (Year: 2017).*
Eylar et al. (1993, International Immunology, vol. 5(1), pp. 97-101). (Year: 1993).*
Hedges et al. (2015, Innate Immunity, vol. 21(6), pp. 598-608). (Year: 2015).*

(Continued)

*Primary Examiner* — Anoop K Singh
*Assistant Examiner* — David A Montanari
(74) *Attorney, Agent, or Firm* — McBee Moore & Vanik IP, LLC

(57) ABSTRACT

The present disclosure relates to expansion and activation of T cells. In an aspect, the present disclosure relates to expansion and activation of γδ T cells that may be used for transgene expression. In another aspect, the disclosure relates to expansion and activation of γδ T cells while depleting α- and/or β-TCR positive cells. T cell populations comprising expanded γδ T cell and depleted or reduced α- and/or β-TCR positive cells are also provided for by the instant disclosure. The disclosure further provides for methods of using the disclosed T cell populations.

16 Claims, 25 Drawing Sheets
(11 of 25 Drawing Sheet(s) Filed in Color)
Specification includes a Sequence Listing.

(56) References Cited

U.S. PATENT DOCUMENTS

| | | |
|---|---|---|
| 2017/0037089 A1 | 2/2017 | Mahr et al. |
| 2017/0096461 A1 | 4/2017 | Mahr et al. |
| 2017/0101473 A1 | 4/2017 | Mahr et al. |
| 2017/0136108 A1 | 5/2017 | Mahr et al. |
| 2017/0165335 A1 | 6/2017 | Weinschenk et al. |
| 2017/0165337 A1 | 6/2017 | Mahr et al. |
| 2017/0173132 A1 | 6/2017 | Mahr et al. |
| 2017/0189505 A1 | 7/2017 | Mahr et al. |
| 2017/0253633 A1 | 9/2017 | Mahr et al. |
| 2017/0260249 A1 | 9/2017 | Mahr et al. |
| 2017/0296640 A1 | 10/2017 | Schoor et al. |

FOREIGN PATENT DOCUMENTS

| | | |
|---|---|---|
| EP | 3 208 329 A1 | 8/2017 |
| WO | 1993/020221 A1 | 10/1993 |
| WO | 2014/072446 A1 | 5/2014 |
| WO | 2016/055996 A1 | 4/2016 |
| WO | 2016081518 A2 | 5/2016 |
| WO | 2016/087871 A1 | 6/2016 |
| WO | 2016/166544 A1 | 10/2016 |

OTHER PUBLICATIONS

Merten et al., J. Viral. 79:834-840, 2005.
Bell et al. Experimental Biology and Medicine 2010; 235: 1269-1276.
Wang et al. J. Viral. 81:10869-10878, 2007.
Di Nunzio et al., Hum. Gene Ther. 811-820 (2007).
Neff et al., Mal. Ther. 2:157-159 (2004).
Hu et al., Mal. Ther. 611-617 (2003).
Kelly et al., Blood Cells, Molecules, & Diseases 30:132-143 (2003) (abstract).
Search report for German Application No. 10 2017 127 984.9, dated Jan. 9, 2018.
Rincon-Orozco, B. et al., Activation of V gamma 9V delta 2 T Cells by NKG2D, J. Immunol. 2005; 175; S. 2144-2151.
Acker et al., "Interleukin-15 enhances the proliferation, stimulatory phenotype, and antitumor effector functions of human gamma delta T cells," Journal of Hematology & Oncology, vol. 9, No. 1, Sep. 29, 2016 (Sep. 29, 2016). XP055555493; DOI: 10.1186/s13045-016-0329-3. pp. 2-3, 6. Figure 3.
Garcia, V.E et al., "IL-15 enhances the response of human gamma delta T cells to nonpeptide [correction of nonpeptide] microbial antigens," Journal of Immunology, vol. 160, No. 9, May 1, 1998 (May 1, 1998), pp. 4322-4329. XP002788890.
Mohanadh, "Enhancing adoptive cancer immunotherapy with V[gamma]2V[delta]2 T cells through pulse zoledronate stimulation," Journal for Immunotherapy of Cancer, BIOMED Central Ltd., London, UK, vol. 5, No. 1, pp. 2-3, figures 5-6. XP021242440; DOI: 10.1186/S40425-017-0209-6.
Gu Yanjun et al., "Rapamycin together with TGF-[beta]1, IL-2 and IL-15 induces the generation of functional regulatory [gamma][delta]T cells from human peripheral blood monon," vol. 402, No. 1, Nov. 22, 2013 Nov. 22, 2013), pp. 82-87. XP028820466; DOI: 10.1016/J.JIM.2013.11.009.
International Search Report for PCT/US2018/062442, dated Mar. 6, 2019.
Guo H. H. et al., "Protein tolerance to random amino acid change", PNAS, vol. 101, No. 25, Jun. 22, 2004, pp. 9205-9210, www.pnas.org/cgi/doi/10.1073/pnas.0403255101.
Van Der Veken et al., "aB T Cell Receptor Transfer to yo T Cells Generates Functional Effector Cells without Mixed TCR Dimers In Vivo," The Journal of Immunology, (2009), vol. 182: 164-170.
Altvater, Bianca, et al. "Activated human γδ T cells induce peptide-specificCD8+ T-cell responses to tumor-associated self-antigens" Cancer Immunol Immunotherapy, vol. 61, No. 3, pp. 385-396, Mar. 2012.
Besser, M. J., et al. "Modifying interleukin-2 concentrations during culture improves function of T cells for adoptive immunotherapy", Cytotherapy, vol. 11, Issue 2, pp. 206-217, Jan. 2009.
Burjanadze, Maka, et al. "In vitro expansion of gamma delta T cells with anti-myeloma cell activity by Phosphostim and IL-2 in patients with multiple myeloma" British journal of haematology, vol. 139, No. 2, pp. 206-216, Oct. 2007.
Castella, Barbara, et al. "Vγ9Vδ2 T cell-based immunotherapy inhematological malignancies: from bench to bedside" Cellular and Molecular Life Sciences, vol. 68, No. 14, pp. 2419-2432, Jul. 2011.
Khan, Mohd Wajid A., et al. "Potential use of gdT cell-based vaccines in cancer immunotherapy" Frontiers in Immunology, vol. 5, Article 512, Oct. 2014.
Parente-Pereira, Ana C., et al. "Adoptive Immunotherapy of Epithelial Ovarian Cancer with Vγ9Vδ2 T Cells, Potentiated by Liposomal Alendronic Acid" Journal of Immunology, vol. 193, No. 11, pp. 5557-5566, Dec. 2014.
Sugie, Tomoharu, et al. "Zoledronic Acid-Induced Expansion of γδ T Cells from Early-Stage Breast Cancer Patients: Effect of IL-18 on Helper NK Cells" Cancer Immunol Immunotherapy, vol. 62, No. 4, pp. 677-687, Apr. 2013.

\* cited by examiner

METHODS FOR EXPANDING AND ACTIVATING γδ T CELLS FOR THE TREATMENT OF CANCER AND RELATED MALIGNANCIES

CROSS REFERENCE TO RELATED APPLICATION

This is an international application under the Patent Cooperation Treaty, which claims the benefit of U.S. Provisional Application Ser. No. 62/591,041, filed Nov. 27, 2017 and German Application 102017127984.9, filed Nov. 27, 2017, the contents of which are herein incorporated by reference in their entirety.

BACKGROUND

1. Field

The present disclosure relates to expansion and activation of T cells. In an aspect, the present disclosure relates to expansion and activation of γδ T cells that may be used for transgene expression. In another aspect, the disclosure relates to expansion and activation of γδ T cells while depleting α- and/or β-TCR positive cells. T cell populations comprising expanded γδ T cell and depleted or reduced α- and/or β-TCR positive cells are also provided for by the instant disclosure. The disclosure further provides for methods of using the disclosed T cell populations.

2. Background

γδ T cells represent a subset of T cells expressing the γδ TCR instead of the αβ TCR. γδ T cells can be divided into two primary subsets—the tissue-bound Vδ2-negative cells and the peripheral circulating Vδ2positive cells, more specifically Vγ9δ2. Both subsets have been shown to have anti-viral and anti-tumor activities. Unlike the conventional αβ TCR expressing cells, γδ TCR-expressing cells recognize their targets independent of the classical MHC I and II. Similar to natural killer (NK) T cells, γδ T cells express NKG2D, which binds to the non-classical MHC molecules, i.e., MHC class I polypeptide-related sequence A (MICA) and MHC class I polypeptide-related sequence B (MICB), present on stressed cells and/or tumor cells. γδ TCR recognizes a variety of ligands, e.g., stress and/or tumor-related phosphoantigen. γδ T cells mediate direct cytolysis of their targets via multiple mechanisms, i.e., TRAIL, FasL, perforin and granzyme secretion. In addition, γδ T cells expressing CD16 potentiates antibody-dependent cell mediated cytotoxicity (ADCC).

A problem of γδ T cells, which may be generally present in an amount of only 1 to 5% in peripheral blood, is that the purity and number of the γδ T cells sufficient for medical treatment cannot be secured, especially of a small amount of blood is collected and then the cells therefrom are activated and/or proliferated. Increasing the amount of blood collection from a patient to secure the purity and number of the γδ T cells sufficient for medical treatment also poses a problem in that it imposes a great burden on the patient.

To date, clinical trials with autologous Vγ9δ2 T cells may use a Vγ9δ2 T cell expansion protocol, which is a 14-day treatment of PBMC with bisphosphonate, i.e., zoledronate and pamidronate, and 100 U/ml IL-2. At best, this process may yield a 100-fold increase in total Vγ9δ2 T cells within 14 days; thereafter, the expansion rate decreases, coinciding with an increase in cell death. As such, the conventional Vγ9δ2 expansion protocol may not yield sufficient number of cells to qualify as a commercially viable allogeneic product.

U.S. Pat. No. 7,749,760 describes a Vγ9Vδ2 T cell proliferation agent containing bisphosphonate, interleukin 2 (IL-2), and interleukin 18 (IL-18).

U.S. Pat. No. 8,962,313 describes a method for simultaneous proliferation of disease antigen specific cytotoxic T lymphocytes (CTLs) and γδ T cells by adding a disease antigen to isolated peripheral blood; and culturing the resultant combination in a culture media containing an interleukin.

WO 2014/072446 describes a method of inducing IL-2-free proliferation of γδ T cells using a combination of a γδ T cell activator and IL-33 for use in therapy of infection, cancer, autoimmunity as well as other diseases.

WO 2016/166544 describes γδ T cells may be expanded in the presence of a phosphoantigen isopentenyl pyrophosphate (IPP) and cytokines may be provided in the step of culturing to encourage proliferation of γδ T cells and to maintain cellular phenotype of the peripheral blood mononuclear cells.

U.S. 2011/0158954 describes a method for preparing a γδ T cell population, in which the method includes the step of culturing a cell population containing γδ T cells, in the presence of (a) fibronectin, a fibronectin fragment or a mixture thereof and (b) an activating factor of γδ T cells.

U.S. 2016/0175358 describes positive and/or negative selection of cell surface markers expressed on the collected γδ T cells can be used to directly isolate γδ T cells from various sources, e.g., a peripheral blood sample, a cord blood sample, a tumor, a tumor biopsy, a tissue, a lymph, or from an epithelial sample of a subject. γδ T cells can be isolated from a complex sample based on positive or negative expression of CD4, CD8, TCRα, TCRβ, TCRδ, and other suitable cell surface markers.

There remains a need for methods that could prepare sufficient number of γδ T cells as a commercially viable therapeutic product. A solution to this technical problem is provided by the embodiments characterized in the claims.

BRIEF SUMMARY

In an aspect, the disclosure provides for a method of activating and/or expanding γδ T cells including isolating γδ T cells from a blood sample of a human subject, activating the isolated γδ T cells in the presence of an aminobisphosphonate and a cytokine compound or composition, and expanding the activated γδ T cells in the absence of an aminobisphosphonate and in the presence of a cytokine compound or composition.

In an aspect, the present application relates to methods of expanding and activating γδ T cells, including isolating the γδ T cells from peripheral blood mononuclear cells (PBMC) of a human subject, in which the isolation includes contacting the PBMC with anti-α and anti-β T cell receptor (TCR) antibodies, for example, biotin- or magnetic bead-conjugated anti-αβTCR antibodies, depleting α- and/or β-TCR positive cells from the PBMC, for example, by using streptavidin-microbeads or magnet, activating the isolated γδ T cells in the presence of at least one compound containing aminobisphosphonate and/or phosphoantigen, and at least one cytokine comprising human recombinant interleukin 2 (IL-2), and/or human recombinant interleukin 15 (IL-15), for example, IL-2 alone, IL-15 alone, or a combination of IL-2 and IL-15, and expanding the activated γδ T cells in the absence of the at least one compound and in the presence of the at least one cytokine.

In another aspect, the present disclosure relates to methods of expanding and activating γδ T cells, including isolating the γδ T cells from leukapheresis of a human subject, in which the isolation includes contacting the leukapheresis product with anti-α and anti-β T cell receptor (TCR) antibodies, for example, biotin- or magnetic bead-conjugated anti-αβTCR antibodies, depleting α- and/or β-TCR positive cells from the PBMC, for example, by using streptavidin-microbeads or magnet, activating the isolated γδ T cells in the presence of at least one compound containing aminobisphosphonate and/or phosphoantigen, and at least one cytokine comprising IL-2, and/or IL-15, and expanding the activated γδ T cells in the absence of the at least one compound and in the presence of the at least one cytokine.

In yet another aspect, the disclosure provides for a method of activating and expanding γδ T cells including isolating γδ T cells from a blood sample of a human subject, activating the isolated γδ T cells in the presence of an aminobisphosphonate, a Toll-like receptor 2 (TLR2) ligand, and a cytokine composition consisting essentially of IL-2 and IL-15, and expanding the activated γδ T cells in the absence of aminobisphosphonate and in the presence of said cytokine composition.

In an aspect, the disclosure provides for methods of activating T cells by utilizing methodology described herein. In another aspect, the disclosure provides for methods of expanding T cells by utilizing methodology described herein. In yet another aspect, the disclosure provides for methods of activating and expanding T cells by utilizing methodology described herein.

In an aspect, activation of the isolated γδ T cells is in the presence of zoledronic acid, a TLR2 ligand, and a cytokine composition consisting of IL-2 and IL-15. In another aspect, the cytokine composition consists of IL-2 or IL-15. In an aspect, methods described herein are in vitro methods.

In an aspect, γδ T cells are isolated from leukapheresis product, e.g., LeukoPak®, of a subject, for example, a human subject. In another aspect, γδ T cells are not isolated from peripheral blood mononuclear cells (PBMC), such as cord blood. In an aspect, the blood sample comprises peripheral blood mononuclear cells (PBMC) and/or leukapheresis product.

In another aspect, α- and/or β-TCR positive cells include αβ T cells and natural killer T (NKT) cells.

In a yet another aspect, aminobisphosphonate may be zoledronate, pamidronate, alendronate, risedronate, ibandronate, incadronate, clodronate, etidronate, or neridronate, a salt thereof and/or a hydrate thereof. In yet another aspect, the only aminobisphosphonate utilized in methods described herein is zoledronate.

In another aspect, phosphoantigen may be (E)-4-hydroxy-3-methyl-but-2-enyl pyrophosphate (HMBPP), isoprenoid pyrophosphates (farnesyl pyrophosphate (FPP), geranylgeranyl pyrophosphate (GGPP), isopentenyl pyrophosphate (IPP), or dimethylallyl diphosphate (DMAPP).

The disclosure further provides activating γδ T cells in the presence of an aminobisphosphonate, IL-2, and IL-15. In yet another aspect, activation is in the presence of an aminobisphosphonate and IL-2 or an aminobisphosphonate and IL-15.

In an aspect, activation is in the presence of phosphoantigen, IL-2, and IL-15; or in the presence of phosphoantigen and IL-15.

In another aspect, aminobisphosphonate is zoledronic acid.

In another aspect, phosphoantigen is IPP.

In another aspect, an aminobisphosphonate may be at a concentration from about 0.1 µM to about 500 µM, from about 0.1 µM to about 400 µM, from about 0.1 µM to about 300 µM, from about 0.1 µM to about 200 µM, from about 0.1 µM to about 100 µM, from about 0.5 µM to about 100 µM, from about 1 µM to about 500 µM, from about 1 µM to about 400 µM, from about 1 µM to about 300 µM, from about 1 µM to about 200 µM, from about 1 µM to about 100 µM, from about 1 µM to about 90 µM, from about 1 µM to about 80 µM, from about 1 µM to about 70 µM, from about 1 µM to about 60 µM, from about 1 µM to about 50 µM, from about 1 µM to about 40 µM, from about 1 µM to about 30 µM, from about 1 µM to about 20 µM, from about 1 µM to about 15 µM, from about 1 µM to about 10 µM, from about 1 µM to about 9 µM, from about 1 µM to about 8 µM, from about 1 µM to about 7 µM, from about 1 µM to about 6 µM, from about 1 µM to about 5 µM, from about 2 µM to about 5 µM, from about 3 µM to about 5 µM, from about 2 µM to about 5 µM, from about 2 µM to about 10 µM, from about 3 µM to about 8 µM, or from about 4 µM to about 6 µM.

In another aspect, an aminobisphosphonate may be at a concentration from about 0.1 µM to about 100 µM or from about 1 µM to about 100 µM. In another aspect, an aminobisphosphonate may be at a concentration about 5 µM.

In yet another aspect, the seeding density of the isolated γδ T cells during activation is from about $0.01 \times 10^6$ cells/cm$^2$ to about $1 \times 10^7$ cells/cm$^2$, from about $0.1 \times 10^6$ cells/cm$^2$ to about $5 \times 10^6$ cells/cm$^2$, from about $0.25 \times 10^6$ cells/cm$^2$ to about $5 \times 10^6$ cells/cm$^2$, from about $0.5 \times 10^6$ cells/cm$^2$ to about $5 \times 10^6$ cells/cm$^2$, from about $0.5 \times 10^6$ cells/cm$^2$ to about $4 \times 10^6$ cells/cm$^2$, from about $0.5 \times 10^6$ cells/cm$^2$ to about $3 \times 10^6$ cells/cm$^2$, from about $0.5 \times 10^6$ cells/cm$^2$ to about $2.5 \times 10^6$ cells/cm$^2$, from about $0.5 \times 10^6$ cells/cm$^2$ to about $2 \times 10^6$ cells/cm$^2$, from about $0.6 \times 10^6$ cells/cm$^2$ to about $2 \times 10^6$ cells/cm$^2$, from about $0.7 \times 10^6$ cells/cm$^2$ to about $2 \times 10^6$ cells/cm$^2$, from about $0.8 \times 10^6$ cells/cm$^2$ to about $2 \times 10^6$ cells/cm$^2$, from about $0.9 \times 10^6$ cells/cm$^2$ to about $2 \times 10^6$ cells/cm$^2$, from about $1 \times 10^6$ cells/cm$^2$ to about $2 \times 10^6$ cells/cm$^2$, or from about $1.5 \times 10^6$ cells/cm$^2$ to about $2 \times 10^6$ cells/cm$^2$.

In another aspect, the seeding density of the isolated γδ T cells during activation is from about $0.5 \times 10^6$ cells/cm$^2$ to about $3 \times 10^6$ cells/cm$^2$.

In an aspect, the concentration of IL-2 during activation and/or expansion is from about 10 IU/ml to about 1000 IU/ml, from about 10 IU/ml to about 500 IU/ml, from about 10 IU/ml to about 400 IU/ml, from about 10 IU/ml to about 300 IU/ml, from about 10 IU/ml to about 200 IU/ml, from about 10 IU/ml to about 150 IU/ml, from about 10 IU/ml to about 100 IU/ml, from about 20 IU/ml to about 100 IU/ml, from about 30 IU/ml to about 100 IU/ml, from about 40 IU/ml to about 100 IU/ml, from about 50 IU/ml to about 100 IU/ml, from about 75 IU/ml to about 125 IU/ml, from about 20 IU/ml to about 80 IU/ml, from about 25 IU/ml to about 100 IU/ml, or from about 50 IU/ml to about 150 IU/ml.

In another aspect, the concentration of IL-2 during activation and/or expansion is from about 50 IU/ml to about 100 IU/ml. In another aspect, the concentration of IL-15 during activation and/or expansion is from about 10 ng/ml to about 1 µg/ml, from about 10 ng/ml to about 500 ng/ml, from about 10 ng/ml to about 400 ng/ml, from about 10 ng/ml to about 300 ng/ml, from about 10 ng/ml to about 200 ng/ml, from about 10 ng/ml to about 150 ng/ml, from about 10 ng/ml to about 100 ng/ml, from about 20 ng/ml to about 100 ng/ml, from about 30 ng/ml to about 100 ng/ml, from about 40 ng/ml to about 100 ng/ml, from about 50 ng/ml to about 100 ng/ml, from about 60 ng/ml to about 100 ng/ml, from about 20 ng/ml to about 80 ng/ml, from about 30 ng/ml to about 60 ng/ml, or from about 50 ng/ml to about 120 ng/ml.

In another aspect, the concentration of IL-15 during activation and/or expansion is from about 50 ng/ml to about 100 ng/ml.

The disclosure further provides for aspects where activation is in the presence of zoledronic acid at a concentration of about 1 µM to about 100 µM, IL-2 at a concentration from about 10 IU/ml to about 200 IU/ml, and IL-15 at a concentration of about 10-500 ng/ml. In yet another aspect, expansion is in the presence of IL-2 at a concentration from about 10 IU/ml to about 100 IU/ml and/or IL-15 at a concentration of about 50-200 ng/ml.

In another aspect, cytokines may include IL-7, IL-18, and/or IL-21. In an aspect, methods described herein exclude one or more of IL-12, IL-7. IL-21, IL-18, IL-19, IL-33, IL-4, IL-9, and/or IL-23 during expansion, activation, or both expansion and activation.

In yet another aspect, at least one compound further includes a Toll-like receptor 2 (TLR2) ligand.

In an aspect, TLR2 ligand is selected from the group consisting of Amphotericin B, L-theanine, tannin, and polyphenols.

In another aspect, TLR2 ligand is Amphotericin B.

In yet another aspect, at least one compound further includes N-acetyl cysteine (NAC) and/or glutamine/glutamax.

In an aspect, the concentration of NAC is from about 1 mM to about 10 mM, about 2 mM to about 8 mM, about 0.5 mM to about 5 mM, or about 0.5 mM to about 2.5 mM In another aspect, at least one compound further includes a COX-2 inhibitor.

In yet another aspect, COX-2 inhibitor is Ibuprofen.

In an aspect, the expansion is further in the presence of N-acetyl cysteine (NAC) and/or glutamine/glutamax.

In an aspect, the concentration of NAC is from about 1 mM to about 10 mM.

In an aspect, a duration of activation is no more than about 7 days, about 10 days, about 12 days, about 14 days, about 16 days, or about 20 days.

In an aspect, a duration of activation is from 1 day to about 10 days, from 1 day to about 9 days, from 1 day to about 8 days, from 1 day to about 7 days, from 1 day to about 6 days, from 1 day to about 5 days, from 1 day to about 4 days, from about 2 days to about 10 days, from about 2 days to about 8 days, from about 2 days to about 7 days, about 3 days to about 7 days, or about 4 to about 6 days.

In another aspect, a duration of activation is from about 1 day to about 7 days.

In an aspect, a duration of expansion is more than about 7 days, about 10 days, about 12 days, about 14 days, about 16 days, about 20 days, about 22 days, about 24 days, about 26 days, about 28 days, or about 30 days. In an aspect, a duration of expansion is from about 7 days to about 30 days, from about 7 days to about 25 days, or from about 10 days to about 20 days.

In an aspect, the cell density of the γδ T cells during expansion is from about $0.1 \times 10^6$ cells/cm$^2$ to about $5 \times 10^6$ cells/cm$^2$, from about $0.25 \times 10^6$ cells/cm$^2$ to about $5 \times 10^6$ cells/cm$^2$, from about $0.5 \times 10^6$ cells/cm$^2$ to about $5 \times 10^6$ cells/cm$^2$, from about $0.5 \times 10^6$ cells/cm$^2$ to about $4 \times 10^6$ cells/cm$^2$, from about $0.5 \times 10^6$ cells/cm$^2$ to about $3 \times 10^6$ cells/cm$^2$, from about $0.5 \times 10^6$ cells/cm$^2$ to about $2.5 \times 10^6$ cells/cm$^2$, from about $0.5 \times 10^6$ cells/cm$^2$ to about $2 \times 10^6$ cells/cm$^2$, from about $0.6 \times 10^6$ cells/cm$^2$ to about $2 \times 10^6$ cells/cm$^2$, from about $0.7 \times 10^6$ cells/cm$^2$ to about $2 \times 10^6$ cells/cm$^2$, from about $0.8 \times 10^6$ cells/cm$^2$ to about $2 \times 10^6$ cells/cm$^2$, from about $0.9 \times 10^6$ cells/cm$^2$ to about $2 \times 10^6$ cells/cm$^2$, from about $1 \times 10^6$ cells/cm$^2$ to about $2 \times 10^6$ cells/cm$^2$, or from about $1.5 \times 10^6$ cells/cm$^2$ to about $2 \times 10^6$ cells/cm$^2$.

In another aspect, cytokines used in expansion may further include IL-18, IL-21, and IL-7.

In an aspect, the present application relates to a population of expanded and activated γδ T cells prepared by the method of any one of the aspects described herein.

In another aspect, the present application relates to the methods of enhancing viral transduction efficiency in γδ T cells, including transducing the expanded and activated γδ T cells prepared by the method of any one of the first to the sixteenth aspects with a recombinant viral vector.

In another aspect, the viral vector is a retroviral vector.

In another aspect, the viral vector is a γ-retroviral vector or a lentiviral vector.

In yet another aspect, the viral vector expresses CD8 and an αβ-TCR.

In an aspect, the present application relates to engineered γδ T cells prepared by the method of the present disclosure.

In an aspect, the present application relates to a population of expanded γδ T cells prepared by the method of the present disclosure, in which the concentration of the expanded γδ T cells is at least about $1 \times 10^5$ cells/ml, at least about $1 \times 10^6$ cells/ml, at least about $1 \times 10^7$ cells/ml, at least about $1 \times 10^8$ cells/ml, or at least about $1 \times 10^9$ cells/ml.

In an aspect, the present application relates to a method of treating cancer, comprising administering to a patient in need thereof an effective amount of the engineered γδ T cell prepared by the method of the present disclosure.

In an aspect, the cancer is selected from the group consisting of acute lymphoblastic leukemia, acute myeloid leukemia, adrenocortical carcinoma, AIDS-related cancers, AIDS-related lymphoma, anal cancer, appendix cancer, astrocytomas, neuroblastoma, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, Merkel cell skin carcinoma, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenstrom's macroglobulinemia, and Wilms tumor.

In an aspect, the cancer is melanoma.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Allogeneic T cell therapy may be based on genetically engineering allogeneic γδ T cells to express exogenous TCRs. In addition to the specific tumor recognition via the ectopic TCR, γδ T cells may have activity against numerous tumor types as described herein.

In an aspect, the present disclosure relates to expansion and/or activation of T cells. In another aspect, the present disclosure relates to expansion and/or activation of γδ T cells in the absence of agents that bind to epitopes specific to γδ TCRs, such as antibodies against γδ TCRs. In another aspect, the present disclosure relates to expansion and/or activation of γδ T cells that may be used for transgene expression.

The disclosure further relates to expansion and activation of γδ T cells while depleting α- and/or β-TCR positive cells. T cell populations comprising expanded γδ T cell and depleted or reduced α- and/or β-TCR positive cells are also provided for by the instant disclosure. The disclosure further provides for methods of using the disclosed T cell populations.

In an aspect, methods for producing large-scale Good Manufacturing Practice (GMP)-grade TCR engineered Vγ9δ2 T cells are provided herein.

In the absence of feeder cells, addition of IL-18 to purified γδ T cells enhances the expansion of γδ T cells with notable increase in the amount of surface high affinity receptor for IL-2 (CD25 or IL-2Ra). Further, Amphotericin B, a Toll-like receptor 2 (TLR2) ligand, can activate γδ T cells, CD8+ T cells, and NK cells and enhance the detection of surface expression of CD25, the high affinity IL-2Ra. Collectively, these observations highlight a critical role of IL-2 signaling in Zoledronate-mediated activation and expansion of Vγ9δ2 T cells. Thus, to maximize the availability of IL-2 for γδ T cell proliferation via IL-2 signaling (or to minimize the sequestration of IL-2 by high number of αβ T cells), methods of the present disclosure may include depleting αβ T cells from normal PBMC using anti-αβ TCR commercially available GMP reagents. As recombinant IL-18 is currently not available as a commercial GMP-reagent, methods of the present disclosure may supplement the culture with low dose Amphotericin B to increase CD25 surface expression to enhance IL-2 binding and signaling, which in turn may enhance IL-2 responsiveness during activation/expansion. In addition, IL-15 may be added because IL-15 has been shown to increase proliferation and survival of Vγ9δ2 T cells treated with IPP.

Figure 13:
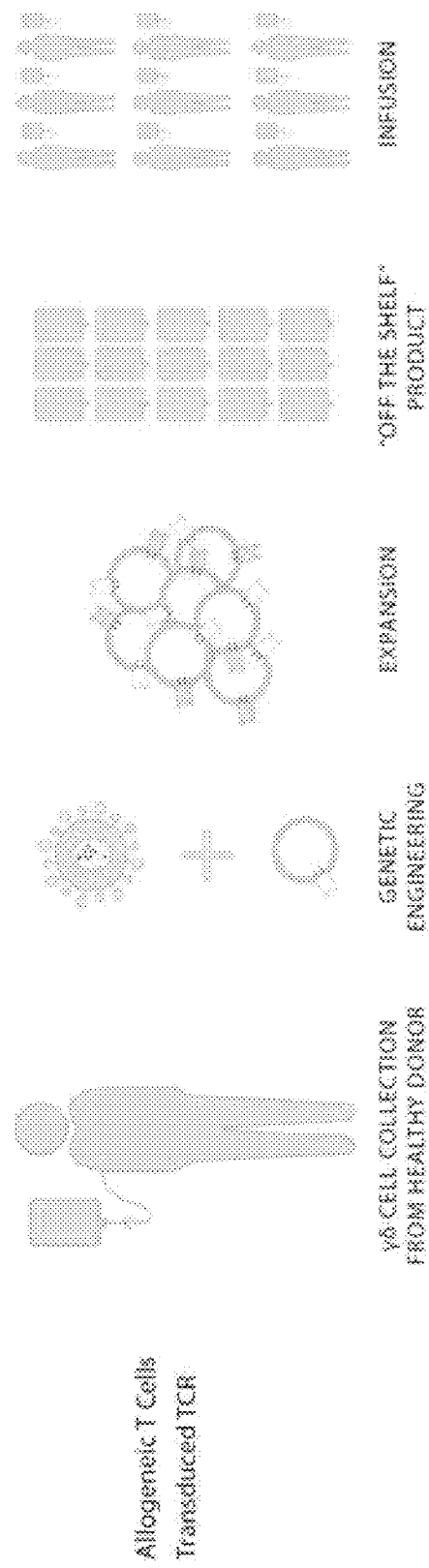
FIG. 13 shows allogenic T cell therapy according to an embodiment of the present disclosure. Allogenic T cell therapy may include collecting γδ T cells from healthy donors, engineering γδ T cells by viral transduction of exogenous genes of interest, such as exogenous TCRs, followed by cell expansion, harvesting the expanded engineered γδ T cells, which may be cryopreserved as "off-the-shelf" T-cell products, before infusing into patients.

FIG. 13 shows an approach for adoptive allogenic T cell therapy that can deliver "off-the-shelf" T-cell products, such as γδ T cell products, for rapid treatment of eligible patients with a specific cancer expressing the target of interest in their tumors. This approach may include collecting γδ T cells from healthy donors, engineering γδ T cells by viral transduction of exogenous genes of interest, such as exogenous TCRs, followed by cell expansion, harvesting the expanded engineered γδ T cells, which may be cryopreserved as "off-the-shelf" T-cell products, before infusing into patients. This approach therefore may eliminate the need for personalized T cell manufacturing.

To isolate γδ T cells, in an aspect, γδ T cells may be isolated from a subject or from a complex sample of a subject. In an aspect, a complex sample may be a peripheral blood sample, a cord blood sample, a tumor, a stem cell precursor, a tumor biopsy, a tissue, a lymph, or from epithelial sites of a subject directly contacting the external milieu or derived from stem precursor cells. γδ T cells may be directly isolated from a complex sample of a subject, for example, by sorting γδ T cells that express one or more cell surface markers with flow cytometry techniques. Wild-type γδ T cells may exhibit numerous antigen recognition, antigen-presentation, co-stimulation, and adhesion molecules that can be associated with a γδ T cells. One or more cell surface markers, such as specific γδ TCRs, antigen recognition, antigen-presentation, ligands, adhesion molecules, or co-stimulatory molecules may be used to isolate wild-type γδ T cells from a complex sample. Various molecules associated with or expressed by γδ T-cells may be used to isolate γδ T cells from a complex sample. In another aspect, the present disclosure provides methods for isolation of mixed population of Vδ1+, Vδ2+, Vδ3+ cells or any combination thereof.

For example, peripheral blood mononuclear cells can be collected from a subject, for example, with an apheresis machine, including the Ficoll-Paque™ PLUS (GE Healthcare) system, or another suitable device/system. γδ T-cell(s), or a desired subpopulation of γδ T-cell(s), can be purified from the collected sample with, for example, with flow cytometry techniques. Cord blood cells can also be obtained from cord blood during the birth of a subject.

Positive and/or negative selection of cell surface markers expressed on the collected γδ T cells can be used to directly isolate γδ T cells, or a population of γδ T cells expressing similar cell surface markers from a peripheral blood sample, a cord blood sample, a tumor, a tumor biopsy, a tissue, a lymph, or from an epithelial sample of a subject. For instance, γδ T cells can be isolated from a complex sample based on positive or negative expression of CD2, CD3, CD4, CD8, CD24, CD25, CD44, Kit, TCR α, TCR β, TCR α, TCR δ, NKG2D, CD70, CD27, CD30, CD16, CD337 (NKp30), CD336 (NKp46), OX40, CD46, CCR7, and other suitable cell surface markers.

In an aspect, γδ T cells may be isolated from a complex sample that is cultured in vitro. In another aspect, whole PBMC population, without prior depletion of specific cell populations, such as monocytes, αβ T-cells, B-cells, and NK cells, can be activated and expanded. In another aspect, enriched γδ T cell populations can be generated prior to their specific activation and expansion. In another aspects, activation and expansion of γδ T cells may be performed without the presence of native or engineered APCs. In another aspects, isolation and expansion of γδ T cells from tumor specimens can be performed using immobilized γδ T cell mitogens, including antibodies specific to γδ TCR, and other γδ TCR activating agents, including lectins. In another aspect, isolation and expansion of γδ T cells from tumor specimens can be performed in the absence of γδ T cell mitogens, including antibodies specific to γδ TCR, and other γδ TCR activating agents, including lectins.

In an aspect, γδ T cells are isolated from leukapheresis of a subject, for example, a human subject. In another aspect, γδ T cells are not isolated from peripheral blood mononuclear cells (PBMC).

Figure 14:
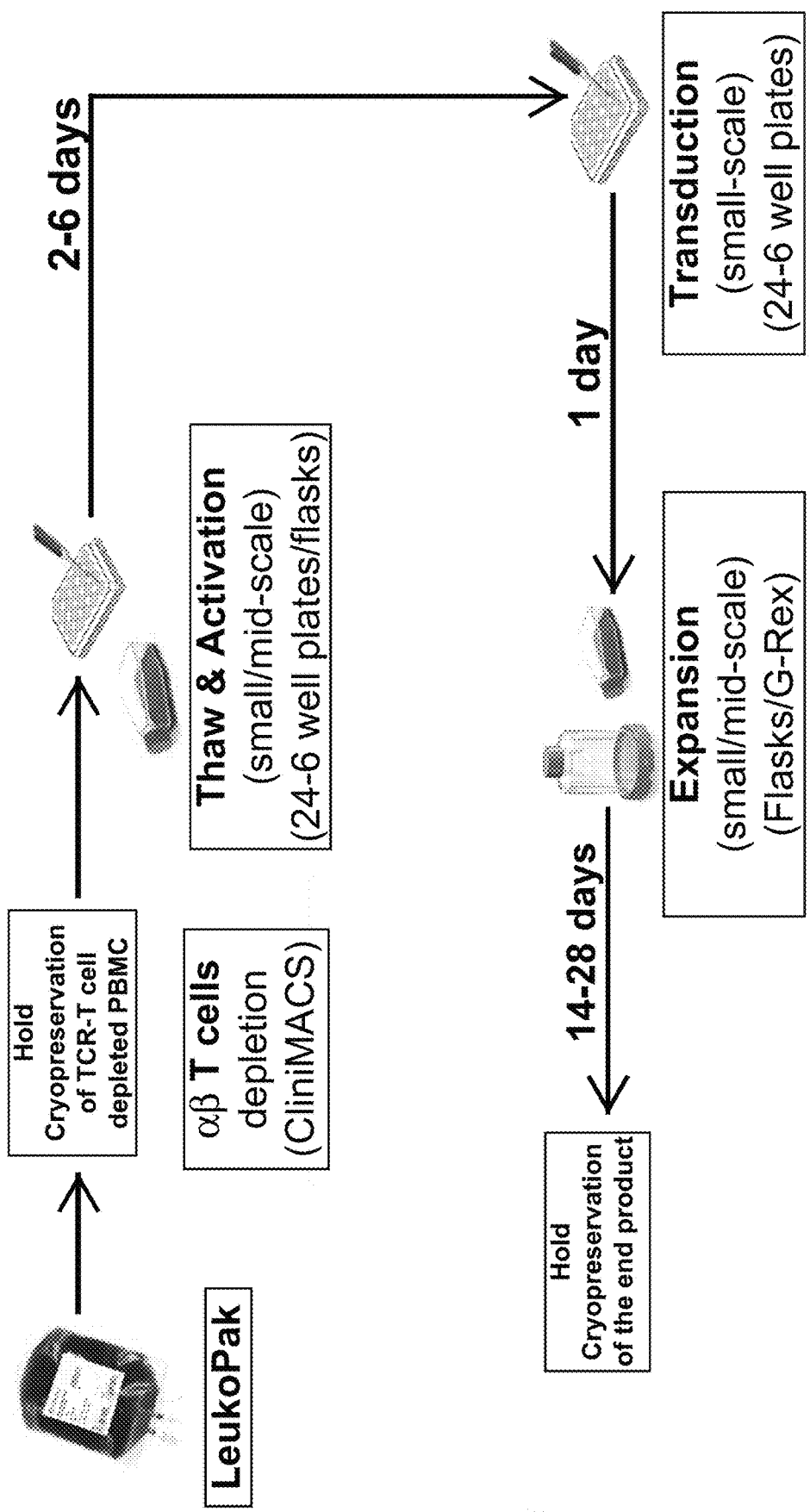
FIG. 14 shows γδ T cell manufacturing according to an embodiment of the present disclosure. γδ T cell manufacturing may include collecting or obtaining white blood cells or PBMC, e.g., leukapheresis product, depleting αβ T cells from PBMC or leukapheresis product, followed by activation, transduction, and expansion of γδ T cells.

FIG. 14 shows γδ T cell manufacturing according to an embodiment of the present disclosure. This process may include collecting or obtaining white blood cells or PBMC from leukapheresis products. Leukapheresis may include collecting whole blood from a donor and separating the components using an apheresis machine. An apheresis machine separates out desired blood components and returns the rest to the donor's circulation. For instance, white blood cells, plasma, and platelets can be collected using apheresis equipment, and the red blood cells and neutrophils are returned to the donor's circulation. Commercially available leukapheresis products may be used in this process. Another way to obtain white blood cells is to obtain them from the buffy coat. To isolate the buffy coat, whole anticoagulated blood is obtained from a donor and centrifuged. After centrifugation, the blood is separated into the plasma, red blood cells, and buffy coat. The buffy coat is the layer located between the plasma and red blood cell layers. Leukapheresis collections may result in higher purity and considerably increased mononuclear cell content than that achieved by buffy coat collection. The mononuclear cell content possible with leukapheresis may be typically 20 times higher than that obtained from the buffy coat. In order to enrich for mononuclear cells, the use of a Ficoll gradient may be needed for further separation.

To deplete αβ T cells from PBMC, αβ TCR-expressing cells may be separated from the PBMC by magnetic separation, e.g., using CliniMACS® magnetic beads coated with anti-αβ TCR antibodies, followed by cryopreserving αβ TCR-T cells depleted PBMC. To manufacture "off-the-shelf" T-cell products, cryopreserved αβ TCR-T cells depleted PBMC may be thawed and activated in small/mid-scale, e.g., 24 to 4-6 well plates or T75/T175 flasks, or in large scale, e.g., 50 ml-100 liter bags, in the presence of aminobisphosphonate and/or isopentenyl pyrophosphate (IPP) and/or cytokines, e.g., interleukin 2 (IL-2), interleukin 15 (IL-15), and/or interleukin 18 (IL-18), and/or other activators, e.g., Toll-like receptor 2 (TLR2) ligand, for 1-10 days, e.g., 2-6 days.

In an aspect, the isolated γδ T cells can rapidly expand in response to contact with one or more antigens. Some γδ T cells, such as Vγ9Vδ2+ T cells, can rapidly expand in vitro in response to contact with some antigens, like prenyl-pyrophosphates, alkyl amines, and metabolites or microbial extracts during tissue culture. Stimulated γδ T-cells can exhibit numerous antigen-presentation, co-stimulation, and adhesion molecules that can facilitate the isolation of γδ T-cells from a complex sample. γδ T cells within a complex sample can be stimulated in vitro with at least one antigen for 1 day, 2 days, 3 days, 4 days, 5 days, 6 days, 7 days, or another suitable period of time. Stimulation of γδ T cells with a suitable antigen can expand γδ T cell population in vitro.

Non-limiting examples of antigens that may be used to stimulate the expansion of γδ T cells from a complex sample in vitro may include, prenyl-pyrophosphates, such as isopentenyl pyrophosphate (IPP), alkyl-amines, metabolites of human microbial pathogens, metabolites of commensal bacteria, methyl-3-butenyl-1-pyrophosphate (2M3B1 PP), (E)-4-hydroxy-3-methyl-but-2-enyl pyrophosphate (HMB-PP), ethyl pyrophosphate (EPP), farnesyl pyrophosphate (FPP), dimethylallyl phosphate (DMAP), dimethylallyl pyrophosphate (DMAPP), ethyl-adenosine triphosphate (EPPPA), geranyl pyrophosphate (GPP), geranylgeranyl pyrophosphate (GGPP), isopentenyl-adenosine triphosphate (IPPPA), monoethyl phosphate (MEP), monoethyl pyrophosphate (MEPP), 3-formyl-1-butyl-pyrophosphate (TUBAg 1), X-pyrophosphate (TUBAg 2), 3-formyl-1-butyl-uridine triphosphate (TUBAg 3), 3-formyl-1-butyl-deoxythymidine triphosphate (TUBAg 4), monoethyl alkylamines, allyl pyrophosphate, crotoyl pyrophosphate, dimethylallyl-γ-uridine triphosphate, crotoyl-γ-uridine triphosphate, allyl-γ-uridine triphosphate, ethylamine, isobutylamine, sec-butylamine, iso-amylamine and nitrogen containing bisphosphonates.

Activation and expansion of γδ T cells can be performed using activation and co-stimulatory agents described herein to trigger specific γδ T cell proliferation and persistence populations. In an aspect, activation and expansion of γδ T-cells from different cultures can achieve distinct clonal or mixed polyclonal population subsets. In another aspect, different agonist agents can be used to identify agents that provide specific γδ activating signals. In another aspect, agents that provide specific γδ activating signals can be different monoclonal antibodies (MAbs) directed against the γδ TCRs. In another aspect, companion co-stimulatory agents to assist in triggering specific γδ T cell proliferation without induction of cell energy and apoptosis can be used. These co-stimulatory agents can include ligands binding to receptors expressed on γδ cells, such as NKG2D, CD161, CD70, JAML, DNAX accessory molecule-1 (DNAM-1), ICOS, CD27, CD137, CD30, HVEM, SLAM, CD122, DAP, and CD28. In another aspect, co-stimulatory agents can be antibodies specific to unique epitopes on CD2 and CD3 molecules. CD2 and CD3 can have different conformation structures when expressed on αβ or γδ T-cells. In another aspect, specific antibodies to CD3 and CD2 can lead to distinct activation of γδ T cells.

A population of γδ T-cell may be expanded ex vivo prior to engineering of the γδ T-cell. Non-limiting example of reagents that can be used to facilitate the expansion of a γδ T-cell population in vitro may include anti-CD3 or anti-CD2, anti-CD27, anti-CD30, anti-CD70, anti-OX40 antibodies, IL-2, IL-15, IL-12, IL-9, IL-33, IL-18, or IL-21, CD70 (CD27 ligand), phytohaemagglutinin (PHA), concavalin A (ConA), pokeweed (PWM), protein peanut agglutinin (PNA), soybean agglutinin (SBA), *lens culinaris* agglutinin (LCA), *Pisum sativum* agglutinin (PSA), *helix pomatia* agglutinin (HPA), *vicia graminea* Lectin (VGA), or another suitable mitogen capable of stimulating T-cell proliferation.

The ability of γδ T cells to recognize a broad spectrum of antigens can be enhanced by genetic engineering of the γδ T cells. In an aspect, γδ T cell can be engineered to provide a universal allogeneic therapy that recognizes an antigen of choice in vivo. Genetic engineering of the γδ T-cells may include stably integrating a construct expressing a tumor recognition moiety, such as αδ TCR, γδ TCR, chimeric antigen receptor (CAR), which combines both antigen-binding and T-cell activating functions into a single receptor, an antigen binding fragment thereof, or a lymphocyte activation domain into the genome of the isolated γδ T-cell(s), a cytokine (IL-15, IL-12, IL-2. IL-7. IL-21, IL-18, IL-19, IL-33, IL-4, IL-9, IL-23, IL1β) to enhance T-cell proliferation, survival, and function ex vivo and in vivo. Genetic engineering of the isolated γδ T-cell may also include deleting or disrupting gene expression from one or more endogenous genes in the genome of the isolated γδ T-cells, such as the MHC locus (loci).

In an aspect, viruses refers to natural occurring viruses as well as artificial viruses. Viruses in accordance to some embodiments of the present disclosure may be either an enveloped or non-enveloped virus. Parvoviruses (such as AAVs) are examples of non-enveloped viruses. In a preferred embodiment, the viruses may be enveloped viruses. In preferred embodiments, the viruses may be retroviruses and in particular lentiviruses. Viral envelope proteins that can promote viral infection of eukaryotic cells may include HIV-1 derived lentiviral vectors (LVs) pseudotyped with envelope glycoproteins (GPs) from the vesicular stomatitis virus (VSV-G), the modified feline endogenous retrovirus (RD114TR), and the modified gibbon ape leukemia virus (GALVTR). These envelope proteins can efficiently promote entry of other viruses, such as parvoviruses, including adeno-associated viruses (AAV), thereby demonstrating their broad efficiency. For example, other viral envelop proteins may be used including Moloney murine leukemia virus (MLV) 4070 env (such as described in Merten et al., *J. Virol.* 79:834-840, 2005; which is incorporated herein by reference), RD114 env (SEQ ID NO: 2), chimeric envelope protein RD114pro or RDpro (which is an RD114-HIV chimera that was constructed by replacing the R peptide cleavage sequence of RD114 with the HIV-1 matrix/capsid (MA/CA) cleavage sequence, such as described in Bell et al. *Experimental Biology and Medicine* 2010; 235: 1269-1276; which is incorporated herein by reference), baculovirus GP64 env (such as described in Wang et al. *J. Virol.* 81:10869-10878, 2007; which is incorporated herein by reference), or GALV env (such as described in Merten et al., *J. Virol.* 79:834-840, 2005; which is incorporated herein by reference), or derivatives thereof.

RD114TR

RD114TR is a chimeric envelope glycoprotein made of the extracellular and transmembrane domains of the feline leukemia virus RD114 and the cytoplasmic tail (TR) of the amphotropic murine leukemia virus envelope. RD114TR pseudotyped vectors can mediate efficient gene transfer into human hematopoietic progenitors and NOD/SCID repopulating cells. Di Nunzio et al., *Hum. Gene Ther:* 811-820 (2007)), the contents of which are incorporated by reference in their entirety. RD114 pseudotyped vectors can also mediate efficient gene transfer in large animal models. (Neff et al., *Mal. Ther.* 2:157-159 (2004); Hu et al., *Mal. Ther:* 611-617 (2003); and Kelly et al., *Blood Cells, Molecules, & Diseases* 30:132-143 (2003)), the contents of each of these references are incorporated by reference in their entirety.

The present disclosure may include RD114TR variants having at least about 50%, at least about 60%, at least about 70%, at least about 80%, at least about 90%, at least about 95%, at least about 98%, at least about 99%, or 100% sequence identity to the amino acid sequence of SEQ ID NO: 1 or SEQ ID NO: 5. For example, an RD114TR variant (RD114TRv1 (SEQ ID NO: 5)) having about 96% sequence identity to RD114TR (SEQ ID NO: 1) may be used. In an aspect, the disclosure provides for RD114TR variants having modified amino acid residues. A modified amino acid residue may be selected from an amino acid insertion, deletion, or substitution. In an aspect, a substitution described herein is a conservative amino acid substitution. That is, amino acids of RD114TR may be replaced by other amino acids having similar properties (conservative changes, such as similar hydrophobicity, hydrophilicity, antigenicity, propensity to form or break a-helical structures or 3-sheet structures). Non-limiting examples of conservative substitutions may be found in, for example, Creighton (1984) *Proteins*. W.H. Freeman and Company, the contents of which are incorporated by reference in their entirety.

In another aspect, the present disclosure may include variants having at least about 50%, at least about 60%, at least about 70%, at least about 80%, at least about 90%, at least about 95%, at least about 98%, at least about 99%, or 100% sequence identity to the amino acid sequence of SEQ ID NO: 1, 2, 3, 4, or 5.

In an aspect, conservative substitutions may include those, which are described by Dayhoff in "The Atlas of Protein Sequence and Structure. Vol. 5", *Natl. Biomedical Research*, the contents of which are incorporated by reference in their entirety. For example, in an aspect, amino acids, which belong to one of the following groups, can be exchanged for one another, thus, constituting a conservative exchange: Group 1: alanine (A), proline (P), glycine (G), asparagine (N), serine (S), threonine (T); Group 2: cysteine (C), serine (S), tyrosine (Y), threonine (T); Group 3: valine (V), isoleucine (I), leucine (L), methionine (M), alanine (A), phenylalanine (F); Group 4: lysine (K), arginine (R), histidine (H); Group 5: phenylalanine (F), tyrosine (Y), tryptophan (W), histidine (H); and Group 6: aspartic acid (D), glutamic acid (E).

In an aspect, conservative amino acid substitution may include the substitution of an amino acid by another one of the same class, for example, (1) nonpolar: Ala, Val, Leu, Ile, Pro, Met, Phe, Trp; (2) uncharged polar: Gly, Ser, Thr, Cys, Tyr, Asn, Gln; (3) acidic: Asp, Glu; and (4) basic: Lys, Arg, His. Other conservative amino acid substitutions may also be made as follows: (1) aromatic: Phe, Tyr, His; (2) proton donor: Asn, Gln, Lys, Arg, His, Trp; and (3) proton acceptor: Glu, Asp, Thr, Ser, Tyr, Asn, Gln (see, U.S. patent Ser. No. 10/106,805).

In another aspect, conservative substitutions may be made in accordance with Table A. Methods for predicting tolerance to protein modification may be found in, for example, Guo et al., *Proc. Natl. Acad. Sci., USA*, 101(25):9205-9210 (2004), the contents of which are incorporated by reference in their entirety.

TABLE A

Conservative Amino Acid Substitutions

| Amino Acid | Substitutions (others are known in the art) |
|---|---|
| Ala | Ser, Gly, Cys |
| Arg | Lys, Gln, His |
| Asn | Gln, His, Glu, Asp |
| Asp | Glu, Asn, Gln |
| Cys | Ser, Met, Thr |
| Gln | Asn, Lys, Glu, Asp, Arg |
| Glu | Asp, Asn, Gln |
| Gly | Pro, Ala, Ser |
| His | Asn, Gln, Lys |
| Ile | Leu, Val, Met, Ala |
| Leu | Ile, Val, Met, Ala |
| Lys | Arg, Gln, His |
| Met | Leu, Ile, Val, Ala, Phe |
| Phe | Met, Leu, Tyr, Trp, His |
| Ser | Thr, Cys, Ala |
| Thr | Ser, Val, Ala |
| Trp | Tyr, Phe |
| Tyr | Trp, Phe, His |
| Val | Ile, Leu, Met, Ala, Thr |

In an aspect, transgene expression for RD114TR-pseudotyped retroviral vector at about 10-day post-transduction is about 20% to about 60% about 30% to about 50%, or about 35% to about 45%. In an aspect, transgene expression for RD114TR-pseudotyped retroviral vector at 10-day post-transduction is about 20% to about 60% about 30% to about 50%, or about 35% to about 45% relative to transgene expression for VSV-G-pseudotyped vectors at day 10 post-transduction of about 5% to about 25%, about 2% to about 20%, about 3% to about 15%, or about 5% to about 12% under the same conditions. In yet another aspect, transgene expression for RD114TR-pseudotyped retroviral vector at 10-day post-transduction is about 40% relative to transgene expression for VSV-G-pseudotyped vectors at day 10 post-transduction of about 3.6%.

In yet another aspect, transgene expression for RD114TR-pseudotyped retroviral vector at about 5-day post-transduction is about 20% to about 50% about 15% to about 30%, or about 20% to about 30%. In an aspect, transgene expression for RD114TR-pseudotyped retroviral vector at 5-day post-transduction is about 20% to about 50% about 15% to about 30%, or about 20% to about 30% relative to transgene expression for VSV-G-pseudotyped vectors at day 5 post-transduction of about 10% to about 20%, about 15% to about 25%, or about 17.5% to about 20% under the same conditions. In yet another aspect, transgene expression for RD114TR-pseudotyped retroviral vector at 5-day post-transduction is about 24% relative to transgene expression for VSV-G-pseudotyped vectors at day 5 post-transduction of about 19%.

In another aspect, transgene expression for RD114TR-pseudotyped retroviral vector at 10-day post-transduction is about 2 times, about 3 times, about 4 times, about 5 times, or about 10 times, about 11 times, or about 12 times or more relative to transgene expression for VSV-G-pseudotyped vectors at day 10 post-transduction.

In an aspect, the disclosure provides for methods of using retrovirus with RD114TR pseudotype (for example, SEQ ID NO: 1) to transduce T cells. In another aspect, T cells are more efficiently transduced by retrovirus with RD114TR pseudotype (for example, SEQ ID NO: 1) as compared to retrovirus with VSV-G pseudotype (for example, SEQ ID NO: 3). In another aspect, a RD114TR envelope is utilized to pseudotype a lentivector, which is then used to transduce T cells with excellent efficiency.

Engineered γδ T-cells may be generated with various methods. For example, a polynucleotide encoding an expression cassette that comprises a tumor recognition, or another type of recognition moiety, can be stably introduced into the γδ T-cell by a transposon/transposase system or a viral-based gene transfer system, such as a lentiviral or a retroviral system, or another suitable method, such as transfection, electroporation, transduction, lipofection, calcium phosphate ($CaPO_4$), nanoengineered substances, such as Ormosil, viral delivery methods, including adenoviruses, retroviruses, lentiviruses, adeno-associated viruses, or another suitable method. A number of viral methods have been used for human gene therapy, such as the methods described in WO 1993020221, which is incorporated herein in its entirety. Non-limiting examples of viral methods that can be used to engineer γδ T cells may include γ-retroviral, adenoviral, lentiviral, herpes simplex virus, vaccinia virus, pox virus, or adeno-virus associated viral methods.

FIG. 14 shows the activated T cells may be engineered by transducing with a viral vector, such as RD114TR γ-retroviral vector and RD114TR lentiviral vector, expressing exogenous genes of interest, such as αβ TCRs against specific cancer antigen and CD8, into isolated γδ T cells. Viral vectors may also contain post-transcriptional regulatory element (PRE), such as Woodchuck PRE (WPRE) to enhance the expression of the transgene by increasing both nuclear and cytoplasmic mRNA levels. One or more regulatory elements including mouse RNA transport element (RTE), the constitutive transport element (CTE) of the simian retrovirus type 1 (SRV-1), and the 5' untranslated region of the human heat shock protein 70 (Hsp70 5'UTR) may also be used and/or in combination with WPRE to increase transgene expression. Transduction may be carried out once or multiple times to achieve stable transgene expression in small scale, e.g., 24 to 4-6 well plates, or mid/large scale for ½-5 days, e.g., 1 day.

RD114TR is a chimeric glycoprotein containing an extracellular and transmembrane domain of feline endogenous virus (RD114) fused to cytoplasmic tail (TR) of murine leukemia virus. In an aspect, transgene expression for RD114TR-pseudotyped retroviral vector at 10-day post-transduction is higher relative to VSV-G-pseudotyped vectors.

Other viral envelop proteins, such as VSV-G env, MLV 4070 env, RD114 env, chimeric envelope protein RD114pro, baculovirus GP64 env, or GALV env, or derivatives thereof, may also be used.

In an aspect, engineered (or transduced) γδ T cells can be expanded ex vivo without stimulation by an antigen presenting cell or aminobisphosphonate. Antigen reactive engineered T cells of the present disclosure may be expanded ex vivo and in vivo. In another aspect, an active population of engineered γδ T cells of the present disclosure may be expanded ex vivo without antigen stimulation by an antigen presenting cell, an antigenic peptide, a non-peptide molecule, or a small molecule compound, such as an aminobisphosphonate but using certain antibodies, cytokines, mitogens, or fusion proteins, such as IL-17 Fc fusion, MICA Fc fusion, and CD70 Fc fusion. Examples of antibodies that can be used in the expansion of a γδ T-cell population may include anti-CD3, anti-CD27, anti-CD30, anti-CD70, anti-OX40, anti-NKG2D, or anti-CD2 antibodies, examples of cytokines may include IL-2, IL-15, IL-12, IL-21, IL-18, IL-9, IL-7, and/or IL-33, and examples of mitogens may include CD70 the ligand for human CD27, phytohaemagglutinin (PHA), concavalin A (ConA), pokeweed mitogen (PWM), protein peanut agglutinin (PNA), soybean agglutinin (SBA), *lens culinaris* agglutinin (LCA), *Pisum sativum* agglutinin (PSA), h *pomatia* agglutinin (HPA), *vicia graminea* Lectin (VGA) or another suitable mitogen capable of stimulating T-cell proliferation. In another aspect, a population of engineered γδ T cells can be expanded in less than 60 days, less than 48 days, 36 days, less than 24 days, less than 12 days, or less than 6 days.

In another aspect, the present disclosure provides methods for the ex vivo expansion of a population of engineered γδ T-cells for adoptive transfer therapy. Engineered γδ T cells of the disclosure may be expanded ex vivo. Engineered γδ T cells of the disclosure can be expanded in vitro without activation by APCs, or without co-culture with APCs, and aminophosphates.

In another aspect, a γδ T-cell population can be expanded in vitro in fewer than 36 days, fewer than 35 days, fewer than 34 days, fewer than 33 days, fewer than 32 days, fewer than 31 days, fewer than 30 days, fewer than 29 days, fewer than 28 days, fewer than 27 days, fewer than 26 days, fewer than 25 days, fewer than 24 days, fewer than 23 days, fewer than 22 days, fewer than 21 days, fewer than 20 days, fewer than 19 days, fewer than 18 days, fewer than 17 days, fewer than 16 days, fewer than 15 days, fewer than 14 days, fewer than 13 days, fewer than 12 days, fewer than 11 days, fewer than 10 days, fewer than 9 days, fewer than 8 days, fewer than 7 days, fewer than 6 days, fewer than 5 days, fewer than 4 days, or fewer than 3 days.

FIG. 14 shows expansion of the transduced or engineered γδ T cells may be carried out in the presence of cytokines, e.g., IL-2, IL-15, IL-18, and others, in small/mid-scale, e.g., flasks/G-Rex, or in large scale, e.g., 50 ml-100-liter bags, for 7-35 days, e.g., 14-28 days. The expanded transduced T cell products may then be cryopreserved as "off-the-shelf" T-cell products for infusion into patients.

Methods of Treatment

Compositions containing engineered γδ T cells described herein may be administered for prophylactic and/or therapeutic treatments. In therapeutic applications, pharmaceutical compositions can be administered to a subject already suffering from a disease or condition in an amount sufficient to cure or at least partially arrest the symptoms of the disease or condition. An engineered γδ T-cell can also be administered to lessen a likelihood of developing, contracting, or worsening a condition. Effective amounts of a population of engineered γδ T-cells for therapeutic use can vary based on the severity and course of the disease or condition, previous therapy, the subject's health status, weight, and/or response to the drugs, and/or the judgment of the treating physician.

Engineered γδ T cells of the present disclosure can be used to treat a subject in need of treatment for a condition, for example, a cancer described herein.

A method of treating a condition (e.g., ailment) in a subject with γδ T cells may include administering to the subject a therapeutically-effective amount of engineered γδ T cells. γδ T cells of the present disclosure may be administered at various regimens (e.g., timing, concentration, dosage, spacing between treatment, and/or formulation). A subject can also be preconditioned with, for example, chemotherapy, radiation, or a combination of both, prior to receiving engineered γδ T cells of the present disclosure. A population of engineered γδ T cells may also be frozen or cryopreserved prior to being administered to a subject. A population of engineered γδ T cells can include two or more cells that express identical, different, or a combination of identical and different tumor recognition moieties. For instance, a population of engineered γδ T-cells can include several distinct engineered γδ T cells that are designed to recognize different antigens, or different epitopes of the same antigen.

γδ T cells of the present disclosure may be used to treat various conditions. In an aspect, engineered γδ T cells of the present disclosure may be used to treat a cancer, including solid tumors and hematologic malignancies. Non-limiting examples of cancers include: acute lymphoblastic leukemia, acute myeloid leukemia, adrenocortical carcinoma, AIDS-related cancers, AIDS-related lymphoma, anal cancer, appendix cancer, astrocytomas, neuroblastoma, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, Merkel cell skin carcinoma, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenstrom's macroglobulinemia, and Wilms tumor.

In an aspect, engineered γδ T cells of the present disclosure may be used to treat an infectious disease. In another aspect, engineered γδ T cells of the present disclosure may be used to treat an infectious disease, an infectious disease may be caused a virus. In yet another aspect, engineered γδ T cells of the present disclosure may be used to treat an immune disease, such as an autoimmune disease.

Treatment with γδ T cells of the present disclosure may be provided to the subject before, during, and after the clinical onset of the condition. Treatment may be provided to the subject after 1 day, 1 week, 6 months, 12 months, or 2 years after clinical onset of the disease. Treatment may be provided to the subject for more than 1 day, 1 week, 1 month, 6 months, 12 months, 2 years, 3 years, 4 years, 5 years, 6 years, 7 years, 8 years, 9 years, 10 years or more after clinical onset of disease. Treatment may be provided to the subject for less than 1 day, 1 week, 1 month, 6 months, 12 months, or 2 years after clinical onset of the disease. Treatment may also include treating a human in a clinical trial. A treatment can include administering to a subject a pharmaceutical composition comprising engineered γδ T cells of the present disclosure.

In another aspect, administration of engineered γδ T cells of the present disclosure to a subject may modulate the activity of endogenous lymphocytes in a subject's body. In another aspect, administration of engineered γδ T cells to a subject may provide an antigen to an endogenous T-cell and may boost an immune response. In another aspect, the memory T cell may be a CD4+ T-cell. In another aspect, the memory T cell may be a CD8+ T-cell. In another aspect, administration of engineered γδ T cells of the present disclosure to a subject may activate the cytotoxicity of another immune cell. In another aspect, the other immune cell may be a CD8+ T-cell. In another aspect, the other immune cell may be a Natural Killer T-cell. In another aspect, administration of engineered γδ T-cells of the present disclosure to a subject may suppress a regulatory T-cell. In another aspect, the regulatory T-cell may be a FOX3+ Treg cell. In another aspect, the regulatory T-cell may be a FOX3 Treg cell. Non-limiting examples of cells whose activity can be modulated by engineered γδ T cells of the disclosure may include: hematopoietic stem cells; B cells; CD4; CD8; red blood cells; white blood cells; dendritic cells, including dendritic antigen presenting cells; leukocytes; macrophages; memory B cells; memory T-cells; monocytes; natural killer cells; neutrophil granulocytes; T-helper cells; and T-killer cells.

During most bone marrow transplants, a combination of cyclophosphamide with total body irradiation may be conventionally employed to prevent rejection of the hematopoietic stem cells (HSC) in the transplant by the subject's immune system. In an aspect, incubation of donor bone marrow with interleukin-2 (IL-2) ex vivo may be performed to enhance the generation of killer lymphocytes in the donor marrow. Interleukin-2 (IL-2) is a cytokine that may be necessary for the growth, proliferation, and differentiation of wild-type lymphocytes. Current studies of the adoptive transfer of γδ T-cells into humans may require the co-administration of γδ T-cells and interleukin-2. However, both low- and high-dosages of IL-2 can have highly toxic side effects. IL-2 toxicity can manifest in multiple organs/systems, most significantly the heart, lungs, kidneys, and central nervous system. In another aspect, the disclosure provides a method for administrating engineered γδ T cells to a subject without the co-administration of a native cytokine or modified versions thereof, such as IL-2, IL-15, IL-12, IL-21. In another aspect, engineered γδ T cells can be administered to a subject without co-administration with IL-2. In another aspect, engineered γδ T cells may be administered to a subject during a procedure, such as a bone marrow transplant without the co-administration of IL-2.

Methods of Administration

One or multiple engineered γδ T cell populations may be administered to a subject in any order or simultaneously. If simultaneously, the multiple engineered γδ T cell can be provided in a single, unified form, such as an intravenous injection, or in multiple forms, for example, as multiple intravenous infusions, s.c, injections or pills. Engineered γδ T-cells can be packed together or separately, in a single package or in a plurality of packages. One or all of the engineered γδ T cells can be given in multiple doses. If not simultaneous, the timing between the multiple doses may vary to as much as about a week, a month, two months, three months, four months, five months, six months, or about a year. In another aspect, engineered γδ T cells can expand within a subject's body, in vivo, after administration to a subject. Engineered γδ T cells can be frozen to provide cells for multiple treatments with the same cell preparation. Engineered γδ T cells of the present disclosure, and pharmaceutical compositions comprising the same, can be packaged as a kit. A kit may include instructions (e.g., written instructions) on the use of engineered γδ T cells and compositions comprising the same.

In another aspect, a method of treating a cancer comprises administering to a subject a therapeutically-effective amount of engineered γδ T cells, in which the administration treats the cancer. In another embodiments, the therapeutically-effective amount of engineered γδ T cells may be administered for at least about 10 seconds, 30 seconds, 1 minute, 10 minutes, 30 minutes, 1 hour, 2 hours, 3 hours, 4 hours, 5 hours, 6 hours, 12 hours, 24 hours, 2 days, 3 days, 4 days, 5 days, 6 days, 1 week, 2 weeks, 3 weeks, 1 month, 2 months, 3 months, 4 months, 5 months, 6 months, or 1 year. In another aspect, the therapeutically-effective amount of the engineered γδ T cells may be administered for at least one week. In another aspect, the therapeutically-effective amount of engineered γδ T cells may be administered for at least two weeks.

Engineered γδ T-cells described herein can be administered before, during, or after the occurrence of a disease or condition, and the timing of administering a pharmaceutical composition containing an engineered γδ T-cell can vary. For example, engineered γδ T cells can be used as a prophylactic and can be administered continuously to subjects with a propensity to conditions or diseases in order to lessen a likelihood of the occurrence of the disease or condition. Engineered γδ T-cells can be administered to a subject during or as soon as possible after the onset of the symptoms. The administration of engineered γδ T cells can be initiated immediately within the onset of symptoms, within the first 3 hours of the onset of the symptoms, within the first 6 hours of the onset of the symptoms, within the first 24 hours of the onset of the symptoms, within 48 hours of the onset of the symptoms, or within any period of time from the onset of symptoms. The initial administration can be via any route practical, such as by any route described herein using any formulation described herein. In another aspect, the administration of engineered γδ T cells of the present disclosure may be an intravenous administration. One or multiple dosages of engineered γδ T cells can be administered as soon as is practicable after the onset of a cancer, an infectious disease, an immune disease, sepsis, or with a bone marrow transplant, and for a length of time necessary for the treatment of the immune disease, such as, for example, from about 24 hours to about 48 hours, from about 48 hours to about 1 week, from about 1 week to about 2 weeks, from about 2 weeks to about 1 month, from about 1 month to about 3 months. For the treatment of cancer, one or multiple dosages of engineered γδ T cells can be administered years after onset of the cancer and before or after other treatments. In another aspect, engineered γδ T cells can be administered for at least about 10 minutes, 30 minutes, 1 hour, 2 hours, 3 hours, 4 hours, 5 hours, 6 hours, 12 hours, 24 hours, at least 48 hours, at least 72 hours, at least 96 hours, at least 1 week, at least 2 weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 1 year, at least 2 years at least 3 years, at least 4 years, or at least 5 years. The length of treatment can vary for each subject.

Preservation

In an aspect, γδ T cells may be formulated in freezing media and placed in cryogenic storage units such as liquid nitrogen freezers (−196° C.) or ultra-low temperature freezers (−65° C., 80° C., 120° C., or −150° C.) for long-term storage of at least about 1 month, 2 months, 3 months, 4 months, 5 months, 6 months, 1 year, 2 years, 3 years, or at least 5 years. The freeze media can contain dimethyl sulfoxide (DMSO), and/or sodium chloride (NaCl), and/or dextrose, and/or dextran sulfate and/or hydroxyethyl starch (HES) with physiological pH buffering agents to maintain pH between about 6.0 to about 6.5, about 6.5 to about 7.0, about 7.0 to about 7.5, about 7.5 to about 8.0 or about 6.5 to about 7.5. The cryopreserved γδ T cells can be thawed and further processed by stimulation with antibodies, proteins, peptides, and/or cytokines as described herein. The cryopreserved γδ T-cells can be thawed and genetically modified with viral vectors (including retroviral, adeno-associated virus (AAV), and lentiviral vectors) or non-viral means (including RNA, DNA, e.g., transposons, and proteins) as described herein. The modified γδ T cells can be further cryopreserved to generate cell banks in quantities of at least about 1, 5, 10, 100, 150, 200, 500 vials at about at least 101, 102, 103, 104, 105, 106, 107, 108, 109, or at least about 1010 cells per mL in freeze media. The cryopreserved cell banks may retain their functionality and can be thawed and further stimulated and expanded. In another aspect, thawed cells can be stimulated and expanded in suitable closed vessels, such as cell culture bags and/or bioreactors, to generate quantities of cells as allogeneic cell product. Cryopreserved γδ T cells can maintain their biological functions for at least about 6 months, 7 months, 8 months, 9 months, 10 months, 11 months, 12 months, 13 months, 15 months, 18 months, 20 months, 24 months, 30 months, 36 months, 40 months, 50 months, or at least about 60 months under cryogenic storage condition. In another aspect, no preservatives may be used in the formulation. Cryopreserved γδ T-cells can be thawed and infused into multiple patients as allogeneic off-the-shelf cell product.

In an aspect, engineered γδ T-cell described herein may be present in a composition in an amount of at least $1\times10^3$ cells/ml, at least $2\times10^3$ cells/ml, at least $3\times10^3$ cells/ml, at least $4\times10^3$ cells/ml, at least $5\times10^3$ cells/ml, at least $6\times10^3$ cells/ml, at least $7\times10^3$ cells/ml, at least $8\times10^3$ cells/ml, at least $9\times10^3$ cells/ml, at least $1\times10^4$ cells/ml, at least $2\times10^4$ cells/ml, at least $3\times10^4$ cells/ml, at least $4\times10^4$ cells/ml, at least $5\times10^4$ cells/ml, at least $6\times10^4$ cells/ml, at least $7\times10^4$ cells/ml, at least $8\times10^4$ cells/ml, at least $9\times10^4$ cells/ml, at least $1\times10^5$ cells/ml, at least $2\times10^5$ cells/ml, at least $3\times10^5$ cells/ml, at least $4\times10^5$ cells/ml, at least $5\times10^5$ cells/ml, at least $6\times10^5$ cells/ml, at least $7\times10^5$ cells/ml, at least $8\times10^5$ cells/ml, at least $9\times10^5$ cells/ml, at least $1\times10^6$ cells/ml, at least $2\times10^6$ cells/ml, at least $3\times10^6$ cells/ml, at least $4\times10^6$ cells/ml, at least $5\times10^6$ cells/ml, at least $6\times10^6$ cells/ml, at least $7\times10^6$ cells/ml, at least $8\times10^6$ cells/ml, at least $9\times10^6$ cells/ml, at least $1\times10^7$ cells/ml, at least $2\times10^7$ cells/ml, at least $3\times10^7$ cells/ml, at least $4\times10^7$ cells/ml, at least $5\times10^7$ cells/ml, at least $6\times10^7$ cells/ml, at least $7\times10^7$ cells/ml, at least $8\times10^7$ cells/ml, at least $9\times10^7$ cells/ml, at least $1\times10^8$ cells/ml, at least $2\times10^8$ cells/ml, at least $3\times10^8$ cells/ml, at least $4\times10^8$ cells/ml, at least $5\times10^8$ cells/ml, at least $6\times10^8$ cells/ml, at least $7\times10^8$ cells/ml, at least $8\times10^8$ cells/ml, at least $9\times10^8$ cells/ml, at least $1\times10^9$ cells/ml, or more, from about $1\times10^3$ cells/ml to about at least $1\times10^8$ cells/ml, from about $1\times10^5$ cells/ml to about at least $1\times10^8$ cells/ml, or from about $1\times10^6$ cells/ml to about at least $1\times10^8$ cells/ml.

To develop viable allogeneic T cell products, e.g., that can be engineered to express tumor antigen specific TCR, e.g., chimeric CD8α-CD4tm/intracellular protein (FIGS. 12A and 12B), embodiments of the present disclosure may include methods that can maximize the yield of γδ T cells while minimizing the presence of residual αβ T cells in the final allogeneic products. For example, embodiments of the present disclosure may include methods of expanding and activating γδ T cells by depleting αβ T cells and supplementing the growth culture with molecules, such as Amphotericin B, N-acetyl cysteine (NAC) (or high dose glutamine/glutamax), IL-2, and/or IL-15.

In an aspect, methods described herein may be used to produce autologous or allogenic products according to an aspect of the disclosure.

The present invention may be better understood by reference to the following examples, which are not intended to limit the scope of the claims.

EXAMPLES

Example 1

Processing a Leukapheresis Product

A leukapheresis product, e.g., LeukoPak®, may be processed as follows: one end of a LeukoPak® bag may be swabbed with alcohol swab and cut with razor blade to drain into a flask. The volume may be diluted to between approximately 500 ml with Hank's solution and then aliquoted into 16-29 tubes with 50 ml capacity, 30 ml per tube. The tubes may be spun at 400 g for 30 minutes with no brake and no acceleration. White liquid may be aspirated, and new 50 ml tubes may be filled up halfway and topped off with 25 ml PBS. This procedure may be repeated 2 additional times for a total of 3 washes. Cells may be counted before the last wash using a hemocytometer. The yield may be between 30-60 tubes of $1\times10^8$ cells/tube.

Example 2

Depleting αβ T cells

Figure 1A:
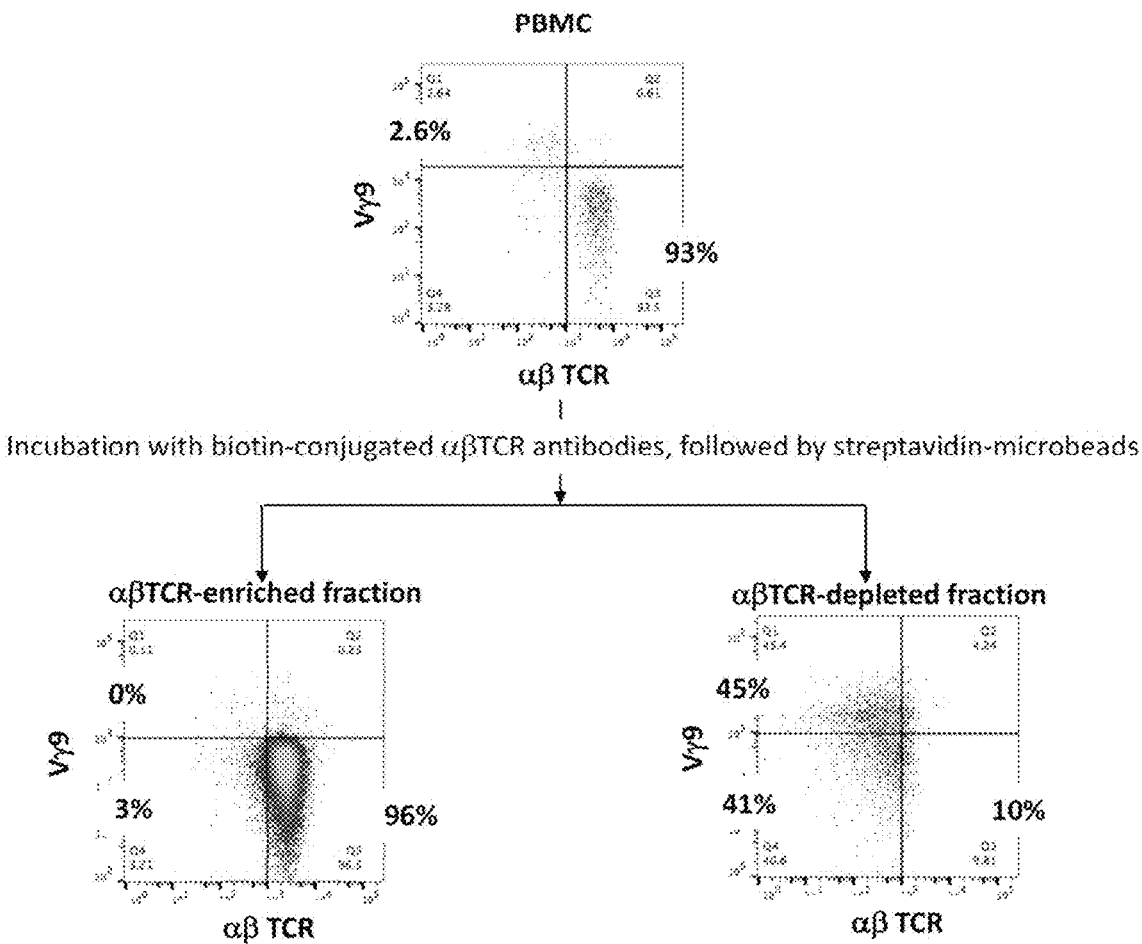
FIG. 1A shows depletion of αβ T cells from PBMC according to an embodiment of the disclosure. PBMCs were incubated with biotin-conjugated αβ TCR antibodies, followed by streptavidin-microbeads per manufacturer protocol. Samples were then passed through LS column to enrich for αβ TCR-expressing cells. The column flow-through represents the αβ TCR depleted fractions. After overnight culture, the αβ TCR-enriched fraction and the αβ TCR-depleted fraction were stained with fluorochrome-conjugated αβ TCR antibody versus Vγ9 antibody, followed by flow cytometry analysis.

FIG. 1A shows depletion of αβ T cells from PBMC. Post-ficolled PBMCs were incubated with biotin-conjugated αβ TCR antibodies, followed by streptavidin-microbeads per manufacturer protocol. Samples were then passed through a LS column to enrich for αβ TCR-expressing cells. The column flow-through represents the αβ TCR depleted fractions. After overnight culture, the αβ TCR-enriched fractions and the αβ TCR-depleted fractions were stained with fluorochrome-conjugated αβ TCR antibody versus Vγ9 antibody, followed by flow cytometry analysis. The data shows, while the αβ TCR-enriched fractions contains almost none (0%) Vγ9δ2 cells, almost all Vγ9δ2 cells are enriched (45%) in the αβ TCR-depleted fractions.

Similarly, cells from leukapheresis product may be incubated with biotin-conjugated αβ TCR antibodies, followed by streptavidin-microbeads per manufacturer protocol. Samples were then passed through LS column to enrich for αβ TCR-expressing cells. The column flow-through represents the αβ TCR depleted fractions. After overnight culture, the αβ TCR-depleted fractions were stained with fluorochrome-conjugated αβ TCR antibody versus γδ TCR antibody, followed by flow cytometry analysis. FIG. 1E shows, while the starting cells in leukapheresis product contain minimum (4.14%) Vγ9δ2 cells, almost all Vγ9δ2 cells are enriched (95.5%) in the αβ TCR-depleted fractions. In an aspect, using the afore-mentioned methods, Vγ9δ2 cells may be enriched more than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, 91%, 92%, 93%, 94%, 95%, 96%, 97%, 98%, or 99%.

Figure 1B:
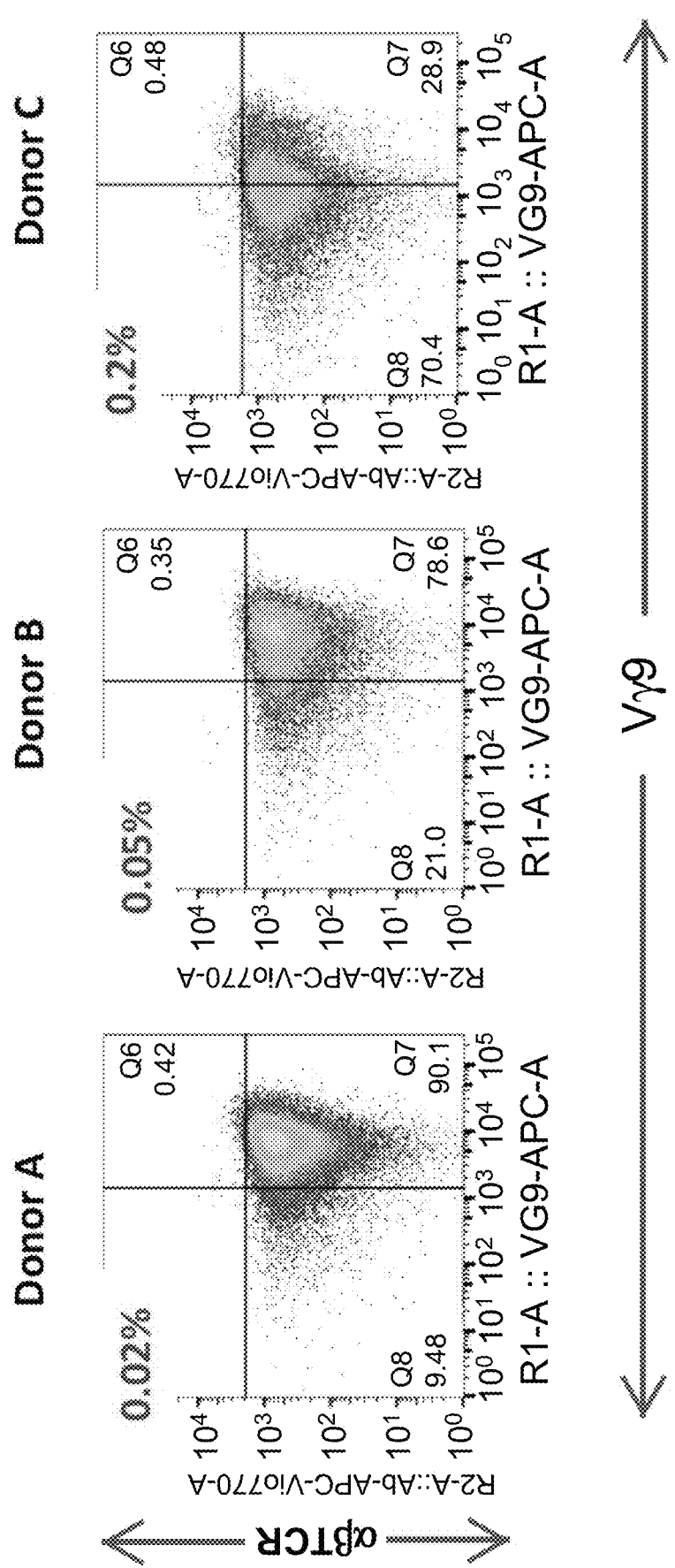
FIGS. 1B and 1C show minimal residual αβ T cells in Vγ9δ2 T cell product according to an embodiment of the disclosure. αβ T cells were depleted from PBMC of normal donors (Donor A, Donor B, and Donor C) (FIG. 1B) and (Donor 12 and Donor 13) (FIG. 1C) using commercially available biotinylated anti-αβ TCR antibody/streptavidin microbeads. αβ T cell-depleted PBMC were cultured with zoledronate/IL-2/IL-15 for 14 days, followed by cell surface staining with respective fluorochrome conjugated antibodies, e.g., anti-αβ TCR antibodies and anti-γδ TCR antibodies to assess for residual αβ T cells and enriched γδ T cells by sub-gating on CD3.
Figure 1C:
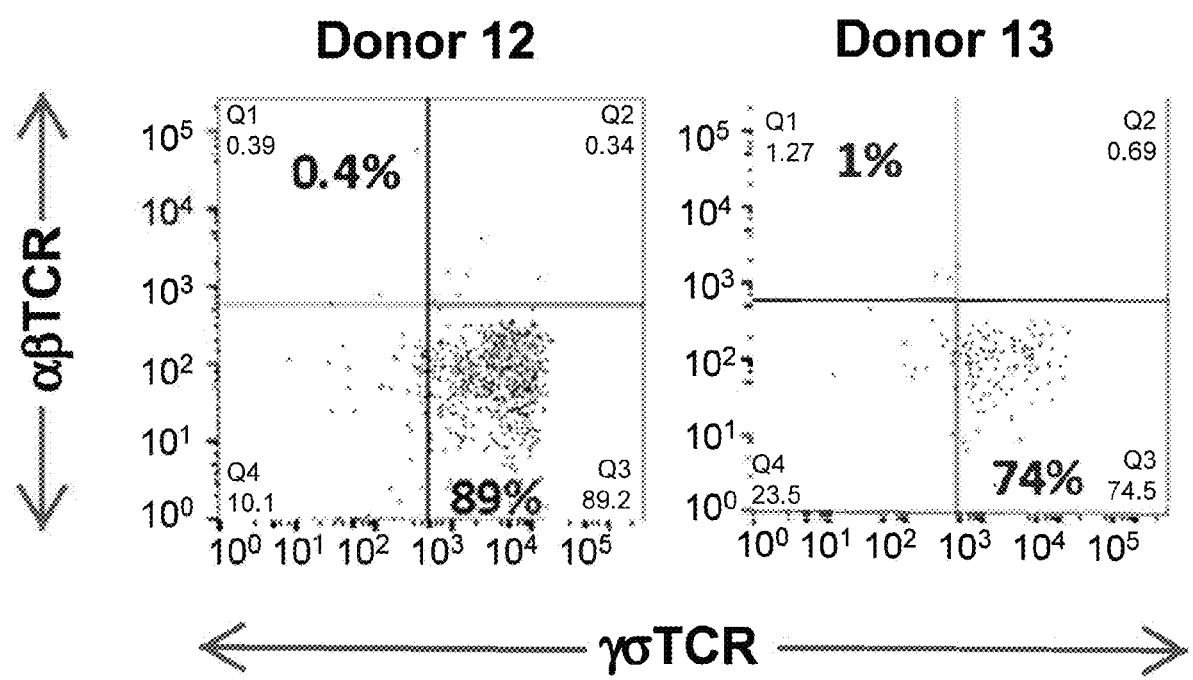

FIGS. 1B and 1C show minimal residual αβ T cells in Vγ9δ2T cell product. αβ T cells were depleted from PBMC of normal donors (Donor A, Donor B, Donor C, Donor 12, and Donor 13) using biotinylated anti-αβ TCR antibody/streptavidin microbeads. αβ T cell-depleted PBMC were cultured with zoledronate/IL-2/IL-15 for 14 days, followed by cell surface staining with respective fluorochrome conjugated antibodies, e.g., anti-αβ TCR antibodies and anti-γδ TCR antibodies to assess for residual αβ T cells and enriched γδ T cells by sub-gating on CD3. These results show αβ T cell-depleted γδ T cells were enriched, i.e., 90.1% (Donor A), 78.6% (Donor B), 28.9% (Donor C), 89% (Donor 12), and 74% (Donor 13). In addition, αβ T cell-depleted γδ T cells contain minimal residual αβ T cells, i.e., 0.02% (Donor A), 0.05% (Donor B), 0.2% (Donor C), 0.4% (Donor 12), and 1% (Donor 13). Minimal residual αβ T cells is important because, for example, in haploidentical hematopoietic stem cell transplantation (HSCT), residual αβ T cells ranging from 0.2-0.6% did not result in chronic graft versus host disease (GVHD), thus, making these αβ T cell-depleted γδ T cells safe allogeneic products.

Figure 1D:
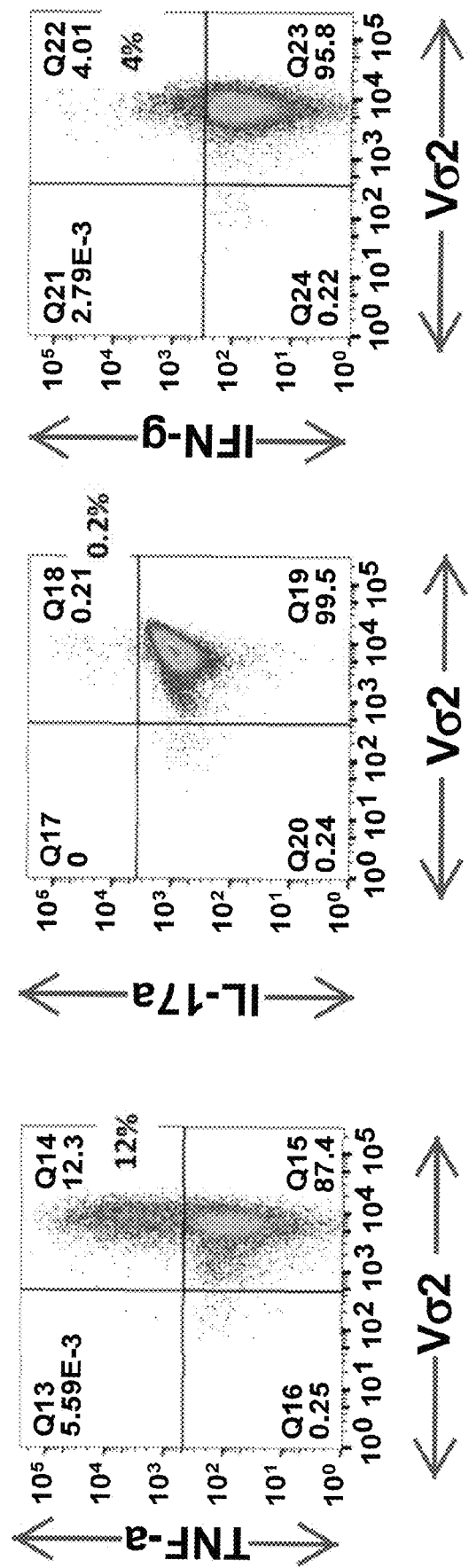
FIG. 1D shows cytokine profiling of Vγ9δ2 T cells according to an embodiment of the disclosure. Vγ9δ2 cells were treated with Golgi Stop/Plug (i.e., protein transport inhibitors) for 6 hours prior to cell harvest. Cells were stained for surface Vδ2 followed by fixation and permeabilization. Staining intracellular TNF-α, IL-17a, and IFN-γ were performed using fluorochrome-conjugated antibodies against TNF-α, IL-17a, and IFN-γ.
Figure 1E:
FIG. 1E shows depletion of αβ T cells from a leukapheresis product, e.g., LeukoPak®, according to another embodiment of the disclosure. White blood cells including dendritic and progenitor cells from leukapheresis product may be incubated with biotin-conjugated αβ TCR antibodies, followed by streptavidin-microbeads. Samples were then passed through LS column to enrich for αβ TCR-expressing cells. The column flow-through represents the αβ TCR depleted fractions. After overnight culture, the αβ TCR-depleted fractions were stained with fluorochrome-conjugated αβ TCR antibody versus γδ TCR antibody, followed by flow cytometry analysis

FIG. 1D shows cytokine profiling of Vγ9δ2 cells. αβ T cell-depleted PBMC cultured with zoledronate/IL-2/IL-15 were treated with Golgi Stop/Plug (i.e., protein transport inhibitors) for 6 hours prior to cell harvest. Cells were stained for surface Vδ2 followed by fixation and permeabilization. Staining intracellular TNF-α, IL-17a, and IFN-γ were performed using fluorochrome-conjugated antibodies against TNF-α, IL-17a, and IFN-γ. These results show TNF-α, IL-17a, and IFN-γ were expressed in 12%, 0.2%, and 4% of Vγ9δ2 cells, respectively. IL-15-mediated inhibition of IL-17 commitment is shown by low amount of IL-17-producing Vγ9δ2 T cells, e.g., 0.2%.

Example 3

Activation and Expansion of αβ T Cell-Depleted PBMC

Maximal T cell activation, proliferation, and survival without commitment to anergy may require three signals: signal 1 elicited through TCR, signal 2 elicited through co-stimulatory molecules, and signal 3 elicited through growth factor signaling.

Figure 2:
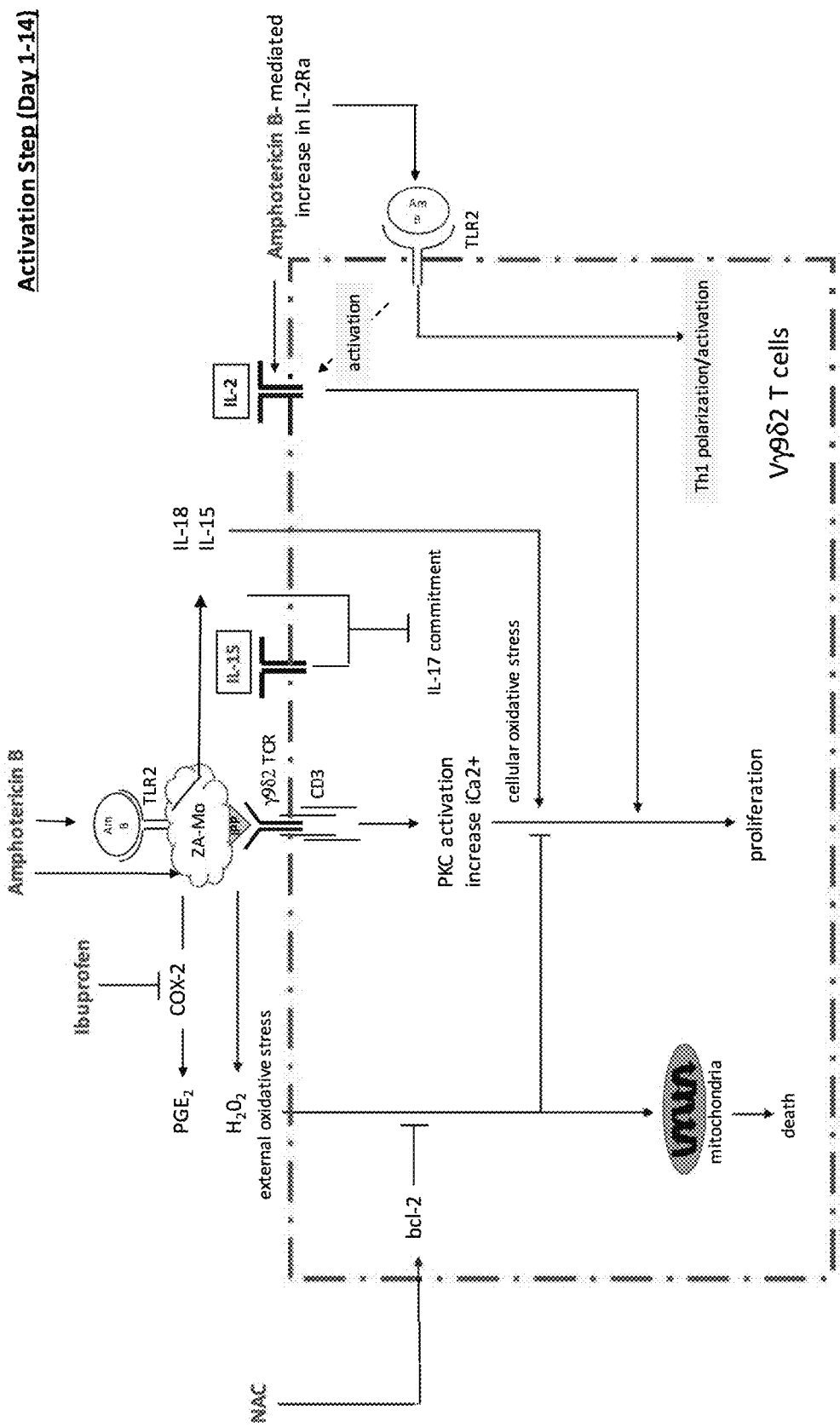
FIG. 2 shows effects of molecules on activation of Vγ9δ2 T cells according to an embodiment of the disclosure. During activation step, aminobisphosphonate, e.g., zoledronate (ZA), or phosphoantigen, e.g., IPP, and cytokines, e.g., IL-2 and/or IL-15, may be present.
Figure 3:
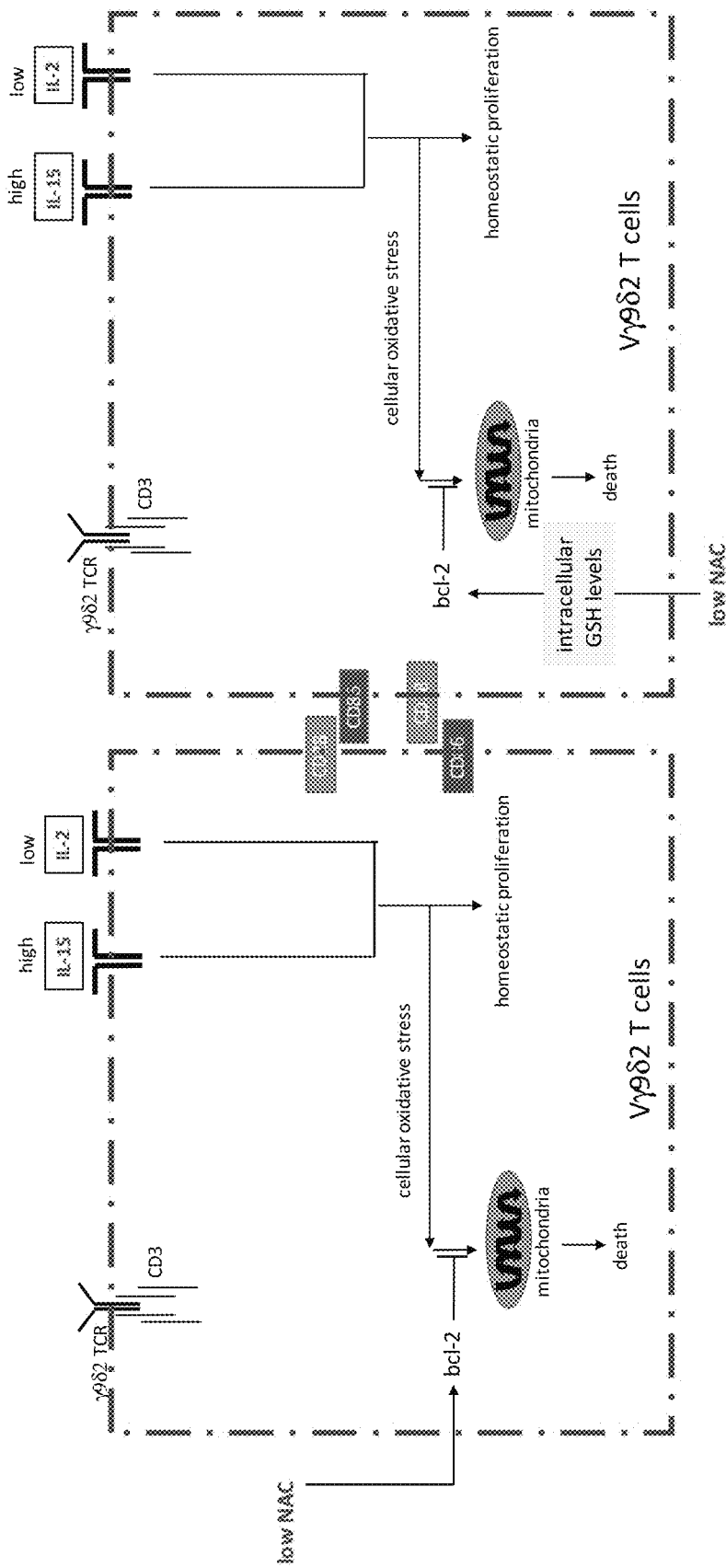
FIG. 3 shows effects of molecules on expansion of Vγ9δ2 T cells according to an embodiment of the disclosure. During expansion step, cytokines may continue to be present without aminobisphosphonate or phosphoantigen, IPP.

FIGS. 2 and 3 show, respectively, activation step and expansion step according to an embodiment of the present disclosure. Activation step and expansion step may be two sequential steps. For example, during activation step (FIG. 2), aminobisphosphonate, e.g., zoledronate (ZA), or phosphoantigen, e.g., IPP, and cytokines, e.g., IL-2 and/or IL-15, may be present. Whereas, during expansion step (FIG. 3), cytokines may continue to be present without aminobisphosphonate or phosphoantigen, e.g., IPP. Activation step (FIG. 2) may occur during the first 14 days, when aminobisphosphonate or phosphoantigen, e.g., IPP, is added and not washed off. Expansion step (FIG. 3) may be from Day 15 onward because, at the end of Day 14, activated cells may be collected by removing all medium, which contains aminobisphosphonate or phosphoantigen, e.g., IPP, and replace with medium with cytokines in the absence of aminobisphosphonate or phosphoantigen, e.g., IPP. In contrast, the conventional protocol for Vγ9δ2 zoledronate-mediated production often refers Day 1-14 as activation/expansion because, under such conditions, cells could not be kept alive beyond day 14. In the present disclosure, Day 1-14 is referred to activation step because aminobisphosphonate, e.g., zoledronate, or phosphoantigen, e.g., IPP, is present, and Day 15-onward is referred to as expansion step because cells can be kept alive and expanded beyond the conventional 14-day process.

FIG. 2 shows signal 1 elicited through γδ TCR/IPP interaction induced by aminobisphosphonate, which may include pamidronic acid, alendronic acid, zoledronic acid, risedronic acid, ibandronic acid, incadronic acid, a salt thereof and/or a hydrate thereof; or phosphoantigens, e.g., (E)-4-hydroxy-3-methyl-but-2-enyl pyrophosphate (HMBPP), isoprenoid pyrophosphates (farnesyl pyrophosphate (FPP), geranylgeranyl pyrophosphate (GGPP), isopentenyl pyrophosphate (IPP), and dimethylallyl diphosphate (DMAPP)), to activate Vγ9δ2 T cells for proliferation. For example, Zoledronate (Zoledronic acid (ZA) or Zometa) inhibits the mevalonate pathway in monocytes (Mo), leading to accumulation of phosphoantigens, such as IPP, displayed on monocytes (ZA-Mo) to activate γ9δ2 TCR/CD3 and induce proliferation via PKC signaling, thereby serving as signal 1. IPP per se can also act directly on γδ T cells by binding to γ9δ2 TCR, thereby obviating the need for monocytes.

FIG. 2 also shows signal 2 elicited through co-stimulatory molecules, such as Amphotericin B (FDA-approved Ambisome), i.e., a TLR2 ligand. For example, Amphotericin B can stimulate γδ T cells via two potential mechanisms. First, Amphotericin B, serving as signal 2, can act on γδ T cells as a costimulatory molecule to co-stimulate γδ T cell activation, proliferation, and IFN-γ production and to reduce the immunosuppressive activity of Vδ2 T cells on αβ T cells. Amphotericin B can also act as an enhancer of CD25, which is the high affinity receptor for IL-2 (IL-2Ra), thereby increasing responsiveness to IL-2 to stimulate proliferation via signal 3. Second, Amphotericin B, serving as signal 3, can act on monocyte (ZA-Mo) to promote secretion of IL-18, which can enhance CD25 expression and favor central memory T cells and to promote secretion of IL-15, which can enhance production of effector Vγ9δ2 T cells and blocking IL-17 committed cells. Suitable substitutes for Amphotericin B may include natural extracts, such as L-theanine from tea, tannin from apple, and polyphenols from cranberry and shitake mushrooms.

Supplementing Vγ9δ2 cultures with co-stimulatory molecules, such as CD86 and 41 BBL, enhanced their proliferation. Embodiments of the present disclosure may include use of αβ T cell depleted PBMCs or αβ T cell depleted leukapheresis product, in which myeloid cells may be the predominant cell population. Myeloid cells uptake Zoledronate, which inhibits the mevalonate pathway, leading to accumulation of IPP, which may be expressed as secreted form or presented as membrane bound form on myeloid cells. Myeloid cells are also excellent antigen presenting cells, expressing various co-stimulatory molecules at different stages of differentiation.

Furthermore, γδ T cells themselves may also express various co-stimulatory molecules. As such, αβ-depleted PBMCs or αβ T cell depleted leukapheresis product may be cultured at high cell density during Zoledronate treatment to facilitate engagement of co-stimulatory molecules present on myeloid cells as well as the expanding γδ T cells, thereby enhancing activation, proliferation, and survival of Vγ9δ2 T cells. For example, exogenous IL-2 (10-1000 U/ml, preferably 20-500 U/ml, more preferably 50-100 U/ml) may be added to αβ-depleted PBMCs or αβ T cell depleted leukapheresis product, in which CD4 helper T cells (to secrete IL-2) are among the αβ T cells depleted cells, to sustain survival and proliferation during activation and expansion. Exogenous IL-15 (10-1000 ng/ml, preferably 20-500 ng/ml; more preferably 50-100 ng/ml) may be used in high cell density culture to maximize Vγ9δ2 activation by inhibiting the development of IL-17-producing Vγ9δ2 T cells, as shown in FIG. 1D (middle panel), enhancing γδ T cell proliferation, and promoting the differentiation of naive Vγ9δ2 T cells to effector cells. High density culture, thus, exploits the reciprocal costimulatory action between γδ-γδ T cells, which express CD28, CD86, CD83, CD80 on γδ T cells. For example, CD28 costimulatory molecule, which interacts with CD86 and/or CD80, can enhance γδ T cells survival and proliferation.

Figure 4A:
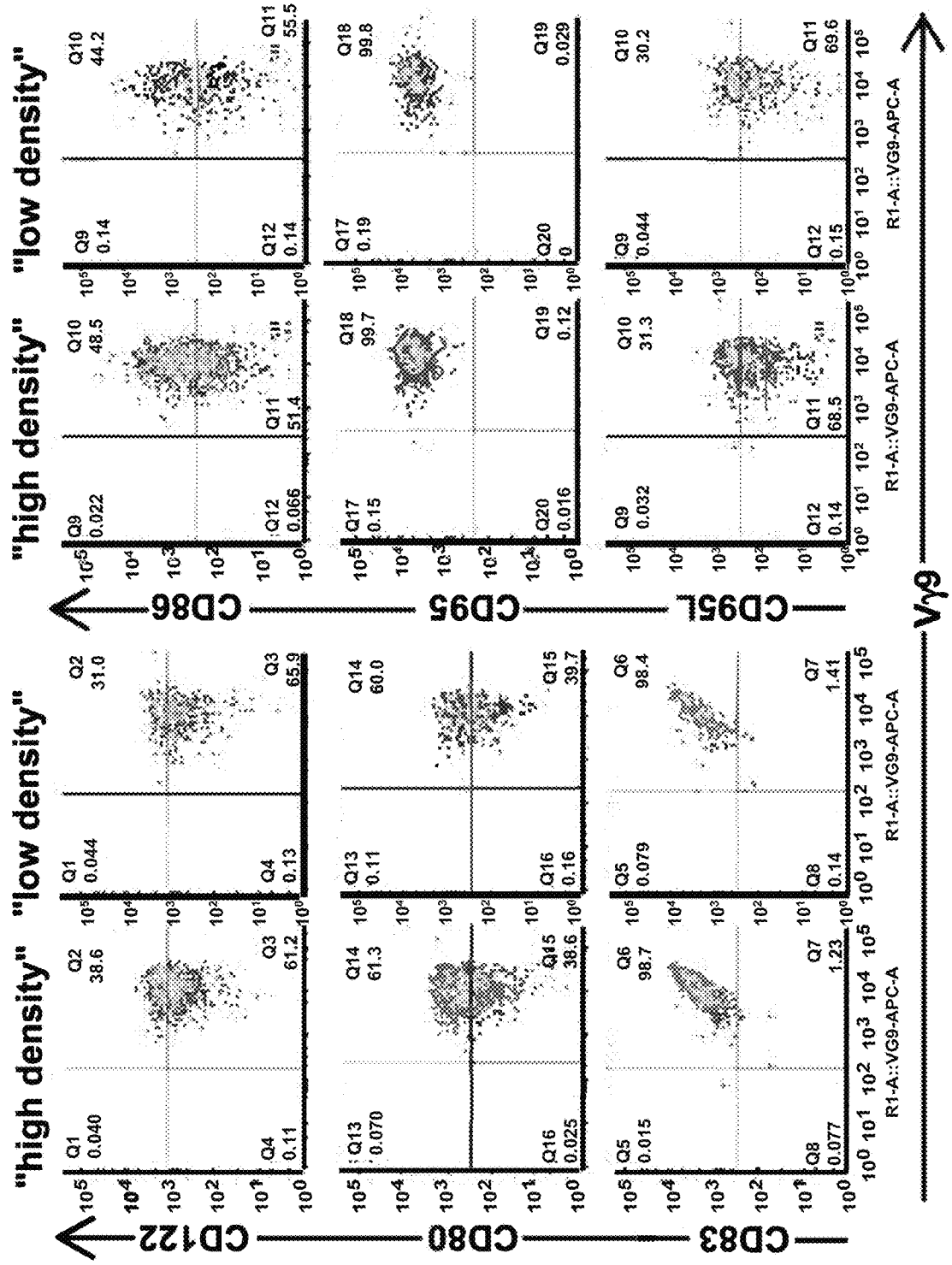
FIG. 4A shows effects of cell density on T cell markers during expansion according to an embodiment of the disclosure. After activation in the presence of zoledronate, IL-2, and IL-15 for 14 days, Vγ9δ2 T cells were expanded by homeostatic cytokines, e.g., IL-2 and IL-15, in the absence of zoledronate at high density (e.g., $2 \times 10^6$ cells/ml) and at low density (e.g., $0.5 \times 10^6$ cells/ml). T cell markers, e.g., CD122, CD80, CD83, CD86, CD95, and CD95L, were analyzed.
Figure 4B:
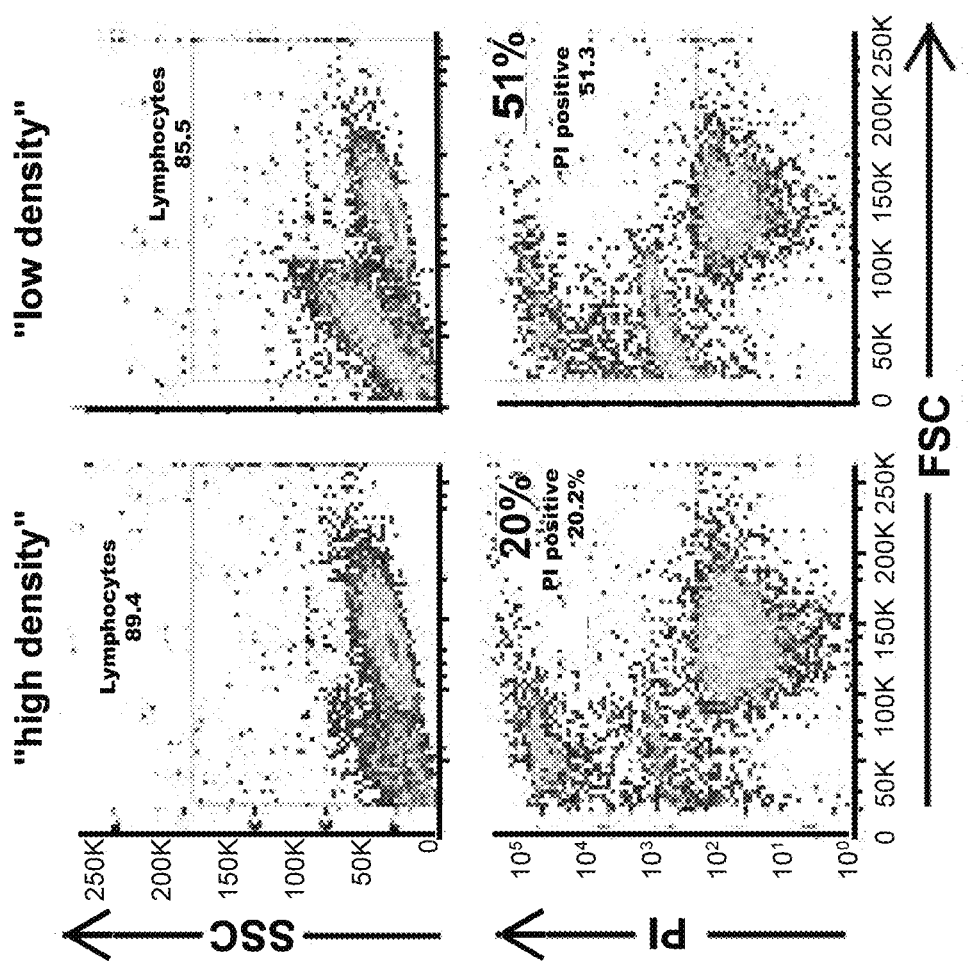
FIG. 4B shows effects of cell density on cell death during expansion according to an embodiment of the disclosure. After activation in the presence of zoledronate, IL-2, and IL-15 for 14 days, T cells were expanded by homeostatic cytokines, e.g., IL-2 and IL-15, in the absence of zoledronate at high density (e.g., $2 \times 10^6$ cells/ml) and at low density (e.g., $0.5 \times 10^6$ cells/ml). Cell death was measured.

To determine the effects of cell density on T cell phenotypes and cell death, after activation in the presence of zoledronate, IL-2, and IL-15 for 14 days, Vγ9δ2 T cells were expanded by homeostatic cytokines, e.g., IL-2 and IL-15, in the absence of zoledronate at high density (e.g., $2 \times 10^6$ cells/ml) and at low density (e.g., $0.5 \times 10^6$ cells/ml) followed by T cell marker analysis. FIG. 4A shows immunophenotyped markers, e.g., CD122, CD80, CD83, CD86, CD95, and CD95L, were not affected in Vγ9δ2 T cells by cell density as there is no significant difference between marker expressions in Vγ9δ2 T cells cultured at high density and at low density. However, FIG. 4B shows a significant reduction in cell death (20%) during expansion at high density as compared with that (51%) at low density. These results suggest that expanding Vγ9δ2 T cells at high density, e.g., at least $1 \times 10^6$ cells/ml, may promote cell survival by reducing cell death.

Figure 5:
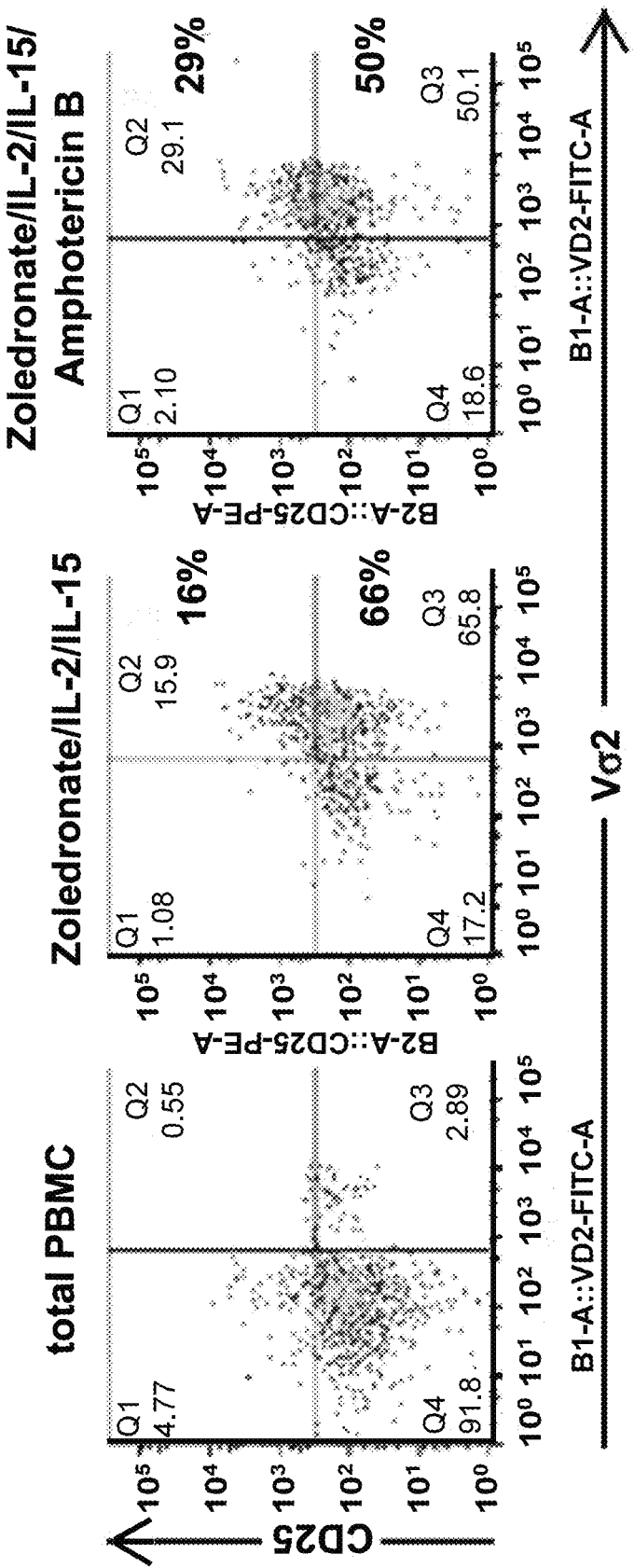
FIG. 5 shows effects of Amphotericin B on Vδ2 T cells expressing IL-2Rα according to an embodiment of the disclosure. αβ-depleted PBMCs were cultured in Activation Medium supplemented with Zoledronate, IL-2, and IL-15 on Day 0. After 48 hours, Amphotericin B was added and 48 hours later, cells were harvested for flow cytometry based analysis of CD25 (or IL-2Rα) surface expression on CD3$^+$/Vδ2 T cells.

FIG. 5 shows inclusion of Amphotericin B increases the % of Vδ2 (i.e., Vγ9δ2) T cells expressing CD25 (or IL-2Ra). Briefly, αβ-depleted PBMCs were cultured in Activation Medium supplemented with Zoledronate, IL-2, and IL-15 on Day 0. After 48 hours, Amphotericin B was added and 48 hours later, cells were harvested for flow cytometry-based analysis of CD25 (or IL-2Ra) surface expression on CD3+/Vδ2 T cells. These results show treatment of Zoledronate, IL-2, and IL-15 increases the % of CD25-expressing Vδ2 T cells to 16%, as compared with that of the untreated αβ-depleted PBMCs (0.55%). However, addition of Amphotericin B to Zoledronate, IL-2, and IL-15, increases the % of Vδ2 T cells from 16% (without Amphotericin B) to 29% (with Amphotericin B). These results show that Amphotericin B can further expand Vδ2 T cells expanded and activated by Zoledronate, IL-2, and IL-15, via signals 2 and 3.

Figure 6:
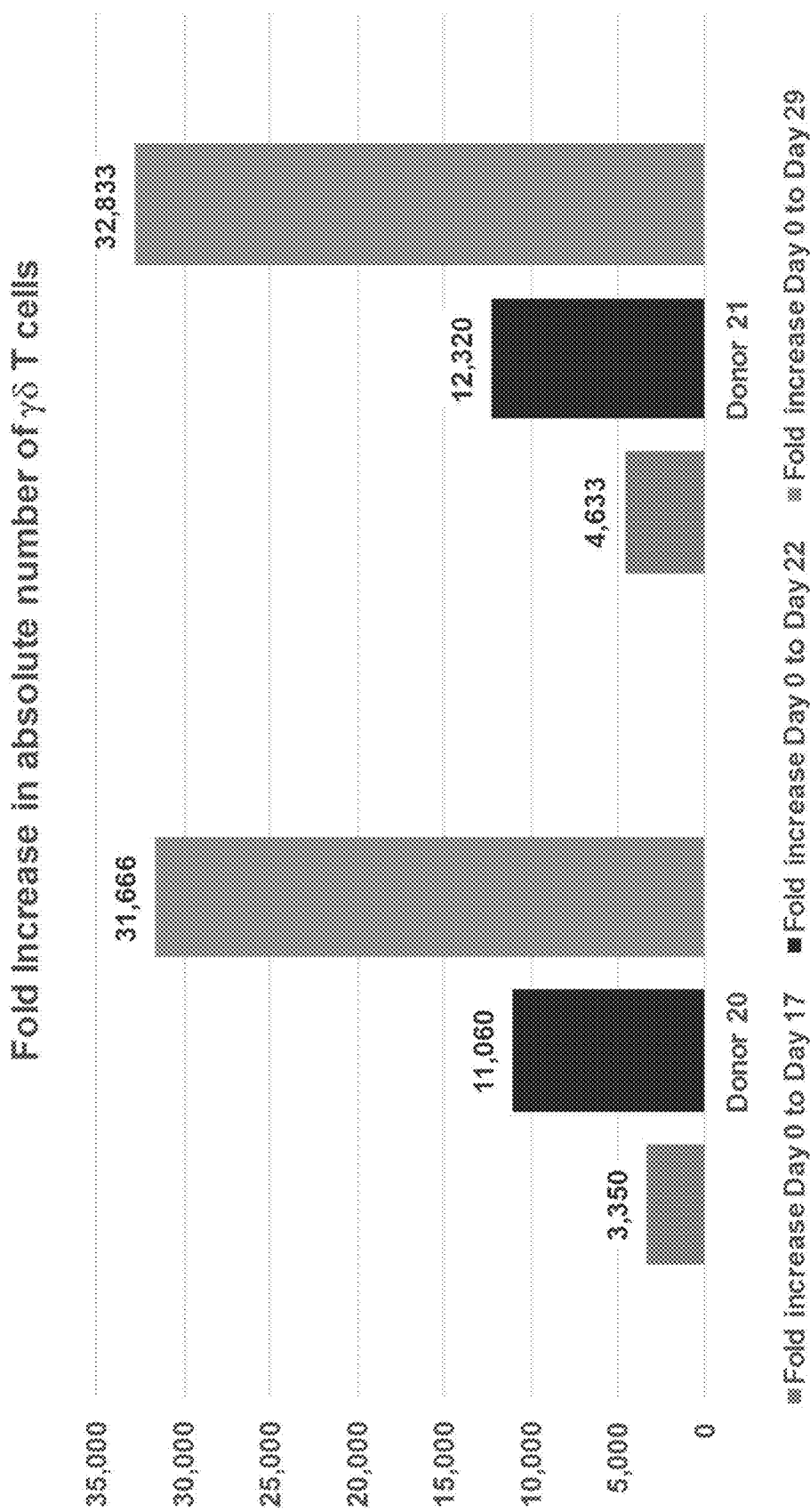
FIG. 6 shows effects of Zoledronate (Zometa) on cell expansion according to an embodiment of the disclosure. γδ T cell were expanded using Zoledronate (Zometa) in defined medium containing IL-2, IL-15, and Amphotericin B.

FIG. 6 shows γδ T cell expansion using Zoledronate (Zometa) in defined medium, which contains IL-2, IL-15, and Amphotericin B. Fold increase in absolute number of γδ T cells is 3,350-fold, 11,060-fold, and 31,666-fold for Donor 20 from Day 0 to Day 17, from Day 0 to Day 22, and from Day 0 to Day 29, respectively. Similarly, fold increase in absolute number of γδ T cells is 4,633-fold, 12,320-fold, and 32,833-fold for Donor 21 from Day 0 to Day 17, from Day 0 to Day 22, and from Day 0 to Day 29, respectively. In contrast, as noted above, classic Vγ9δ2 T cell expansion protocol, at best, could yield only a 100-fold increase in total Vγ9δ2 T cells within 14 days, thereafter, the expansion rate decreases, which may be caused by an increase of cell death. In an aspect, using the afore-mentioned methods, fold increase in absolute number of γδ T cells after expansion on Day 29 as compared with that of Day 0 may be from about 1000-fold to about 40,000-fold, from about 3000-fold to about 35,000-fold, from about 5000-fold to about 35,000-fold, from about 6000-fold to about 35,000-fold, from about 7000-fold to about 35,000-fold, from about 8000-fold to 30,000-fold, from about 10,000-fold to about 35,000-fold, from about 15,000-fold to about 35,000-fold, from about 20,000-fold to about 35,000-fold, from about 25,000-fold to about 35,000-fold, from about 30,000-fold to about 35,000-fold, more than about 10,000 fold, more than about 15,000 fold, more than about 20,000 fold, more than about 25,000 fold, more than about 30,000 fold, more than about 40,000 fold, or more than about 40,000 fold.

Neutrophils (the most abundant leukocytes in the blood) could dampen the growth and survival of γδ T cells. Thus, removal or inactivation of neutrophils may promote the growth and survival of γδ T cells. To achieve this, neutrophilic proteases, such as proteinase 3, elastase, and cathepsin G, may be used to inhibit (1) neutrophils proliferation, (2) cytokine production, and (3) cytotoxicity of γδ T cells via proteolytic cleavage of IL-2 and modulation of butyrophilin 3A1 (CD277). In addition, as observed in polymicrobial septic mice, administration of glutamine and/or N-acetyl cysteine (NAC) reduces the number of neutrophils and increases the percentage of γδ T cells. In addition, as observed in LPS-induced acute lung injured rats, glutamine supplementation reduces the rate of apoptosis in γδ T cells, in part by enhancing glutathione (GSH), an antioxidant, synthesis and thus, reducing the damaging impact of free radicals, i.e., telomere erosion. Based on these observations, as shown in FIGS. 2 and 3, embodiments of the present disclosure may also include supplementing the culture with high dose glutamine/glutamax (or low dose N-acetyl cysteine (NAC), e.g., 1-10 mM, preferably 2.5-7 mM) to resist free radical mediated damage and to sustain γδ T cell replicative potential, and thereby maximizing culture expansion. NAC or high dose glutamine/glutamax can maintain high GSH intracellular levels and counterbalance high free radicals (reactive oxygen species (ROS)) production from monocytes and neutrophils in the culture. Moreover, as shown in FIG. 2, Ibuprofen (a Cyclo-oxygenase-2 (COX-2) inhibitor) can counteract Amphotericin B-mediated activation of COX-2 in monocytes (ZA-Mo), thereby limiting the accumulation of prostaglandin E2 (PGE2) during co-culture with monocytes. Other COX-2 inhibitors, such as valdecoxib, rofecoxib, celecoxib, may also be used.

Example 4

TCR Engineering of Vγ9δ2 T Cells with RD114TR-Pseudotyped Retroviral Vectors

Figure 7:
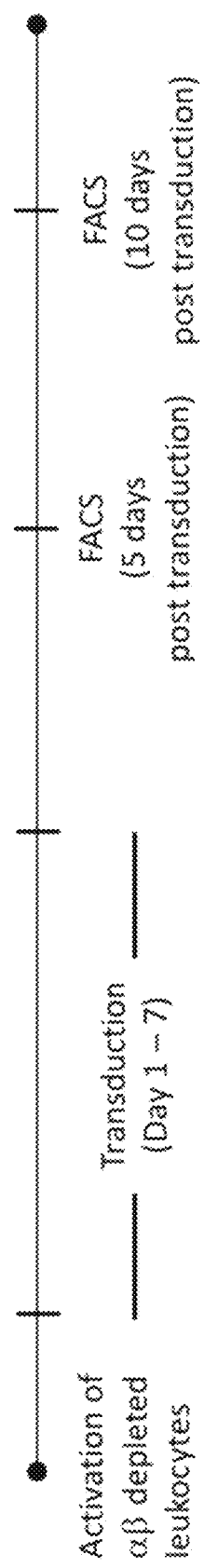
FIG. 7 shows time table for viral transduction into Vγ9δ2 T cells according to an embodiment of the disclosure. On Day 1, fresh PBMC were depleted of αβ T cells and activated with Zoledronate in the presence of IL-2 and IL-15; 24 hours later (on Day 2), cells were transduced using respective viral supernatant at MOI of 1.5; GFP transgene expression was assessed by flow cytometry on Day 7 (i.e., day 5 post-transduction) for transduction efficiency; and on Day 12 (i.e., day 10 post-transduction) for persistent transgene expression.

FIG. 7 shows a time table for viral transduction into Vγ9δ2 T cells. Fresh leukocytes are depleted of αβ T cells and activated with Zoledronate in the presence of IL-2 and IL-15 for a minimum of 1 day or maximum of 7 days. γδ T cells can be transduced between 24 to 168 hours after activation using viral supernatant expressing an αβ TCR and/or CD8.

To determine whether Vγ9δ2 T cells prepared by the methods of the present disclosure are suitable for viral transfection with viruses expressing different envelop proteins, green fluorescent protein (GFP)-expressing γ-retrovirus (e.g., Gibbon Ape Leukemia Virus (GALV) pseudotype (SEQ ID NO: 4) and RD114TR pseudotype (SEQ ID NO: 1)) and GFP-expressing lentivirus (e.g., VSV-G pseudotype (for example, SEQ ID NO: 3)) were tested for their transduction efficiency into these Vγ9δ2 T cells. In addition, CD8α-expressing lentivirus (LV) pseudotyped with VSV-G and RD114TR were tested for their transduction efficiency into Vγ9δ2 T cells.

Figure 8A:
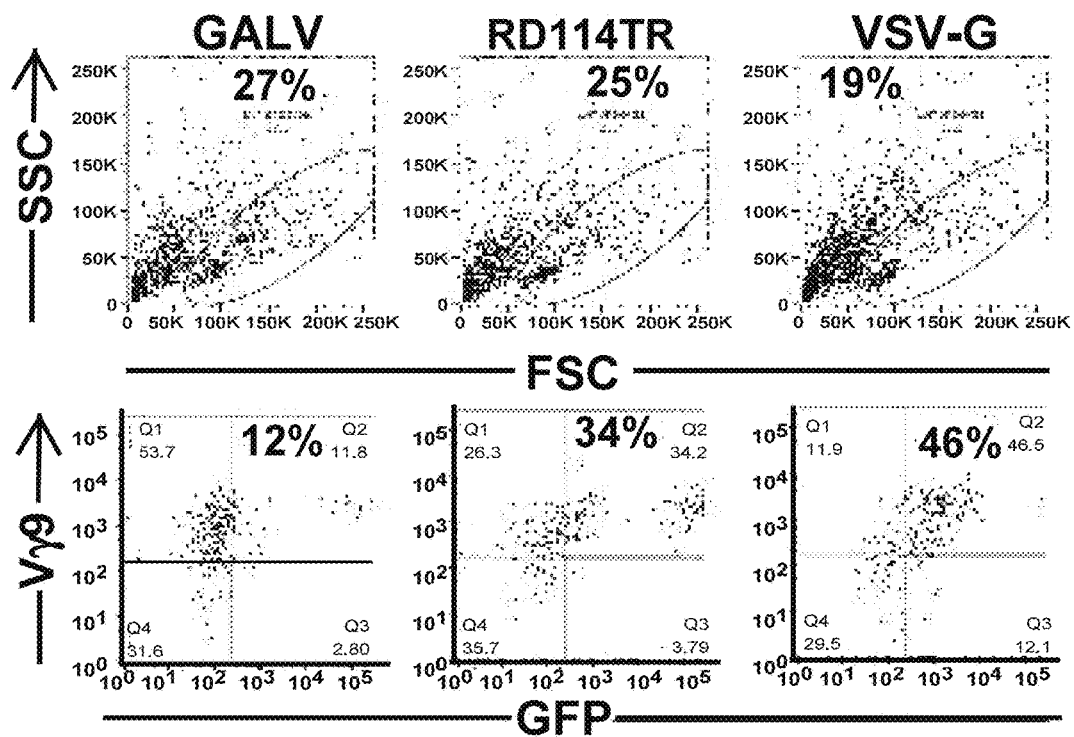
FIG. 8A shows viral transgene expression in Vγ9δ2 T cells using a γ-retroviral vector according to an embodiment of the disclosure. Different envelop protein-expressing viruses, e.g., green fluorescent protein (GFP)-expressing γ-retrovirus (e.g., Gibbon Ape Leukemia Virus (GALV) pseudotype (for example, SEQ ID NO: 4), RD114TR pseudotype (SEQ ID NO: 1), and GFP-expressing lentivirus (e.g., VSV-G pseudotype (for example, SEQ ID NO: 3)) were tested for their transduction efficiency into Vγ9δ2 T cells at Day 5 and Day 10 post-transduction.
Figure 8A:
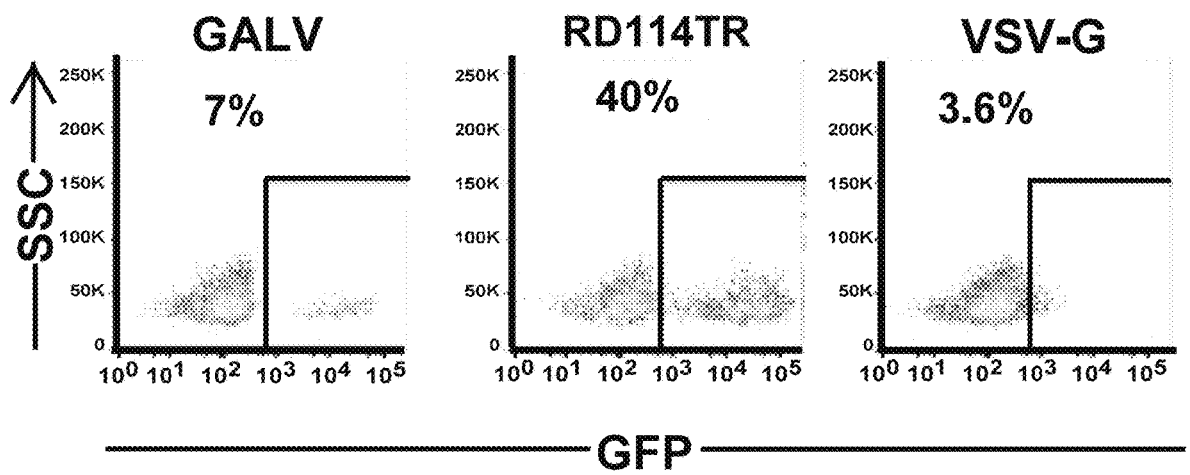

FIG. 8A shows, day 5 post-transduction, GFP expression is 12% for GALV pseudotype, 34% for RD114TR pseudotype, and 46% for VSV-G pseudotype. However, day 10 post-transduction, RD114TR pseudotype maintains GFP expression at 40%, whereas GFP expression of GALV pseudotype and VSV-G pseudotype decreased to 7% and 3.6%, respectively. These results suggest that RD114TR-pseudotyped γ-retrovirus may be optimal gene delivery method for stable gene expression in Zoledronate, IL-2, and IL-15-expanded Vγ9δ2 T cells.

Figure 8B:
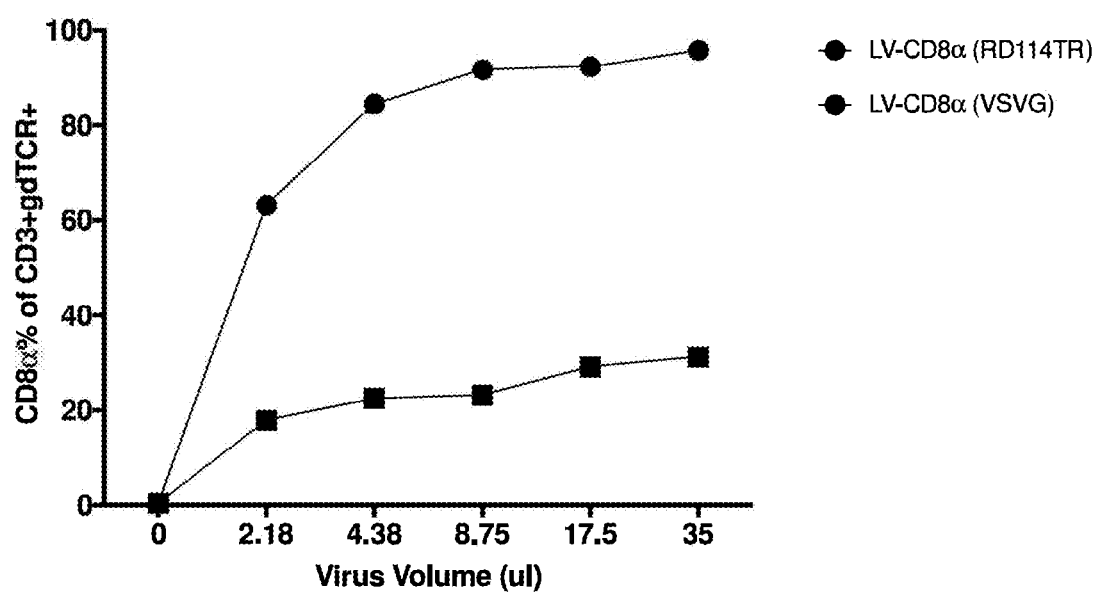
FIG. 8B shows viral transgene, e.g., CD8α, expression in Vγ9δ2 T cells transduced by an RD114TR or a VSV-G pseudotyped lentiviral vector according to an embodiment of the disclosure.

FIG. 8B shows, day 4 post-transduction, CD8a expression on Vγ9δ2 T cells ranged from 63.2% (using 2.18 µl LV) up to 95.8% (using 35 µl LV) when Vγ9δ2 T cells were transduced with LV pseudotyped with RD114TR. On the other hand, CD8a expression on Vγ9δ2 T cells ranged from 17.9% (using 2.18 µl LV) up to 31.2% (using 35 µl LV) when Vγ9δ2 T cells were transduced with LV pseudotyped with VSV-G. Although VSV-G is the most often used envelope and RD114TR is commonly used to pseudotype γ-retrovirus, these results indicate that RD114TR pseudotyped lentivirus not only can be used to transduce Vγ9δ2 T cells but also exhibits higher transduction efficiency into Vγ9δ2 T cells than VSV-G pseudotyped lentivirus.

Example 5

Engineering γδ T Cells Expressing αβ-TCR and CD8αβ

Engineered γδ T-cells of the disclosure may be used to treat a subject in need of treatment for a condition. To engineer γδ T cells that express αβ-TCR specifically binding to a TAA/MHC complex, αβ-TCR-expressing γ-retrovirus (αβ-TCR virus) was generated. Because γδ T cells may not express CD8, γδ T cells may need CD8 in addition to αβ-TCR to recognize TAA/MHC-I complexes on cell membrane of target cells, e.g., cancer cells. To that end, CD8-expressing γ-retrovirus (CD8 virus) was generated.

To determine transduction efficiency of Vγ9δ2 T cells with engineered γ-retroviruses, Zoledronate-activated Vγ9δ2 T cells were transduced with αβ-TCR virus and/or CD8 virus at MOI of 3 in defined medium supplemented with IL-2 and IL-15. Transduction efficiency was measured at 96-hours post-transduction by staining with TAA/MHC-PE dextramer (or negative control NYESO-PE dextramer), followed by CD3, CD8α, and Vδ2 staining. Acquisition on MacsQuant was followed by analysis gating on CD3 population.

Figure 9A:
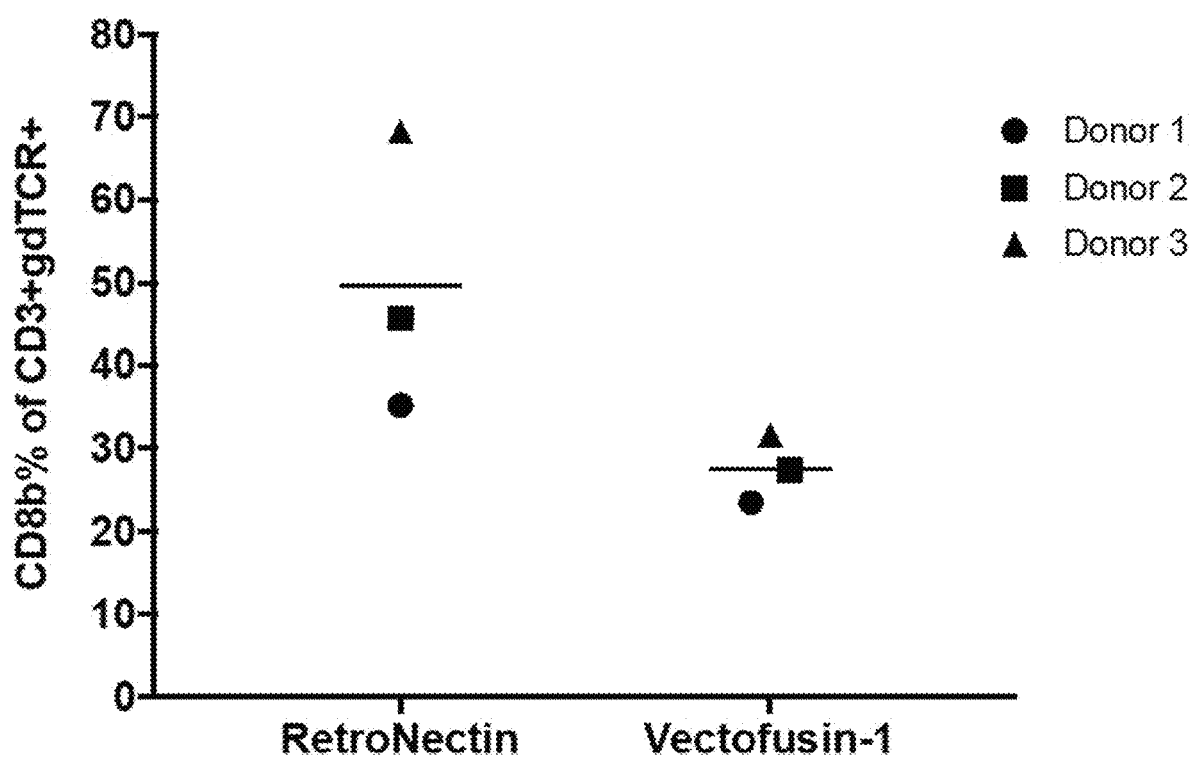
FIG. 9A shows transduction of γδ T cells with CD8αβ using different transduction enhancers (RetroNectin® vs. Vectofusin-1e) during the transduction process. γδ T cells obtained from 3 donors (Donor 1, Donor 2, and Donor 3) were transduced with a retrovirus encoding CD8αβ in the presence of RetroNectin® (a fibronectin fragment coated onto plates) or VectoFusin-1® (a soluble cationic peptide), followed by flow cytometry to determine the % of CD8αβ+ cells.

Transduction may be performed in the presence of transduction enhancers to increase transduction efficiency by physically reducing electrostatic repulsion between the negatively charged cell and the virion and therefore increasing cell-virion interaction. To this end, two transduction enhancers were tested during γδ T cell transduction with a retrovirus encoding CD8αβ. RetroNectin® (a fibronectin fragment coated onto plates) and VectoFusin-1® (a soluble cationic peptide) were tested. FIG. 9A shows, while RetroNectin® resulted in higher transduction efficiencies (mean 49.7%), VectoFusin-1® was also able to transduce γδ T cells at mean transduction efficiency of 27.5%.

Figure 9B:
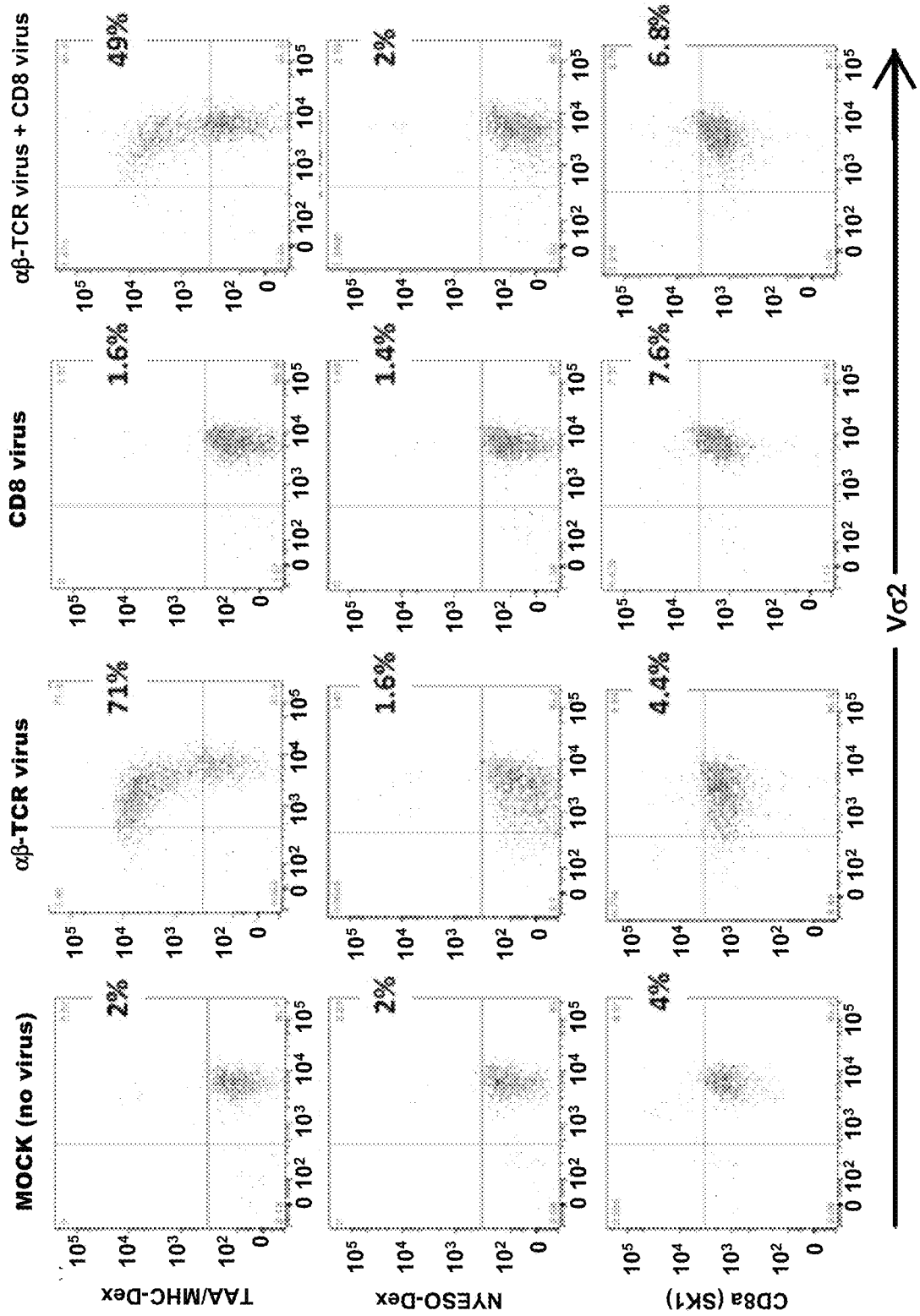
FIG. 9B shows transduction efficiency of Vγ9δ2 T cells with engineered viruses according to an embodiment of the disclosure. Vγ9δ2 T cells were transduced without virus (Mock) or transduced with αβ-TCR virus alone, with CD8 virus alone, or with αβ-TCR virus+CD8 virus. Transduced cells were incubated with TAA/MHC-PE dextramer, anti-CD8 antibody, or NYESO-PE dextramer (negative control), followed by flow cytometry analysis.

FIG. 9B shows 71% of Vγ9δ2 T cells transduced with αβ-TCR virus alone and 49% of Vγ9δ2 T cells transduced with both αβ-TCR virus and CD8 virus identified by TAA/MHC-PE dextramer staining, as compared with negative control NYESO-PE dextramer staining, i.e., transduced with αβ-TCR virus alone (1.6%) and both αβ-TCR virus and CD8 virus (2%). These results indicate αβ-TCR, which specifically binds a TAA/MHC complex, was readily presented on cell surface of the Vγ9δ2 T cells transduced with αβ-TCR virus. In addition, 7.6% of Vγ9δ2 T cells transduced with CD8 virus alone and 6.8% of Vγ9δ2 T cells transduced with both αβ-TCR virus and CD8 virus were identified by CD8a staining, as compared with mock (no virus) (4%) and transduced with αβ-TCR virus alone (4.4%). These data show Vγ9δ2 T cells prepared by Zoledronate, IL-2, and IL-15-mediated activation and expansion can be used to express TAA-specific TCRs and CD8 by viral transduction.

Figure 10:
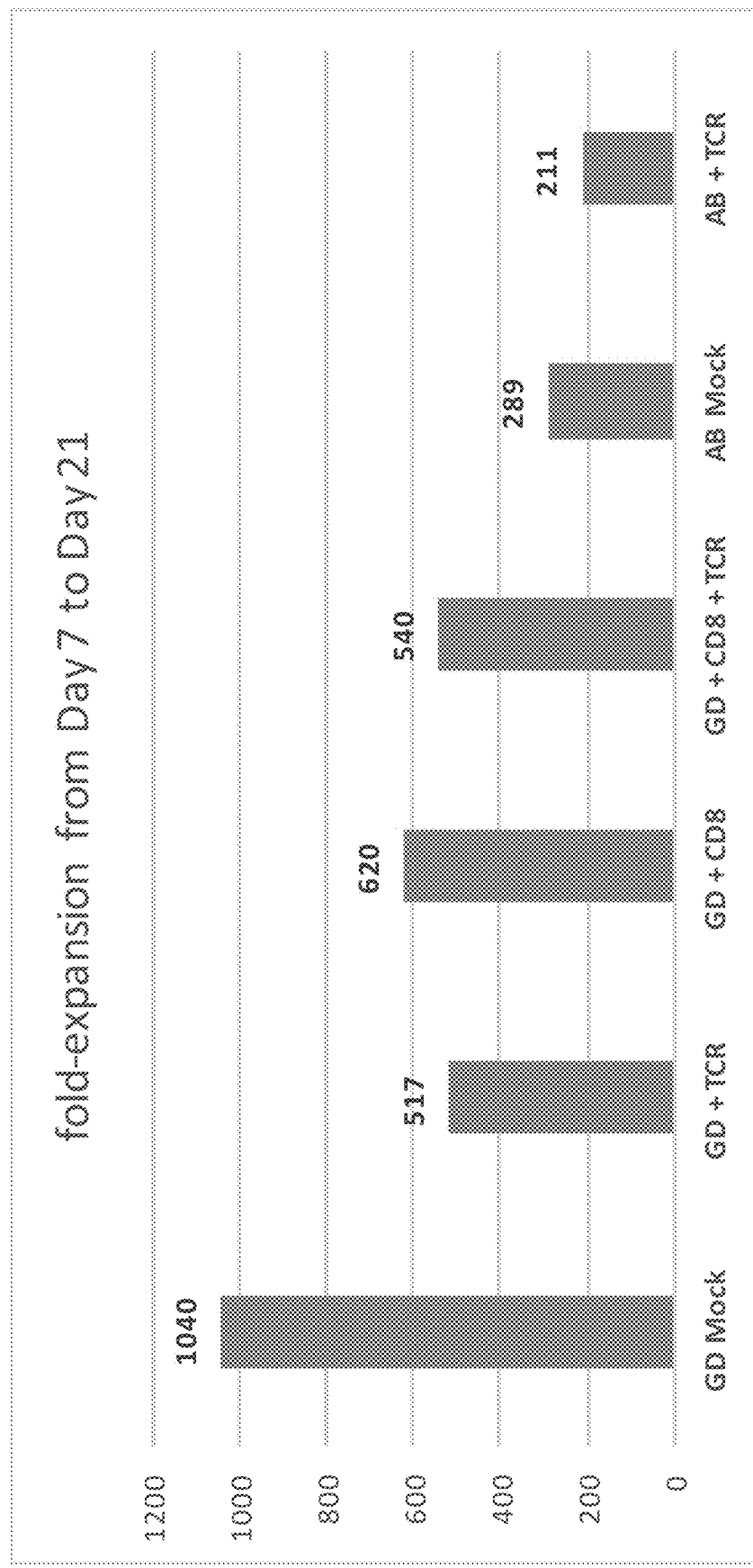
FIG. 10 shows fold-expansion of Vγ9δ2 T cells transduced with engineered viruses according to an embodiment of the disclosure. Vγ9δ2 T cells (GD) or αβ T cells (AB) were transduced without virus (Mock), with αβ-TCR virus (TCR), with CD8 virus (CD8), or with CD8+TCR, followed by measurement of fold expansion from day 7 to day 21 post-transduction.
Figure 11A:
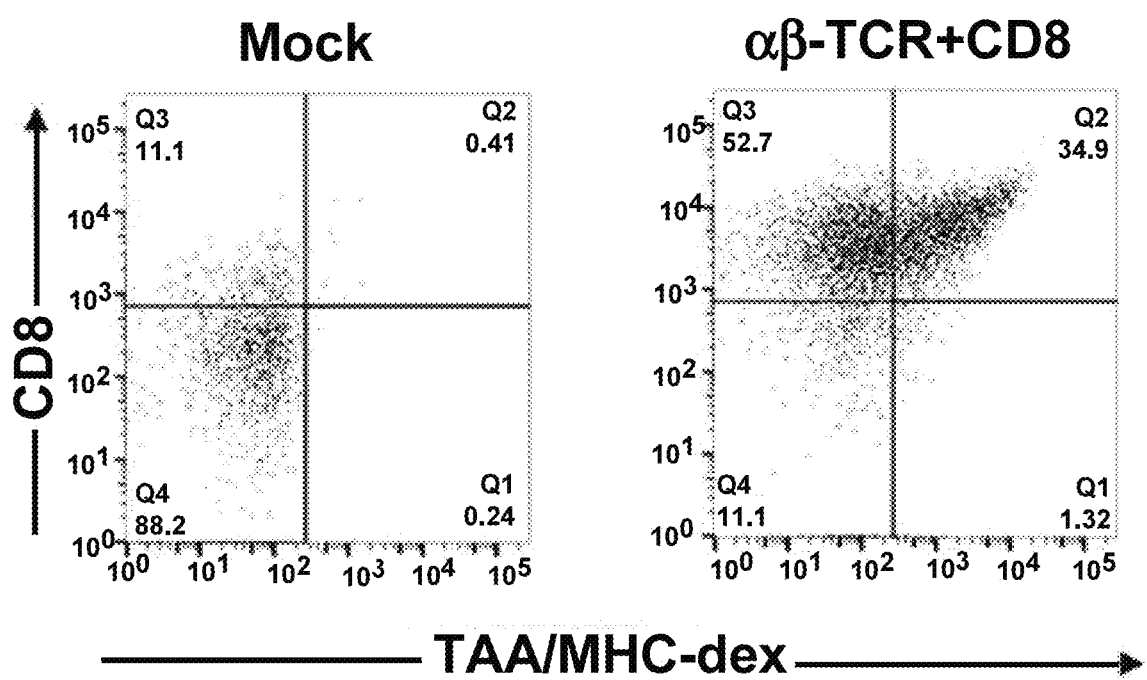
FIG. 11A shows engineered Vγ9δ2 T cells according to an embodiment of the disclosure. Vγ9δ2 T cells transduced without virus (Mock) or with αβ-TCR retrovirus and CD8αβ retrovirus (αβ-TCR+CD8) were incubated with TAA/MHC complex, followed by flow cytometry analysis to detect Vγ9δ2 T cells that bind to TAA/MHC complex.

To determine the fold-expansion of Vγ9δ2 T cells after viral transduction, Vγ9δ2 T cells (GD) or αβ T cells (AB) were transduced with αβ-TCR virus (TCR) and/or CD8 virus (CD8) followed by measurement of fold expansion from day 7 to day 21 post-transduction. FIG. 10 shows, without transduction, Vγ9δ2 T cells (GD Mock) (1,040-fold) generally have higher fold expansion than αβ T cells (AB Mock) (289-fold). After transduction with αβ-TCR alone, Vγ9δ2 T cells (GD+TCR) have 517-fold, which is higher than that of αβ T cells (AB+TCR) (211-fold). After transduction with CD8 alone (GD+CD8) or CD8+αβ-TCR (GD+CD8+TCR), Vγ9δ2 T cells have 620-fold and 540-fold expansion, respectively. These results indicate that Vγ9δ2 T cells possess better capacity for cell expansion than αβ T cells, in general, and for viral transduction.

αβ-TCR-expressing Vγ9δ2 T cells, in which αβ-TCR specifically binds to TAA/MHC complex, were generated by transducing Vγ9δ2 T cells with αβ-TCR retrovirus and CD8αβ retrovirus. FIG. 11A shows, as compared with Vγ9δ2 T cells without viral transduction (Mock), 34.9% of Vγ9δ2 T cells transducing with αβ-TCR retrovirus and CD8αβ retrovirus (αβ-TCR+CD8) stained positive by TAA/MHC-dextramer (TAA/MHC-dex) and anti-CD8 antibody (CD8), indicating the generation of Vγ9δ2 T cells expressing both αβ-TCR and CD8αβ on cell surface (αβ-TCR+CD8αβ engineered Vg9d2 T cells).

To determine cytolytic activity of engineered Vγ9δ2 T cells, αβ-TCR+CD8αβ engineered Vγ9δ2 T cells were exposed to target cells, e.g., A375 cell line, which is a human malignant melanoma cell line having TAA/MHC complex presented on cell surface. Four functional assays: (1) CD107a degranulation, (2) IFN-γ release, (3) apoptosis of A375 cells after 6 hours, and (4) cytotoxic effect of engineered γδ T cells on A375 after long term co-culture.

Figure 11B:
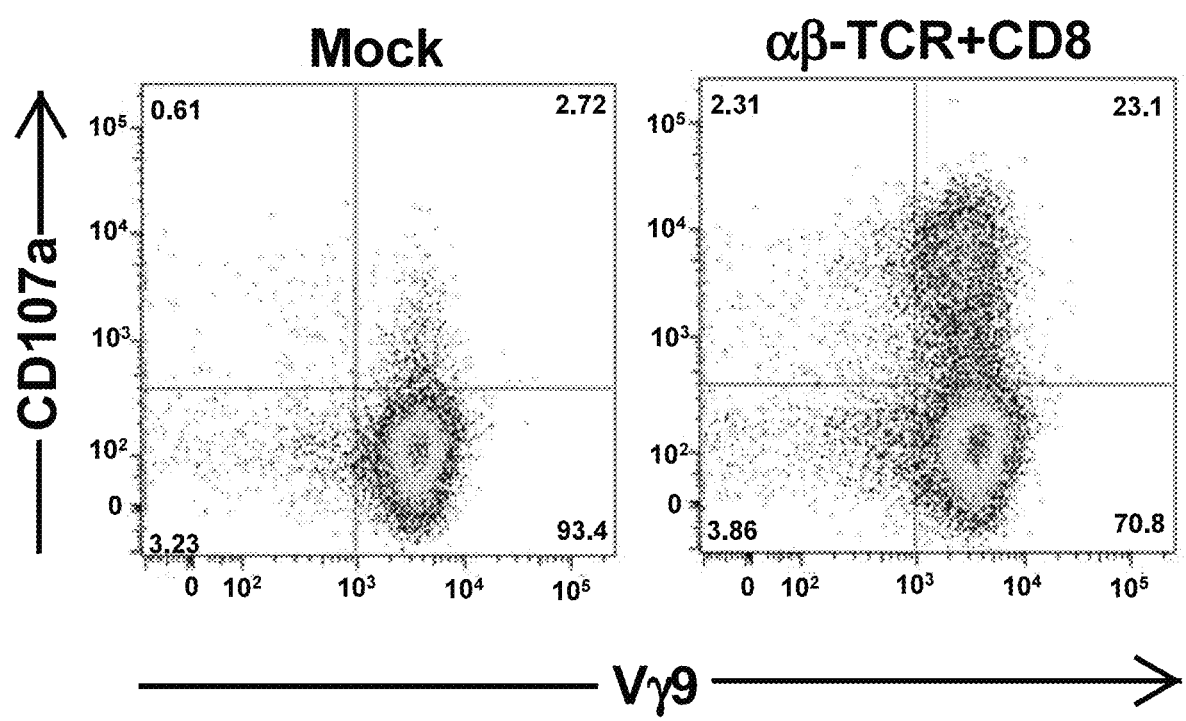
FIG. 11B shows functional assessments of engineered Vg9d2 T cells according to an embodiment of the disclosure. Vγ9δ2 T cells transduced without virus (Mock) or with αβ-TCR retrovirus and CD8αβ retrovirus (αβ-TCR+CD8) were incubated with target cells, followed by flow cytometry analysis to detect CD107a, an apoptosis marker.

The principle of CD107a degranulation assay is based on killing of target cells via a granule-dependent pathway that utilizes pre-formed lytic granules located within the cytoplasm of cytotoxic cells. The lipid bilayer surrounding these granules contains lysosomal associated membrane glycoproteins (LAMPs), including CD107a (LAMP-1). Rapidly upon recognition of target cells via the T cell receptor complex, apoptosis-inducing proteins like granzymes and perforin are released into the immunological synapse, a process referred to as degranulation. Thereby, the transmembrane protein CD107a is exposed to the cell surface and can be stained by specific monoclonal antibodies. FIG. 11B shows, as compared with Vγ9δ2 T cells without viral transduction (Mock), 23.1% of Vγ9δ2 T cells transduced with αβ-TCR retrovirus and CD8αβ retrovirus (αβ-TCR+CD8) incubated with target cells, e.g., A375 cells, stained positive by anti-CD107a antibody, indicating that αβ-TCR+CD8αβ engineered Vg9d2 T cells are cytolytic by carrying out degranulation, when exposed to A375 cells.

Figure 11C:
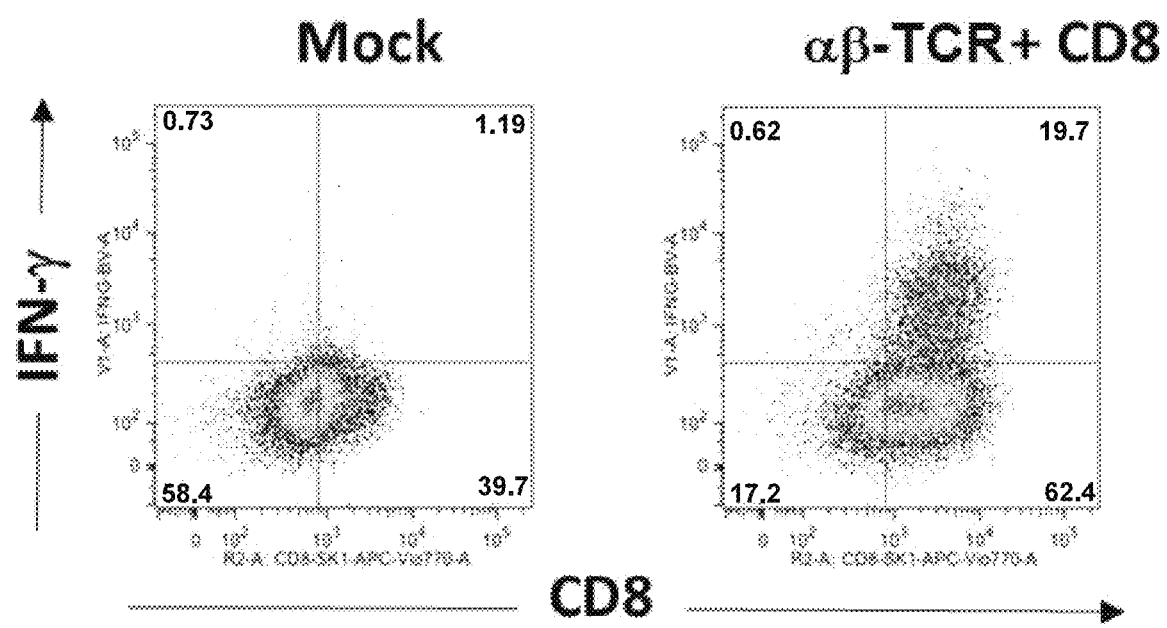
FIG. 11C shows functional assessments of engineered Vg9d2 T cells according to another embodiment of the disclosure. Vγ9δ2 T cells transduced without virus (Mock) or with αβ-TCR retrovirus and CD8αβ retrovirus (αβ-TCR+CD8) were incubated with target cells, followed by flow cytometry analysis to detect IFN-γ release.

IFN-γ release assays measure the cell mediated response to antigen-presenting cells, e.g., A375 cells, through the levels of IFN-γ released, when TCR of T cells specifically binds to peptide/MHC complex of antigen-presenting cells on cell surface. FIG. 11C shows, as compared with Vγ9δ2 T cells without viral transduction (Mock), 19.7% of Vγ9δ2 T cells transduced with αβ-TCR retrovirus and CD8αβ retrovirus (αβ-TCR+CD8) stained positive by anti-IFN-γ antibody, indicating that αβ-TCR+CD8αβ engineered Vγ9δ2 T cells are cytolytic by releasing IFN-γ, when exposed to A375 cells.

Figure 11D:
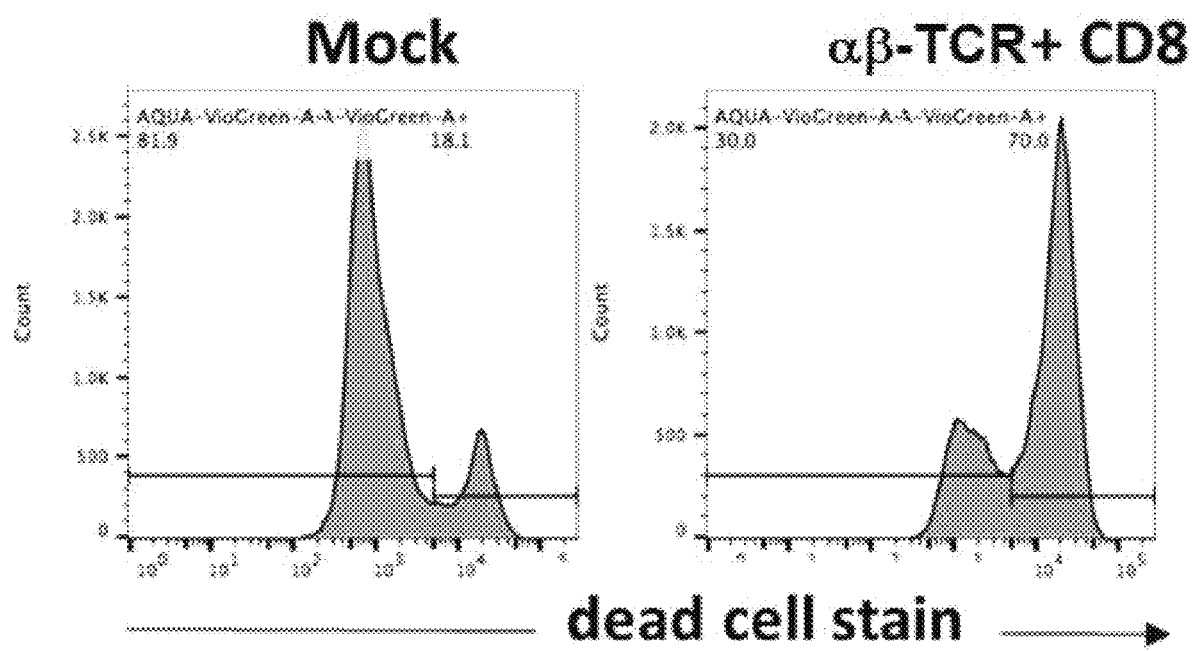
FIG. 11D shows cytolytic activity of engineered Vg9d2 T cells according to an embodiment of the disclosure. Vγ9δ2 T cells transduced without virus (Mock) or with αβ-TCR retrovirus and CD8αβ retrovirus (αβ-TCR+CD8) were incubated with target cells, followed by flow cytometry analysis to detect apoptotic cells.

Cytolytic activity were evaluated at 24 hours post-exposure to A375 cells by gating on apoptosis of non-CD3 T cells, i.e., A375 cells. Apoptosis was assessed by staining the harvested culture with live/dead dye. FIG. 11D shows, as compared with Vγ9δ2 T cells without viral transduction (Mock), αβ-TCR+CD8αβ engineered Vγ9δ2 T cells (αβ-TCR+CD8) induced apoptosis in 70% of A375 cells, indicating that αβ-TCR+CD8αβ engineered Vγ9δ2 T cells are cytolytic by killing A375 cells.

Figure 11E:
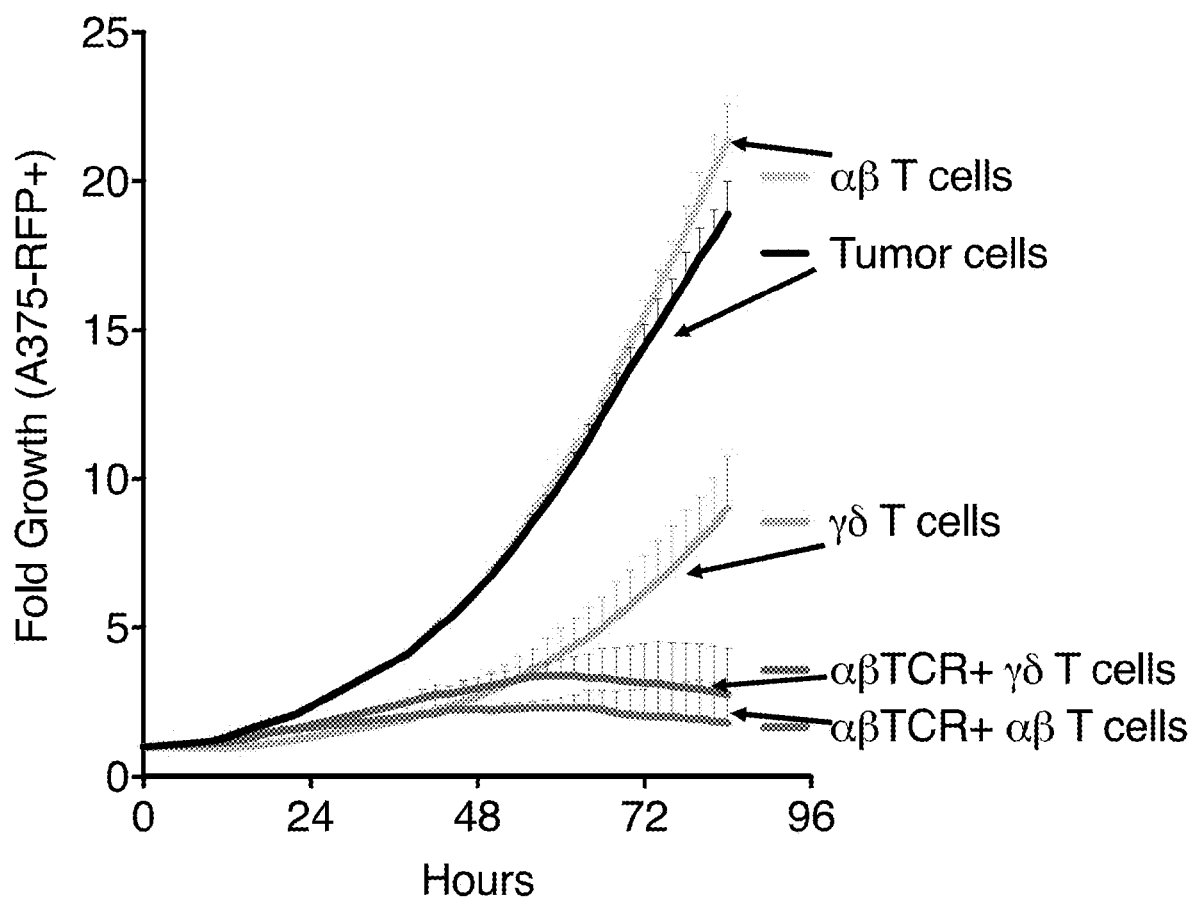
FIG. 11E shows prolonged cytolytic activity of engineered γδ T cells according to an embodiment of the disclosure. Cytolytic activity was evaluated in real-time during an 84-hour co-culture assay. Target positive A375-RFP tumor cells were incubated without T cells (tumor cells) or with non-transduced cells (αβ T cells and γδ T cells), with αβ T cells transduced with αβ-TCR virus and CD8αβ virus (αβTCR+αβ T cells), or with γδ T cells transduced with αβ-TCR virus and CD8αβ virus (αβTCR+γδ T cells), followed by IncuCyte® live cell analysis to measure target cell growth.

Cytolytic activity was also evaluated in real-time during an 84-hour co-culture assay. Non-transduced and αβTCR+CD8αβ transduced γδ T cells were co-culture with target positive A375-RFP tumor cells at an effector to target ratio of 3:1. Lysis of target positive A375-RFP tumor cells was assessed in real time by IncuCyte® live cell analysis system (Essen BioScience). Tumor cells alone and non-transduced and αβTCR transduced αβ T cells were used as negative and positive controls, respectively. As shown in FIG. 11E, while non-transduced γδ T cells showed cytotoxic potential due to intrinsic anti-tumor properties of γδ T cells, αβTCR+CD8αβ transduced γδ T cells showed similar cytotoxic potential as compared to αβTCR transduced αβ T cells, indicating that αβTCR+CD8αβ transduced γδ T cells can be engineered to target and kill tumor cells.

These data indicate engineered Vγ9δ2 T cells produced by the methods of the present disclosure are functional and can be used to kill target cells, e.g., cancer cells, in a TAA peptide-specific manner.

In an aspect, TAA peptides described herein that are capable of use with the methods and embodiments described herein include, for example, those TAA peptides described in U.S. Publication 20160187351, U.S. Publication 20170165335, U.S. Publication 20170035807, U.S. Publication 20160280759, U.S. Publication 20160287687, U.S. Publication 20160346371, U.S. Publication 20160368965, U.S. Publication 20170022251, U.S. Publication 20170002055, U.S. Publication 20170029486, U.S. Publication 20170037089, U.S. Publication 20170136108, U.S. Publication 20170101473, U.S. Publication 20170096461, U.S. Publication 20170165337, U.S. Publication 20170189505, U.S. Publication 20170173132, U.S. Publication 20170296640, U.S. Publication 20170253633, and U.S. Publication 20170260249, the contents of each of these publications and sequence listings described therein are herein incorporated by reference in their entireties.

Example 6

Engineering γδ T Cells Expressing Chimeric Molecules

γδ T cells may be engineered to express a chimeric tumor recognition moiety containing a ligand binding domain derived from NKG2D, NKG2A, NKG2C, NKG2F, LLT1, AICL, CD26, NKRP1, NKp30, NKp44, NKp46, CD244 (2B4), DNAM-1, and NKp80, or an anti-tumor antibody such as anti-Her2neu or anti-EGFR and a signaling domain obtained from CD3-ζ, Dap 10, CD28, 4-IBB, and CD40L. In some examples, the chimeric receptor binds MICA, MICB, Her2neu, EGFR, mesothelin, CD38, CD20, CD 19, PSA, RON, CD30, CD22, CD37, CD38, CD56, CD33, CD30, CD138, CD123, CD79b, CD70, CD75, CA6, GD2, alpha-fetoprotein (AFP), carcinoembryonic antigen (CEA), CEACAM5, CA-125, MUC-16, 5T4, NaPi2b, ROR1, ROR2, 5T4, PLIF, Her2/Neu, EGFRvIII, GPMNB, LIV-1, glycolipidF77, fibroblast activating protein, PSMA, STEAP-1, STEAP-2, c-met, CSPG4, Nectin-4, VEGFR2, PSCA, folate binding protein/receptor, SLC44A4, Cripto, CTAG1B, AXL, IL-13R, IL-3R, SLTRK6, gp100, MART1, Tyrosinase, SSX2, SSX4, NYESO-1, epithelial tumor antigen (ETA), MAGEA family genes (such as MAGE3A. MAGE4A), KKLC1, mutated ras, prat p53, MHC class I chain-related molecule A (MICA), or MHC class I chain-related molecule B (MICB), HPV, or CMV.

Other engineered viruses that may be used to transduce γδ T cells may include two viruses to express αβ TCR and chimeric CD8/CD4 separately. Alternatively, both TAA-specific αβ TCR and chimeric CD8/CD4 (with truncated colony stimulating factor 1 receptor (CSF1R)) may be included in a single virus.

Figure 12A:
FIG. 12A shows a schematic of an engineered virus according to an embodiment of the disclosure. CD8/CD4 chimeric receptor-T2A-truncated CSF1R contains CD8α extracellular domain linked to CD4 transmembrane and intracellular domain.

FIG. 12A shows, for example, CD8/CD4 chimeric receptor-T2A-truncated CSF1R, in which CD8α extracellular domain may be linked to CD4 transmembrane and intracellular domain. CD8α is required for binding to αβ domain of MHC I molecule, in which CD8β is important for palmitoylation, hence, providing proper recruitment of CD8 to lipid rafts for interaction with TCR complex. On the other hand, CD4 functions as monomer and can localize to lipid rafts and, similar to CD8 intracellular domain, CD4 intracellular domain can recruit lymphocyte-specific protein tyrosine kinase (Lck), which can interact with the cytoplasmic tails of the CD4 and CD8 co-receptors on T helper cells and cytotoxic T cells, respectively, to assist signaling from the TCR complex. Therefore, instead of expressing both CD8α and CD8β, a chimeric CD8/CD4 protein that can bind to MHC I molecule and localize to lipid rafts may be generated. Truncated CSF1 receptor (CSF1R) intracellular catalytic domain may be linked downstream from chimeric CD8/CD4 protein used as kill switch, when the function of a chimeric CD8/CD4 protein is no longer needed. CSF1R is not expressed on T cells and is most abundant in myeloid cells. Therefore, turning off CSF1R intracellular catalytic domain-mediated signaling would have minimum effect on T cells, such as γδ T cells. To turn off CSF1R signaling, a number of tyrosine kinase inhibitors, e.g., R7155, CYC11645, Ki20227, GW2580, BLZ945, PLX5622, and PLX3397, may be used. Other receptors may be used as kill switch including, but not limited to, truncated TNFR2, truncated ESR1, and/or ESR1/Fas signaling, which may activate estrogen receptor to induce Fas-mediated death of T cells.

CSF1 can promote M1 (classically activated macrophages) to M2 (alternatively activated macrophages) polarization. In tumor microenvironment, CSF1 can polarize tumor-associated macrophages (TAM) from M1 to M2 type. This may not be desirable because M1 type of TAM has more tumor-killing activity than M2 type of TAM. To exploit the presence of CSF1 in tumor microenvironment and to drive T cell function/persistence and to reduce the availability of CSF1 to polarize TAM, CSF1R extracellular domain that binds CSF1 may be included in chimeric CD8/CD4 protein.

Figure 12B:
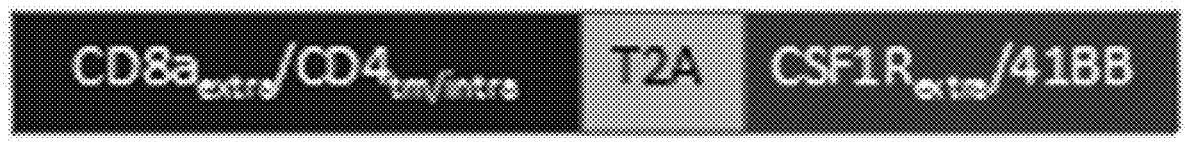
FIG. 12B shows a schematic of an engineered virus according to an embodiment of the disclosure. CD8/CD4 chimeric receptor-T2A-CSF1R/41 BB chimeric receptor contains CSF1R extracellular domain linked downstream from chimeric CD8/CD4 protein.

FIG. 12B shows, for example, CD8/CD4 chimeric receptor-T2A-CSF1R/41 BB chimeric receptor, in which CSF1R extracellular domain is linked downstream from chimeric CD8/CD4 protein so that CSF1R extracellular domain can bind and sequester CSF1 away from macrophages, thus, reducing M1 to M2 polarization. By providing costimulatory molecule, e.g., 41 BB, this fusion protein may promote survival and expansion of T cells, such as γδ T cells.

Advantages of the present disclosure may include (1) use of γδ T cells to elicit cytotoxicity against mevalonate-dependent tumors; (2) use of γδ T cells as an allogeneic cell engineered to express a tumor antigen specific chimeric antigen receptor (CAR) or αβ-TCR with or without deletion of endogenous γδ TCR; (3) use of γδ T cells as allogeneic immune cells by co-administering with various forms of antibodies or T-cell engagers to treat immune compromised cancer patients; (4) use of γδ T cells to enhance maturation of dendritic cells for cancer vaccine; and (5) use of γδ T cells as antigen presenting cells for enhancing the activation of cytotoxic CD8 T cells.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. An in vitro method of activating and expanding γδ T cells comprising isolating γδ T cells from a blood sample of a human subject,
   activating the isolated γδ T cells in the presence of an aminobisphosphonate, human recombinant interleukin 2 (IL-2), and human recombinant interleukin 15 (IL-15), and
   expanding the activated γδ T cells in the absence of an aminobisphosphonate and in the presence of human recombinant interleukin 2 (IL-2) and human recombinant interleukin 15 (IL-15), wherein the fold-expansion of the expanded γδ T cells is about 10,000-fold to about 35,000-fold.

2. The method of claim 1, wherein the γδ T cells are isolated from a leukapheresis human sample.

3. The method of claim 1, wherein the aminobisphosphonate comprises pamidronic acid, alendronic acid, zoledronic acid, risedronic acid, ibandronic acid, incadronic acid, a salt thereof and/or a hydrate thereof.

4. The method of claim 1, wherein the aminobisphosphonate is zoledronic acid.

5. The method of claim 1, wherein the activation is in the presence of zoledronic acid and a cytokine composition consisting of IL-2 and IL-15.

6. The method of claim 1, wherein the activation is further in the presence of a Toll-like receptor 2 (TLR2) ligand.

7. The method of claim 6, wherein the TLR2 ligand is selected from Amphotericin B, L-theanine, tannin, and polyphenols.

8. The method of claim 1, wherein the activation is further in the presence of N-acetyl cysteine (NAC).

9. The method of claim 1, wherein the activation is further in the presence of a COX-2 inhibitor.

10. The method of claim 1, wherein the activation is in the presence of zoledronic acid at a concentration of about 1 μM to about 10 μM.

11. The method of claim 1, wherein the activation is in the presence of IL-2 at a concentration of about 10 IU/ml to about 100 IU/ml.

12. The method of claim 1, wherein the activation is in the presence of zoledronic acid at a concentration of about 1 μM to about 100 μM, IL-2 at a concentration from about 10 IU/ml to about 200 IU/ml, and IL-15 at a concentration of about 10-500 ng/ml.

13. The method of claim 1, wherein the expansion is in the presence of IL-2 at a concentration from about 10 IU/ml to about 100 IU/ml and/or IL-15 at a concentration of about 50-200 ng/ml.

14. The method of claim 1, wherein the activation is further in the presence of a phosphoantigen selected from the group consisting of (E)-4-hydroxy-3-methyl-but-2-enyl pyrophosphate (HMBPP), isoprenoid pyrophosphates (farnesyl pyrophosphate (FPP), geranylgeranyl pyrophosphate (GGPP), isopentenyl pyrophosphate (IPP), and dimethylallyl diphosphate (DMAPP).

15. The method of claim 1, wherein the fold-expansion of the expanded γδ T cells is about 15,000-fold to about 35,000-fold.

16. The method of claim 1, wherein the fold-expansion of the expanded γδ T cells is about 20,000-fold to about 35,000-fold.

* * * * *

SEQUENCE LISTING

```
<160> NUMBER OF SEQ ID NOS: 5

<210> SEQ ID NO 1
<211> LENGTH: 559
<212> TYPE: PRT
<213> ORGANISM: Artificial Sequence
<220> FEATURE:
<223> OTHER INFORMATION: RD114TR Fusion Protein

<400> SEQUENCE: 1

Met Lys Leu Pro Thr Gly Met Val Ile Leu Cys Ser Leu Ile Ile Val
1               5                   10                  15

Arg Ala Gly Phe Asp Asp Pro Arg Lys Ala Ile Ala Leu Val Gln Lys
            20                  25                  30

Gln His Gly Lys Pro Cys Glu Cys Ser Gly Gly Gln Val Ser Glu Ala
        35                  40                  45

Pro Pro Asn Ser Ile Gln Gln Val Thr Cys Pro Gly Lys Thr Ala Tyr
    50                  55                  60

Leu Met Thr Asn Gln Lys Trp Lys Cys Arg Val Thr Pro Lys Ile Ser
65                  70                  75                  80

Pro Ser Gly Gly Glu Leu Gln Asn Cys Pro Cys Asn Thr Phe Gln Asp
                85                  90                  95
```

```
Ser Met His Ser Ser Cys Tyr Thr Glu Tyr Arg Gln Cys Arg Arg Ile
                100                 105                 110

Asn Lys Thr Tyr Tyr Thr Ala Thr Leu Leu Lys Ile Arg Ser Gly Ser
            115                 120                 125

Leu Asn Glu Val Gln Ile Leu Gln Asn Pro Asn Gln Leu Leu Gln Ser
        130                 135                 140

Pro Cys Arg Gly Ser Ile Asn Gln Pro Val Cys Trp Ser Ala Thr Ala
145                 150                 155                 160

Pro Ile His Ile Ser Asp Gly Gly Pro Leu Asp Thr Lys Arg Val
                165                 170                 175

Trp Thr Val Gln Lys Arg Leu Glu Gln Ile His Lys Ala Met Thr Pro
            180                 185                 190

Glu Leu Gln Tyr His Pro Leu Ala Leu Pro Lys Val Arg Asp Asp Leu
        195                 200                 205

Ser Leu Asp Ala Arg Thr Phe Asp Ile Leu Asn Thr Thr Phe Arg Leu
    210                 215                 220

Leu Gln Met Ser Asn Phe Ser Leu Ala Gln Asp Cys Trp Leu Cys Leu
225                 230                 235                 240

Lys Leu Gly Thr Pro Thr Pro Leu Ala Ile Pro Thr Pro Ser Leu Thr
                245                 250                 255

Tyr Ser Leu Ala Asp Ser Leu Ala Asn Ala Ser Cys Gln Ile Ile Pro
            260                 265                 270

Pro Leu Leu Val Gln Pro Met Gln Phe Ser Asn Ser Ser Cys Leu Ser
        275                 280                 285

Ser Pro Phe Ile Asn Asp Thr Glu Gln Ile Asp Leu Gly Ala Val Thr
    290                 295                 300

Phe Thr Asn Cys Thr Ser Val Ala Asn Val Ser Ser Pro Leu Cys Ala
305                 310                 315                 320

Leu Asn Gly Ser Val Phe Leu Cys Gly Asn Asn Met Ala Tyr Thr Tyr
                325                 330                 335

Leu Pro Gln Asn Trp Thr Arg Leu Cys Val Gln Ala Ser Leu Leu Pro
            340                 345                 350

Asp Ile Asp Ile Asn Pro Gly Asp Glu Pro Val Pro Ile Pro Ala Ile
        355                 360                 365

Asp His Tyr Ile His Arg Pro Lys Arg Ala Val Gln Phe Ile Pro Leu
    370                 375                 380

Leu Ala Gly Leu Gly Ile Thr Ala Ala Phe Thr Thr Gly Ala Thr Gly
385                 390                 395                 400

Leu Gly Val Ser Val Thr Gln Tyr Thr Lys Leu Ser His Gln Leu Ile
                405                 410                 415

Ser Asp Val Gln Val Leu Ser Gly Thr Ile Gln Asp Leu Gln Asp Gln
            420                 425                 430

Val Asp Ser Leu Ala Glu Val Val Leu Gln Asn Arg Arg Gly Leu Asp
        435                 440                 445

Leu Leu Thr Ala Glu Gln Gly Gly Ile Cys Leu Ala Leu Gln Glu Lys
    450                 455                 460

Cys Cys Phe Tyr Ala Asn Lys Ser Gly Ile Val Arg Asn Lys Ile Arg
465                 470                 475                 480

Thr Leu Gln Glu Glu Leu Gln Lys Arg Arg Glu Ser Leu Ala Ser Asn
                485                 490                 495

Pro Leu Trp Thr Gly Leu Gln Gly Phe Leu Pro Tyr Leu Leu Pro Leu
            500                 505                 510
```

```
Leu Gly Pro Leu Leu Thr Leu Leu Ile Leu Thr Ile Gly Pro Cys
            515                 520                 525

Val Phe Asn Arg Leu Val Gln Phe Val Lys Asp Arg Ile Ser Val Val
    530                 535                 540

Gln Ala Leu Val Leu Thr Gln Gln Tyr His Gln Leu Lys Pro Leu
545                 550                 555

<210> SEQ ID NO 2
<211> LENGTH: 662
<212> TYPE: PRT
<213> ORGANISM: Feline Endogeneous Virus

<400> SEQUENCE: 2

Met Lys Pro Pro Ala Gly Met Val Phe Leu Trp Val Leu Thr Ser Leu
1               5                   10                  15

Gly Ala Gly Ile Gly Ala Lys Ile Val Lys Glu Gly Asn Pro His Gln
            20                  25                  30

Val Tyr Thr Leu Thr Trp Gln Ile Tyr Ser Gln Ser Gly Glu Val Val
            35                  40                  45

Trp Glu Val Gln Gly Asn His Ala Leu Asn Thr Trp Trp Pro Leu
    50                  55                  60

Thr Pro Asp Phe Cys Gln Leu Ala Ala Gly Leu Asp Thr Trp Asp Ile
65                  70                  75                  80

Pro Ala Arg Ser Pro Lys Asn Leu Gln Ser Tyr Met Gly Glu Arg Ile
                85                  90                  95

Gln Gln Met Thr Ala His Gly Cys Ser Ser Pro Thr Ala Arg Cys Arg
            100                 105                 110

Leu Ala Gln Ala Glu Phe Tyr Val Cys Pro Arg Asp Asn Arg Asp Arg
            115                 120                 125

Ala Thr Ala His Arg Cys Gly Gly Tyr Glu Glu Tyr Phe Cys Ser Ala
            130                 135                 140

Trp Gly Cys Glu Thr Thr Gly Asp Ala Tyr Trp Gln Pro Thr Ser Ser
145                 150                 155                 160

Trp Asp Leu Ile Thr Ile Thr Arg Gly Tyr Thr Lys Pro Asp Pro Asp
                165                 170                 175

Gly His Thr Cys Tyr Tyr Lys Lys Gly Thr Glu Gly Tyr His His Trp
            180                 185                 190

Ile Ser Pro Leu Ser Leu Pro Leu Lys Ile Thr Phe Thr Asp Ser Gly
            195                 200                 205

Lys Arg Ala Leu Gly Trp Gln Thr Gly Tyr Thr Trp Gly Leu Arg Trp
    210                 215                 220

Tyr Leu Pro Gly Lys Asp Arg Gly Ile Val Leu Lys Ile Lys Leu Lys
225                 230                 235                 240

Ile Asp Thr Ile Thr Gln Thr Val Gly Pro Asn Leu Val Leu Ala Asp
                245                 250                 255

Gln Lys Ala Pro Val Gln Leu Ala Ile Pro Val Gln Pro Pro Arg Ala
            260                 265                 270

Pro Thr Gln Thr Pro Gly Ile Asn Pro Val Asn Ser Thr Leu Ser Pro
            275                 280                 285

Ser Leu Gly Tyr Pro Thr Pro Leu Asp Arg Ala Gln Gly Asp Arg
    290                 295                 300

Leu Leu Asn Leu Val Gln Gly Val Tyr Leu Thr Leu Asn Leu Thr Ala
305                 310                 315                 320

Pro Asn Gln Thr Gln Asp Cys Trp Leu Cys Leu Thr Ala Lys Pro Pro
                325                 330                 335
```

Tyr Tyr Gln Gly Val Ala Ile Ile Gly Asn Phe Thr Asn His Thr Asn
            340                 345                 350

Ala Pro Leu Arg Cys Ser Thr Thr Pro Arg His Gly Leu Thr Leu Thr
            355                 360                 365

Glu Val Thr Gly His Gly Leu Cys Ile Gly Lys Ile Pro Pro Ser His
        370                 375                 380

Gln Asn Leu Cys Ser Gln Thr Ile Pro Ser Val Gly Gln Gly Pro Tyr
385                 390                 395                 400

Tyr Leu Thr Ala Pro Asn Gly Thr Tyr Trp Val Cys Asn Thr Gly Leu
                405                 410                 415

Thr Pro Cys Ile Ser Leu Gln Val Leu Asn Asn Thr Ala Asp Tyr Cys
            420                 425                 430

Ile Leu Ile Glu Leu Trp Pro Lys Ile Phe Tyr His Asp Ser Glu Tyr
            435                 440                 445

Ile Tyr Gly His Tyr Glu Pro Gly Gly Arg Phe Arg Arg Glu Pro Val
        450                 455                 460

Ser Leu Thr Val Ala Leu Leu Leu Gly Gly Leu Thr Met Gly Ser Leu
465                 470                 475                 480

Ala Ala Gly Ile Gly Thr Gly Thr Ala Ala Leu Ile Glu Thr Asn Gln
                485                 490                 495

Phe Lys Gln Leu Gln Ile Ala Met His Ser Asp Ile Gln Ala Leu Glu
            500                 505                 510

Glu Ser Ile Ser Ala Leu Glu Arg Ser Leu Thr Ser Leu Ser Glu Val
            515                 520                 525

Val Leu Gln Asn Arg Arg Gly Leu Asp Leu Leu Phe Leu Gln Glu Gly
            530                 535                 540

Gly Leu Cys Ala Ala Leu Lys Glu Glu Cys Cys Phe Tyr Ala Asp His
545                 550                 555                 560

Thr Gly Ile Val Arg Asp Ser Met Ala Lys Leu Arg Glu Arg Leu Lys
                565                 570                 575

Gln Arg Gln Lys Leu Phe Glu Ser Gln Gln Gly Trp Phe Glu Gly Trp
            580                 585                 590

Tyr Asn Lys Ser Pro Trp Phe Thr Thr Leu Val Ser Ser Leu Met Gly
            595                 600                 605

Pro Leu Ile Leu Leu Leu Leu Ile Leu Met Phe Gly Pro Cys Ile Leu
            610                 615                 620

Asn Arg Leu Val Gln Phe Ile Arg Glu Arg Leu Ser Val Ile Gln Ala
625                 630                 635                 640

Leu Val Leu Thr Gln Gln Tyr His Gln Leu Arg Gln Phe Asp Ala Glu
                645                 650                 655

Arg Pro Asp Thr Ile Glu
            660

<210> SEQ ID NO 3
<211> LENGTH: 511
<212> TYPE: PRT
<213> ORGANISM: Vesicular Stomatitis Virus

<400> SEQUENCE: 3

Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
                20                  25                  30

Val Pro Ser Asn Tyr His Tyr Cys Pro Ser Ser Ser Asp Leu Asn Trp

```
            35                  40                  45
His Asn Asp Leu Ile Gly Thr Ala Leu Gln Val Lys Met Pro Lys Ser
 50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr His
                85                  90                  95

Ser Ile Arg Ser Phe Thr Pro Ser Val Glu Gln Cys Lys Glu Ser Ile
                100                 105                 110

Glu Gln Thr Lys Gln Gly Thr Trp Leu Asn Pro Gly Phe Pro Pro Gln
            115                 120                 125

Ser Cys Gly Tyr Ala Thr Val Thr Asp Ala Glu Ala Val Ile Val Gln
        130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
                165                 170                 175

Val His Asn Ser Thr Thr Trp His Ser Asp Tyr Lys Val Lys Gly Leu
                180                 185                 190

Cys Asp Ser Asn Leu Ile Ser Met Asp Ile Thr Phe Phe Ser Glu Asp
            195                 200                 205

Gly Glu Leu Ser Ser Leu Gly Lys Glu Gly Thr Gly Phe Arg Ser Asn
210                 215                 220

Tyr Phe Ala Tyr Glu Thr Gly Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
    290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
        355                 360                 365

Glu Arg Glu Leu Trp Asp Asp Trp Ala Pro Tyr Glu Asp Val Glu Ile
    370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Ser Leu Phe Phe Gly Asp Thr Gly Leu Ser Lys
        435                 440                 445

Asn Pro Ile Glu Leu Val Glu Gly Trp Phe Ser Ser Trp Lys Ser Ser
450                 455                 460
```

```
Ile Ala Ser Phe Phe Ile Ile Gly Leu Ile Gly Leu Phe Leu
465                 470                 475                 480

Val Leu Arg Val Gly Ile His Leu Cys Ile Lys Leu Lys His Thr Lys
                        485                 490                 495

Lys Arg Gln Ile Tyr Thr Asp Ile Glu Met Asn Arg Leu Gly Lys
                500                 505                 510

<210> SEQ ID NO 4
<211> LENGTH: 685
<212> TYPE: PRT
<213> ORGANISM: Gibbon ape leukemia virus

<400> SEQUENCE: 4

Met Val Leu Leu Pro Gly Ser Met Leu Leu Thr Ser Asn Leu His His
1               5                   10                  15

Leu Arg His Gln Met Ser Pro Gly Ser Trp Lys Arg Leu Ile Ile Leu
                20                  25                  30

Leu Ser Cys Val Phe Gly Gly Gly Thr Ser Leu Gln Asn Lys Asn
            35                  40                  45

Pro His Gln Pro Met Thr Leu Thr Trp Gln Val Leu Ser Gln Thr Gly
    50                  55                  60

Asp Val Val Trp Asp Thr Lys Ala Val Gln Pro Pro Trp Thr Trp Trp
65                  70                  75                  80

Pro Thr Leu Lys Pro Asp Val Cys Ala Leu Ala Ala Ser Leu Glu Ser
                85                  90                  95

Trp Asp Ile Pro Gly Thr Asp Val Ser Ser Lys Arg Val Arg Pro
            100                 105                 110

Pro Asp Ser Asp Tyr Thr Ala Ala Tyr Lys Gln Ile Thr Trp Gly Ala
    115                 120                 125

Ile Gly Cys Ser Tyr Pro Arg Ala Arg Thr Arg Met Ala Ser Ser Thr
130                 135                 140

Phe Tyr Val Cys Pro Arg Asp Gly Arg Thr Leu Ser Glu Ala Arg Arg
145                 150                 155                 160

Cys Gly Gly Leu Glu Ser Leu Tyr Cys Lys Glu Trp Asp Cys Glu Thr
                165                 170                 175

Thr Gly Thr Gly Tyr Trp Leu Ser Lys Ser Ser Lys Asp Leu Ile Thr
            180                 185                 190

Val Lys Trp Asp Gln Asn Ser Glu Trp Thr Gln Lys Phe Gln Gln Cys
    195                 200                 205

His Gln Thr Gly Trp Cys Asn Pro Leu Lys Ile Asp Phe Thr Asp Lys
210                 215                 220

Gly Lys Leu Ser Lys Asp Trp Ile Thr Gly Lys Thr Trp Gly Leu Arg
225                 230                 235                 240

Phe Tyr Val Ser Gly His Pro Gly Val Gln Phe Thr Ile Arg Leu Lys
                245                 250                 255

Ile Thr Asn Met Pro Ala Val Ala Val Gly Pro Asp Leu Val Leu Val
            260                 265                 270

Glu Gln Gly Pro Pro Arg Thr Ser Leu Ala Leu Pro Pro Pro Leu Pro
    275                 280                 285

Pro Arg Glu Ala Pro Pro Ser Leu Pro Asp Ser Asn Ser Thr Ala
290                 295                 300

Leu Ala Thr Ser Ala Gln Thr Pro Thr Val Arg Lys Thr Ile Val Thr
305                 310                 315                 320

Leu Asn Thr Pro Pro Pro Thr Thr Gly Asp Arg Leu Phe Asp Leu Val
```

```
                    325                 330                 335
        Gln Gly Ala Phe Leu Thr Leu Asn Ala Thr Asn Pro Gly Ala Thr Glu
                    340                 345                 350

Ser Cys Trp Leu Cys Leu Ala Met Gly Pro Pro Tyr Tyr Glu Ala Ile
                    355                 360                 365

Ala Ser Ser Gly Glu Val Ala Tyr Ser Thr Asp Leu Asp Arg Cys Arg
                    370                 375                 380

Trp Gly Thr Gln Gly Lys Leu Thr Leu Thr Glu Val Ser Gly His Gly
        385                 390                 395                 400

Leu Cys Ile Gly Lys Val Pro Phe Thr His Gln His Leu Cys Asn Gln
                        405                 410                 415

Thr Leu Ser Ile Asn Ser Ser Gly Asp His Gln Tyr Leu Leu Pro Ser
                        420                 425                 430

Asn His Ser Trp Trp Ala Cys Ser Thr Gly Leu Thr Pro Cys Leu Ser
                        435                 440                 445

Thr Ser Val Phe Asn Gln Thr Arg Asp Phe Cys Ile Gln Val Gln Leu
                        450                 455                 460

Ile Pro Arg Ile Tyr Tyr Tyr Pro Glu Glu Val Leu Leu Gln Ala Tyr
        465                 470                 475                 480

Asp Asn Ser His Pro Arg Thr Lys Arg Glu Ala Val Ser Leu Thr Leu
                        485                 490                 495

Ala Val Leu Leu Gly Leu Gly Ile Thr Ala Gly Ile Gly Thr Gly Ser
                        500                 505                 510

Thr Ala Leu Ile Lys Gly Pro Ile Asp Leu Gln Gln Gly Leu Thr Ser
                        515                 520                 525

Leu Gln Ile Ala Ile Asp Ala Asp Leu Arg Ala Leu Gln Asp Ser Val
                        530                 535                 540

Ser Lys Leu Glu Asp Ser Leu Thr Ser Leu Ser Glu Val Val Leu Gln
        545                 550                 555                 560

Asn Arg Arg Gly Leu Asp Leu Leu Phe Leu Lys Glu Gly Gly Leu Cys
                        565                 570                 575

Ala Ala Leu Lys Glu Glu Cys Cys Phe Tyr Ile Asp His Ser Gly Ala
                        580                 585                 590

Val Arg Asp Ser Met Lys Lys Leu Lys Glu Lys Leu Asp Lys Arg Gln
                        595                 600                 605

Leu Glu Arg Gln Lys Ser Gln Asn Trp Tyr Glu Gly Trp Phe Asn Asn
                        610                 615                 620

Ser Pro Trp Phe Thr Thr Leu Leu Ser Thr Ile Ala Gly Pro Leu Leu
        625                 630                 635                 640

Leu Leu Leu Leu Leu Leu Ile Leu Gly Pro Cys Ile Ile Asn Lys Leu
                        645                 650                 655

Val Gln Phe Ile Asn Asp Arg Ile Ser Ala Val Lys Ile Leu Val Leu
                        660                 665                 670

Arg Gln Lys Tyr Gln Ala Leu Glu Asn Glu Gly Asn Leu
                        675                 680                 685

<210> SEQ ID NO 5
<211> LENGTH: 565
<212> TYPE: PRT
<213> ORGANISM: Artificial Sequence
<220> FEATURE:
<223> OTHER INFORMATION: RD114TR fusion protein

<400> SEQUENCE: 5

Met Lys Leu Pro Thr Gly Met Val Ile Leu Cys Ser Leu Ile Ile Val
```

-continued

```
  1               5               10              15
Arg Ala Gly Phe Asp Asp Pro Arg Lys Ala Ile Ala Leu Val Gln Lys
              20              25              30
Gln His Gly Lys Pro Cys Glu Cys Ser Gly Gly Gln Val Ser Glu Ala
              35              40              45
Pro Pro Asn Ser Ile Gln Gln Val Thr Cys Pro Gly Lys Thr Ala Tyr
 50              55              60
Leu Met Thr Asn Gln Lys Trp Lys Cys Arg Val Thr Pro Lys Asn Leu
 65              70              75              80
Thr Pro Ser Gly Gly Glu Leu Gln Asn Cys Pro Cys Asn Thr Phe Gln
              85              90              95
Asp Ser Met His Ser Ser Cys Tyr Thr Glu Tyr Arg Gln Cys Arg Ala
             100             105             110
Asn Asn Lys Thr Tyr Tyr Thr Ala Thr Leu Leu Lys Ile Arg Ser Gly
             115             120             125
Ser Leu Asn Glu Val Gln Ile Leu Gln Asn Pro Asn Gln Leu Leu Gln
             130             135             140
Ser Pro Cys Arg Gly Ser Ile Asn Gln Pro Val Cys Trp Ser Ala Thr
145             150             155             160
Ala Pro Ile His Ile Ser Asp Gly Gly Pro Leu Asp Thr Lys Arg
             165             170             175
Val Trp Thr Val Gln Lys Arg Leu Glu Gln Ile His Lys Ala Met His
             180             185             190
Pro Glu Leu Gln Tyr His Pro Leu Ala Leu Pro Lys Val Arg Asp Asp
             195             200             205
Leu Ser Leu Asp Ala Arg Thr Phe Asp Ile Leu Asn Thr Thr Phe Arg
210             215             220
Leu Leu Gln Met Ser Asn Phe Ser Leu Ala Gln Asp Cys Trp Leu Cys
225             230             235             240
Leu Lys Leu Gly Thr Pro Thr Pro Leu Ala Ile Pro Thr Pro Ser Leu
             245             250             255
Thr Tyr Ser Leu Ala Asp Ser Leu Ala Asn Ala Ser Cys Gln Ile Ile
             260             265             270
Pro Pro Leu Leu Val Gln Pro Met Gln Phe Ser Asn Ser Ser Cys Leu
             275             280             285
Ser Ser Pro Phe Ile Asn Asp Thr Glu Gln Ile Asp Leu Gly Ala Val
             290             295             300
Thr Phe Thr Asn Cys Thr Ser Val Ala Asn Val Ser Ser Pro Leu Cys
305             310             315             320
Ala Leu Asn Gly Ser Val Phe Leu Cys Gly Asn Asn Met Ala Tyr Thr
             325             330             335
Tyr Leu Pro Gln Asn Trp Thr Gly Leu Cys Val Gln Ala Ser Leu Leu
             340             345             350
Pro Asp Ile Asp Ile Ile Pro Gly Asp Glu Pro Val Pro Ile Pro Ala
             355             360             365
Ile Asp His Tyr Ile His Arg Pro Lys Arg Ala Val Gln Phe Ile Pro
             370             375             380
Leu Leu Ala Gly Leu Gly Ile Thr Ala Ala Phe Thr Thr Gly Ala Thr
385             390             395             400
Gly Leu Gly Val Ser Val Thr Gln Tyr Thr Lys Leu Ser His Gln Leu
             405             410             415
Ile Ser Asp Val Gln Val Leu Ser Gly Thr Ile Gln Asp Leu Gln Asp
             420             425             430
```

-continued

```
Gln Val Asp Ser Leu Ala Glu Val Val Leu Gln Asn Arg Arg Gly Leu
        435                 440                 445

Asp Leu Leu Thr Ala Glu Gln Gly Gly Ile Cys Leu Ala Leu Gln Glu
        450                 455                 460

Lys Cys Cys Phe Tyr Ala Asn Lys Ser Gly Ile Val Arg Asn Lys Ile
465                 470                 475                 480

Arg Thr Leu Gln Glu Glu Leu Gln Lys Arg Arg Glu Ser Leu Ala Ser
                485                 490                 495

Asn Pro Leu Trp Thr Gly Leu Gln Gly Phe Leu Pro Tyr Leu Leu Pro
                500                 505                 510

Leu Leu Gly Pro Leu Leu Thr Leu Leu Ile Leu Thr Ile Gly Pro
            515                 520                 525

Cys Val Phe Ser Arg Leu Met Ala Phe Ile Asn Asp Arg Leu Asn Val
        530                 535                 540

Val His Ala Met Val Leu Ala Gln Gln Tyr Gln Ala Leu Lys Ala Glu
545                 550                 555                 560

Glu Glu Ala Gln Asp
                565
```